(12) United States Patent
Lu et al.

(10) Patent No.: US 11,014,904 B2
(45) Date of Patent: May 25, 2021

(54) 1,2,4-TRIAZINE-3-AMINE DERIVATIVE, PREPARATION METHOD THEREFOR, AND USE THEREOF IN MEDICINE

(71) Applicants: Jiangsu Hengrui Medicine Co., Ltd., Jiangsu (CN); Shanghai Hengrui Pharmaceutical Co., Ltd., Shanghai (CN)

(72) Inventors: Biao Lu, Shanghai (CN); Junzhen Zhang, Shanghai (CN); Fangfang Jin, Shanghai (CN); Feng He, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 2 days.

(21) Appl. No.: 16/477,011

(22) PCT Filed: Jan. 12, 2018

(86) PCT No.: PCT/CN2018/072308
§ 371 (c)(1),
(2) Date: Jul. 10, 2019

(87) PCT Pub. No.: WO2018/130184
PCT Pub. Date: Jul. 19, 2018

(65) Prior Publication Data
US 2019/0352278 A1 Nov. 21, 2019

(30) Foreign Application Priority Data

Jan. 13, 2017 (CN) .......................... 201710023970.7
Sep. 25, 2017 (CN) .......................... 201710874488.4

(51) Int. Cl.
| | | |
|---|---|---|
| C07D 401/04 | (2006.01) |
| C07D 401/14 | (2006.01) |
| C07D 403/04 | (2006.01) |
| C07D 405/14 | (2006.01) |
| C07D 409/14 | (2006.01) |
| C07D 413/14 | (2006.01) |

(52) U.S. Cl.
CPC ......... *C07D 401/04* (2013.01); *C07D 401/14* (2013.01); *C07D 403/04* (2013.01); *C07D 405/14* (2013.01); *C07D 409/14* (2013.01); *C07D 413/14* (2013.01)

(58) Field of Classification Search
CPC .. C07D 253/06; C07D 401/04; C07D 401/14; C07D 403/04; C07D 403/14; C07D 405/14; C07D 409/14; C07D 487/04; A61K 31/53; A61P 35/00
See application file for complete search history.

(56) References Cited

FOREIGN PATENT DOCUMENTS

| CN | 102822150 A | 12/2012 |
|---|---|---|
| WO | 2006132739 A2 | 12/2006 |
| WO | 2007116106 A1 | 10/2007 |
| WO | 2009080197 A1 | 7/2009 |
| WO | 2011020193 A1 | 2/2011 |
| WO | 2011084402 A1 | 7/2011 |
| WO | 2011095625 A1 | 8/2011 |
| WO | 2011159302 A1 | 12/2011 |
| WO | 2012009194 A1 | 1/2012 |
| WO | 2013014997 A1 | 1/2013 |
| WO | 2014101373 A1 | 7/2014 |
| WO | 2015031221 A1 | 3/2015 |
| WO | 2016102672 A2 | 6/2016 |

OTHER PUBLICATIONS

Csoka et al., Adenosine promotes alternative macrophage activation via A2a and A2b receptors, The FASEB Journal, vol. 26, pp. 376-386, Jan. 2012.*
Damasio, Alzheimer's Disease and related dementias, Cecil Textbook of Medicine, 20th Edition, vol. 2, pp. 1992-6, 1996.*
Layzer, Degenerative diseases of the nervous system, Cecil Textbook of Medicine, 20th Edition, vol. 2, pp. 2050-7, 1996.*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*

(Continued)

*Primary Examiner* — Deepak R Rao
(74) *Attorney, Agent, or Firm* — Ice Miller LLP

(57) ABSTRACT

A 1,2,4-triazine-3-amine derivative, a preparation therefor, and use thereof in medicine are provided. Specifically, a 1,2,4-triazine-3-amine derivative as represented by general formula (I), a preparation method therefor, a pharmaceutical composition containing the derivative, and use thereof as a therapeutic agent, in particular as an $A_{2a}$ or $A_{2b}$ receptor antagonist, and use thereof in the preparation of a medicament for treating a condition or disorder that is ameliorated by means of inhibition of the $A_{2a}$ or $A_{2b}$ receptor are provided. Each substituent in general formula (I) is defined in the description.

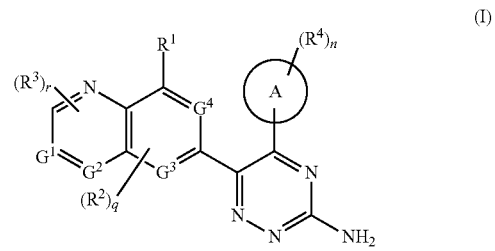

14 Claims, No Drawings

(56) References Cited

OTHER PUBLICATIONS

Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Black et al, "Quantification of Indirect Pathway Inhibition by the Adenosine A2a Antagonist SYN115 in Parkinson Disease," The Journal of Neuroscience, vol. 30, No. 48, pp. 16284-16292 (2010).
Brooks et al, "An Open-Label, Positron Emission Tomography Study to Assess Adenosine A2A Brain Receptor Occupancy of Vipadenant (BIIB014) at Steady-State Levels in Healthy Male Volunteers," Clinical Neuropharmacology, vol. 33, No. 2, pp. 55-60 (2010).
Congreve et al., "Discovery of 1,2,4-Triazine Derivatives as Adenosine A2A Antagonists using Structure Based Drug Design," Journal of Medicinal Chemistry, vol. 55, pp. 1898-1903 (2012).
Devine et al., "Protozoan Parasite Growth Inihibitors Discovered by Cross-Screening Yield Potent Scaffolds for Lead Discovery," Journal of Medicinal Chemistry, vol. 58, pp. 5522-5537 (2015).
Factor et al, "A long-term study of istradefylline in subjects with fluctuating Parkinson's disease," Parkinsonism and Related Disorders, vol. 16, No. 6, pp. 423-426 (2010).
Furuya et al., "Fluorination of Boronic Acids Mediated by Silver(I) Triflate," Organic Letter, vol. 11, No. 13, pp. 2860-2863 (2009).
Gessi et al., "The A3 adensine receptor: An enigmatic player in cell biology," Pharmacology & Therapeutics, vol. 117, pp. 123-140 (2008).
Green et al., "Design, Synthesis, and Structure-Activity Relationships of Pyridine Based Rho Kinase (ROCK) Inhibitors," Journal of Medicinal Chemistry, vol. 58, pp. 5028-5037 (2015).
Hinsberger et al., "Benzamidobenzoic acids as potent PqsD inhibitors for the treatment of Pseudomonas aeruginosa infections," European Journal of Medicinal Chemistry, vol. 76, pp. 343-351 (2014).
Jenner, P., "Pathophysiology and biochemistry of dyskinesia: clues for the development of non-dopaminergic treatments," J. Neurol., vol. 247, Suppl. 2, pp. II/43-II/50 (2000).
Kammber et al., "1,2,4-Triazines Are Versatile Bioorthogonal Reagents," Journal of the American Chemical Society, vol. 137, pp. 8388-8391 (2015).
Kinuta et al., "Rhodium-Catalyzed Borylation of Ary 2-Pyridyl Esters through Cleavage of the Carbon-Oxygen Bond: Borylative Removal of the Directing Group," Journal of the American Chemical Society, vol. 137, pp. 1593-1600 (2015).
Lamberth et al., "2,2,3-Tribromopropanal as a Versatile Reagent in the Skraup-Type Synthesis of 3-Bromoquinolin-6-ols," SYNLETT, vol. 25, pp. 0858-0862 (2014).
Lang et al., "Efficient Synthesis of Heterocyclic Neurotensin Receptor Ligands by Microwave-Assisted Aminocarbonylation," Synthesis, vol. 45, No. 17, pp. 2474-2480 (2013).
Lokshin et al., "Adenosine-Mediated Inhibition of the Cytotoxic Activity and Cytokine Production by Activated Natural Killer Cells," Cander Res., vol. 66, No. 15, pp. 7758-7765 (Aug. 1, 2006).
Marciniec et al., "Synthesis of 6- and *-Halogenosubstituted 3-Quinoline-Sulfonic Acid Derivatives[1]," J. Heterocyclic Chem., vol. 52, pp. 1019-1025 (Jul. 2015).
Maximino et al., "Adenosine A1, but not A2, Receptor Blockade Increases Anxiety and Arousal in Zebrafish," Basic & Clinical Pharmacology & Toxicology, vol. 109, pp. 203-207 (2011).
Mittal et al., "Adenosine 2B Receptor Expression on Cancer Cells Promotes Metastasis," Cancer Res., vol. 76, No. 15, pp. 4372-4382 (Aug. 1, 2006).
Nishimura et al., "Phospshoinositide 3-Kinase (PI3K)/Mammalian Target of Rapamycin (mTOR) Dual Inhibitors: Discovery and Structure-Activity Relationships of a Series of Quinoline and Quinoxaline Derivatives," Journal of Medicinal Chemistry, vol. 54, pp. 4735-4751 (2011).
Papapetropoulos et al, "The adenosine A2A receptor antagonist BIIB014 is effective in improving ON-time in Parkinson's disease (PD) patients with motor fluctuations," Movement Disorders, vol. 25, Suppl. 2, p. S305 (2010).
Paul et al., "Hexamethonium bis(tribromide) (HMBTB) a recyclable and high bromine containing reagent," Tetrahedron Letters, vol. 56, pp. 5646-5650 (2015).
Press et al, "Therapeutic potential of adenosine receptor antagonists and agonists," Expert Opinion on Therapeutic Patents, vol. 17, No. 8, pp. 979-991 (2007).
Ranu et al., "Efficient microwave-assisted synthesis of quinolines and dihydroquinolines under solvent-free conditions," Tetrahedron, vol. 59, pp. 813-819 (2003).
Schwarzschild et al, "Targeting adenosine A2A receptors in Parkinson's disease," Trends in Neurosciences, vol. 29, No. 11, pp. 647-654 (2006).
Struss et al., "Polymeric DABCO-bromine complex: a mild oxidant for the preparation of ketones and aldehydes," Tetrahedron Letters, vol. 47, pp. 6635-6636 (2006).
Wang, et al., "Rhodium(III)-Catalyzed Intermolecular Amidation with Azides via C(sp3)-H Functionalization," The Journal of Organic Chemistry, vol. 79, pp. 5379-5385 (2014).
Zhang et al., "An Extremely Stable and Orthogonal DNA Base Pair with a Simplified Three-Carbon Backbone," J. Am. Chem. Soc., vol. 127, pp. 74-75 (2005).
Zhu et al., "Facile and efficient synthesis of quinoline-4-carboxylic acids under microwave irradiation," Chinese Chemical Letters, vol. 21, pp. 35-38 (2010).
Zong et al., "Progress in research on effects of adenosine A1 receptors," Chinese Pharmacological Bulletin, vol. 24, No. 5, pp. 573-576 (2008) (Last Page English Abstract).

* cited by examiner

US 11,014,904 B2

1,2,4-TRIAZINE-3-AMINE DERIVATIVE, PREPARATION METHOD THEREFOR, AND USE THEREOF IN MEDICINE

CROSS-REFERENCE TO RELATED APPLICATION

This application is a Section 371 of International Application No. PCT/CN2018/072308 filed Jan. 12, 2018, which was published in the Chinese language on Jul. 19, 2018, under International Publication No. WO 2018/130184 A1, which claims priority under 35 U.S.C. § 119(b) to Chinese Application No. 201710023970.7, filed Jan. 13, 2017 and Chinese Application No. 201710874488.4, filed Sep. 25, 2017, the disclosures of which are incorporated herein by reference in its/their entirety.

FIELD OF THE INVENTION

The present invention belongs to the field of medicine, and relates to a 1,2,4-triazin-3-amine derivative of formula (I), a method for preparing the same, a pharmaceutical composition comprising the same, a use thereof as a therapeutic agent, in particular as an $A_{2a}$ receptor antagonist, and a use thereof in the preparation of a medicament for treating a disease or condition ameliorated by the inhibition of the $A_{2a}$ receptor.

BACKGROUND OF THE INVENTION

Adenosine is a naturally occurring purine nucleoside, and is an endogenous regulator of many physiological functions. It plays an important role in the regulation of the cardiovascular system, central nervous system, respiratory system, kidney, fat and platelets.

The action of adenosine is mediated by a family of G-protein coupled receptors. It is known currently that there are at least four subtypes of adenosine receptors, which are classified into $A_1$, $A_{2a}$, $A_{2b}$ and $A_3$. Among them, the $A_1$ and $A_3$ receptors inhibit the activity of the enzyme adenylate cyclase, whereas the $A_{2a}$ and $A_{2b}$ receptors stimulate the activity of the same enzyme, thereby modulating the level of cyclic AMP in cells. Adenosine regulates a wide range of physiological functions through these receptors.

The $A_{2a}$ receptor ($A_{2a}R$) is widely distributed in the body, and is mainly expressed in the striatum in the central nervous system, and is also expressed in tissues such as the periphery, heart, liver, lung and kidney. Several preclinical studies show that adenosine $A_{2a}$ receptor antagonists have surprising efficacy in the treatment of neurodegenerative diseases, primarily Parkinson's disease, Huntington's disease or Alzheimer's disease (*Trends in Neurosci.* 2006, 29(11), 647-654; *Expert Opinion on Therapeutic Patents*, 2007, 17, 979-991 and the like). Moreover, adenosine $A_{2a}$ receptor antagonists can also be used to treat other central nervous system (CNS) related diseases such as depression, restless syndrome, sleep disorders and anxiety disorders (*Clin. Neuropharmacol.* 2010, 33, 55-60; *J. Neurosci.* 2010, 30 (48), 16284-16292; *Parkinsonisn Relat. Disord.* 2010, 16 (6), 423-426; and references therein: Mov. Disorders, 2010, 25(2), S305). In addition, adenosine $A_{2a}$ receptor antagonists also have therapeutic potential as neuroprotective agents (see Jenner P. *J Neurol.* 2000; 24 7Suppl 2: 1143-50).

Recent studies indicate that the activation of the adenosine $A_{2a}$ receptor can exert an important immunomodulatory effect in many pathological processes such as ischemia, hypoxia, inflammation, trauma, transplantation and the like, which may be related to the higher expression level of the $A_{2a}$ receptor in various immune cells such as T cells, B cells, monocyte macrophages, neutrophils and the like. Moreover, the activation of the $A_{2a}$ receptor can promote the body to generate immune tolerance, and closely participate in the formation of "immune escape" or "immunosuppression" of tumor cells, thereby creating a favorable condition for the occurrence and development of tumors. Lokshin and his colleagues (*Cancer Res.* 2006, Aug. 1; 66 (15):7758-65) demonstrate that the activation of $A_{2a}R$ in natural killer cells can inhibit the killing of tumor cells by natural killer cells through increasing cAMP and activating PKA. Studies also show that the activation of $A_{2a}$ receptor can promote the proliferation of tumor cells such as melanoma A375 cells, fibroblast NIH3T3 cells, pheochromocytoma PC12 cells and the like, which may be related to the fact that the activation of the $A_{2a}$ receptor in T cells can inhibit T cell activation, proliferation, adhesion to tumor cells, and produce cytotoxic effect on tumor cells. However, in the $A_{2a}$ receptor knockout mice, the anti-tumor immunity of $CD8^+$ T cells is enhanced, and the tumor proliferation is significantly inhibited. Therefore, $A_{2a}$ receptor antagonists can be used in the treatment of tumor. Deepak Mittal et al. find that the combination administration of $A_{2b}$ receptor inhibitors with chemotherapeutic drugs or immunological checkpoint inhibitors can significantly reduce tumor metastasis in a mice triple negative breast cancer model; the knockout of the $A_{2b}$ receptor in mice or human colon cancer cell line significantly reduces colon cancer metastasis and cell tumorigenicity; meanwhile, the study finds that the $A_{2b}$ receptor is highly expressed in human triple negative breast cancer cell line, and the expression level of the $A_{2b}$ receptor is closely related to tumor progression. These results show that inhibition of the $A_{2b}$ receptor can inhibit tumor metastasis, and the $A_{2b}$ receptor is thus expected to be an ideal target for the treatment of tumors (Cancer Res. 2016 Aug. 1; 76(15):4372-82). The development of dual inhibitors of the $A_{2a}$ receptor and the $A_{2b}$ receptor has also become a direction worth exploring.

Although compounds having significant biological activity on a variety of subtypes of adenosine receptors can have a therapeutic effect, they can cause undesired side effects. For example, during tissue ischemia/hypoxia, when cells of central system, circulatory system, digestive system, and skeletal muscle are in an anoxic and hypoxic stress environment, extracellular aggregated adenosine initiates a corresponding protective mechanism by activating the adenosine $A_1$ receptor on the cell membrane, thereby increasing the tolerance of the cells to anoxia and hypoxia. The $A_1$ receptor located on immune cells can promote cellular immune responses in a hypoxic environment. Moreover, the $A_1$ receptor can also reduce free fatty acids and triglycerides, and is involved in regulating blood glucose. Therefore, the continued blocking of the $A_1$ receptor can cause various adverse effects in the body tissues (*Chinese Pharmacological Bulletin*, 2008, 24(5), 573-576). For example, it is reported that the blocking of the $A_1$ receptor will cause adverse effects such as anxiety, awakening and the like in animal models (*Basic & Clinical Pharmacology & Toxicology*, 2011, 109 (3), 203-7). The adenosine released by the adenosine A₃ receptor during myocardial ischemia exerts a strong protective effect in heart (as described by Gessi S et al, *Pharmacol. Ther.* 117 (1), 2008, 123-140). The continued blocking of the $A_3$ receptor can increase the likelihood of complications caused by any pre-existing or developing ischemic heart disease such as angina or heart failure.

Currently, many compounds have been developed as $A_{2a}$ receptor antagonists for the treatment of various diseases, as described in WO2007116106, WO2009080197, WO2011159302, WO2011095625, WO2014101373 and WO2015031221. However, there still exist problems such as low solubility, photosensitivity, low activity, low selectivity and low bioavailability.

WO2011095625 discloses a 1,2,4-triazin-4-amine derivative of formula (A1) and use thereof in the treatment of a disease or condition ameliorated by the inhibition of the $A_1$ receptor or the $A_{2a}$ receptor.

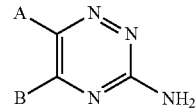

(A1)

This patent application discloses a total of more than 200 examples, among which there are only five examples in which the ring A is a fused aromatic ring. The data in this patent application show that when ring A is a fused aromatic ring, the inhibition activity on the $A_{2a}R$ is weak (see Table 1).

TABLE 1

| | Examples in the patent application WO2011095625 | |
|---|---|---|
| Example No. | Structure | pKi/$A_{2a}$R (determined in this patent application) |
| 1(lxxii) i.e., Example 13 of the present invention | [structure 13] | 6.99 |
| 1(xviii) | [structure] | 6.75 |
| 1(xxii) | [structure] | No data provided |
| 1(xxxv) | [structure] | 7.19 |

TABLE 1-continued

Examples in the patent application WO2011095625

| Example No. | Structure | pKi/$A_{2a}R$ (determined in this patent application) |
|---|---|---|
| 1(cxlii) | 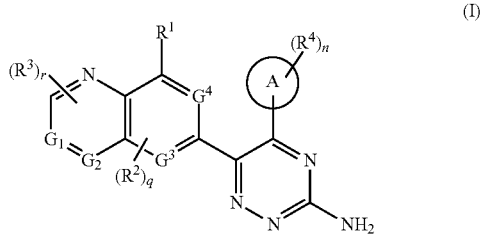 | No data provided |

Among them, ring A of Example 1 (lxxii) is naphthyl. We have now found that a derivative in which a nitrogen atom is introduced at the 5-position of the naphthyl shows a surprising activity, and the inhibition activity on the $A_{2a}R$ is 30 to 1500 times or more than that of Example 1 (lxxii). Such a strong inhibition activity cannot be expected when reading WO2011095625.

Therefore, the present invention provides a novel structure of an adenosine $A_{2a}$ receptor antagonist with a strong inhibition activity, and the compounds having such a structure also have a good inhibition effect on the adenosine $A_{2b}$ receptor and a weak inhibition effect on the adenosine $A_1$ receptor and the adenosine $A_3$ receptor, exhibiting a good selectivity for the adenosine $A_{2a}$ receptor. Meanwhile, the compounds having such a structure exhibit an excellent anti-tumor effect and pharmacokinetics activity.

SUMMARY OF THE INVENTION

The object of the present invention is to provide a compound of formula (I):

(I)

or a tautomer, mesomer, racemate, enantiomer, or diastereomer thereof, or a mixture thereof, or a pharmaceutically acceptable salt thereof,
wherein:
ring A is aryl or heteroaryl;
$G^1$, $G^2$, $G^3$ and $G^4$ are identical or different and each are independently selected from the group consisting of C, CH and N;
$R^1$ is selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

each $R^3$ is identical or different and each is independently selected from the group consisting of hydrogen, halogen, alkyl, alkoxy, haloalkyl, deuterated alkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, deuterium, alkyl, alkoxy, haloalkyl, hydroxy, hydroxyalkyl, cyano, amino, nitro, cycloalkyl, heterocyclyl, aryl and heteroaryl;

each $R^4$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^5$ is selected from the group consisting of hydrogen, alkyl, haloalkyl, amino, hydroxy, cycloalkyl, heterocyclyl, aryl and heteroaryl;

$R^6$ and $R^7$ are each independently selected from the group consisting of hydrogen, alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, $R^6$ and $R^7$ together with the nitrogen atom to which they are attached form a heterocyclyl, wherein the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

m is 0, 1 or 2;
r is 0, 1, 2 or 3;
q is 0, 1 or 2; and
n is 0, 1, 2, 3, 4 or 5.

In a preferred embodiment of the present invention, the compound of formula (I) is a compound of formula (Iaa):

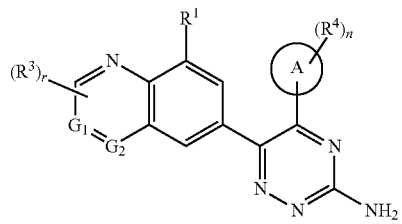

(Iaa)

or a tautomer, mesomer, racemate, enantiomer, or diastereomer thereof, or a mixture thereof, or a pharmaceutically acceptable salt thereof,
wherein
ring A, $G^1$, $G^2$, $R^1$, $R^3$, $R^4$, r and n are as defined in formula (I).

In a preferred embodiment of the present invention, the compound of formula (I) is a compound of formula (Ibb):

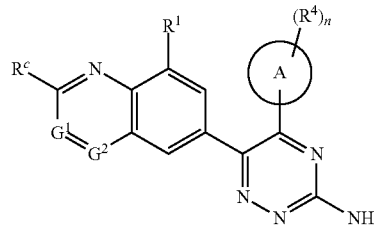

(Ibb)

or a tautomer, mesomer, racemate, enantiomer, or diastereomer thereof, or a mixture thereof, or a pharmaceutically acceptable salt thereof,
wherein
$G^1$ and $G^2$ are identical or different and are each independently $CR^a$ or N;
$R^a$ is selected from the group consisting of hydrogen, halogen, alkyl, alkoxy, haloalkyl, deuterated alkyl, hydroxy, hydroxyalkyl, cyano, amino, nitro, cycloalkyl, heterocyclyl, aryl and heteroaryl, wherein the alkyl, alkoxy, cycloalkyl, heterocyclyl, aryl and heteroaryl are each independently optionally substituted by one or more substituents selected from the group consisting of halogen, deuterium, alkyl, alkoxy, haloalkyl, hydroxy, hydroxyalkyl, cyano, amino, nitro, cycloalkyl, heterocyclyl, aryl and heteroaryl;

$R^c$ is selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl;
ring A, $R^1$, $R^4$ and n are as defined in formula (I).

In a preferred embodiment of the present invention, the compound of formula (I) is a compound of formula (II):

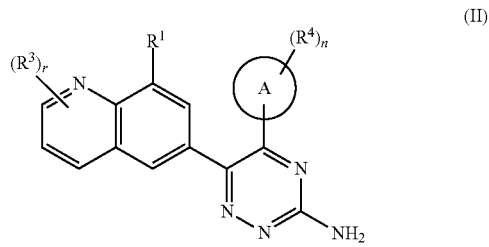

(II)

or a tautomer, mesomer, racemate, enantiomer, or diastereomer thereof, or a mixture thereof, or a pharmaceutically acceptable salt thereof,
wherein ring A, $R^1$, $R^3$, $R^4$, r and n are as defined in formula (I).

In a preferred embodiment of the present invention, in the compound of formula (I), ring A is selected from the group consisting of phenyl, pyridyl, thienyl and furanyl.

In a preferred embodiment of the present invention, the compound of formula (I) is a compound of formula (III):

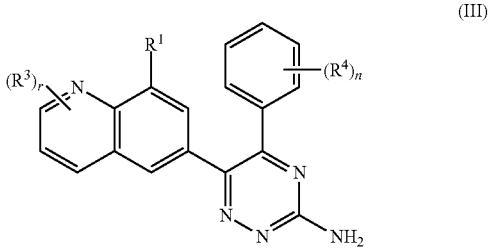

(III)

or a tautomer, mesomer, racemate, enantiomer, or diastereomer thereof, or a mixture thereof, or a pharmaceutically acceptable salt thereof,
wherein $R^1$, $R^3$, $R^4$, r and n are as defined in formula (I).

In a preferred embodiment of the present invention, in the compound of formula (I), $R^1$ is selected from the group consisting of hydrogen, halogen, alkyl, alkoxy, cyano, cycloalkyl, haloalkyl, heterocyclyl and —C(O)NR$^6$R$^7$; $R^6$ and $R^7$ are as defined in formula (I); the halogen is preferably fluorine, chlorine or bromine, the alkyl is preferably methyl, ethyl, isopropyl or n-butyl, the alkoxy is preferably methoxy or ethoxy, and the cycloalkyl is preferably cyclopropyl, cyclopentyl or cyclohexyl.

In a preferred embodiment of the present invention, in the compound of formula (I), each $R^3$ is identical or different and each is independently selected from the group consisting of hydrogen, halogen, alkyl, haloalkyl, deuterated alkyl, alkoxy, cyano, cycloalkyl and heterocyclyl, wherein the alkyl and alkoxy are each independently optionally substituted by one or more substituents selected from the group consisting of halogen, deuterium, hydroxy, cyano, amino, nitro, cycloalkyl and heterocyclyl; the halogen is preferably fluorine, chlorine or bromine, the alkyl is preferably methyl, ethyl, isopropyl or n-butyl, the alkoxy is preferably methoxy or ethoxy, and the heterocyclyl is preferably piperidinyl, piperazinyl, morpholinyl or tetrahydropyranyl.

In a preferred embodiment of the present invention, in the compound of formula (I), each $R^4$ is identical or different and each is independently selected from the group consisting of hydrogen, alkyl and halogen.

Typical compounds of the present invention include, but are not limited to:

| Example No. | Structure and name of the compound |
|---|---|
| 1 | 6-(8-Methylquinolin-6-yl)-5-phenyl-1,2,4-triazin-3-amine 1 |
| 2 | 6-(8-Fluoroquinolin-6-yl)-5-phenyl-1,2,4-triazin-3-amine 2 |
| 3 | 5-Phenyl-6-(quinolin-6-yl)-1,2,4-triazin-3-amine 3 |
| 4 | 6-(8-Chloroquinolin-6-yl)-5-phenyl-1,2,4-triazin-3-amine 4 |
| 5 | 5-(5-Methylfuran-2-yl)-6-(8-methylquinolin-6-yl)-1,2,4-triazin-3-amine 5 |
| 6 | 5-(Furan-2-yl)-6-(8-methylquinolin-6-yl)-1,2,4-triazin-3-amine 6 |
| 7 | 6-(8-Methylquinolin-6-yl)-5-(thiophen-2-yl)-1,2,4-triazin-3-amine 7 |
| 8 | 5-(4-Fluorophenyl)-6-(8-methylquinolin-6-yl)-1,2,4-triazin-3-amine 8 |

| Example No. | Structure and name of the compound |
|---|---|
| 9 | 5-Phenyl-6-(8-(trifluoromethyl)quinolin-6-yl)-1,2,4-triazin-3-amine 9 |
| 10 | 6-(8-Isopropylquinolin-6-yl)-5-phenyl-1,2,4-triazin-3-amine 10 |
| 11 | 6-(8-Ethylquinolin-6-yl)-5-phenyl-1,2,4-triazin-3-amine 11 |
| 12 | 6-(8-Cyclopropylquinolin-6-yl)-5-phenyl-1,2,4-triazin-3-amine 12 |
| 13 (Comparative example 1) | 6-(Naphthalen-2-yl)-5-phenyl-1,2,4-triazin-3-amine 13 |
| 14 | 6-(4-Methylquinolin-6-yl)-5-phenyl-1,2,4-triazin-3-amine 14 |
| 15 | 6-(4-Methylquinazolin-6-yl)-5-phenyl-1,2,4-triazin-3-amine 15 |
| 16 | 6-(8-Fluoro-4-methylquinolin-6-yl)-5-phenyl-1,2,4-triazin-3-amine 16 |

| Example No. | Structure and name of the compound |
|---|---|
| 17 | 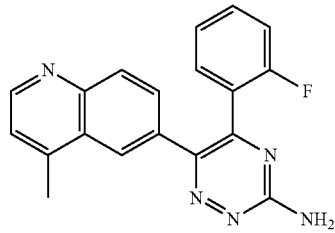<br>5-(2-Fluorophenyl)-6-(4-methylquinolin-6-yl)-1,2,4-triazin-3-amine 17 |
| 18 | 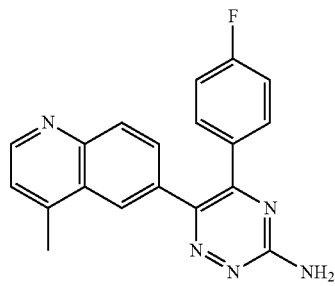<br>5-(4-Fluorophenyl)-6-(4-methylquinolin-6-yl)-1,2,4-triazin-3-amine 18 |
| 19 | 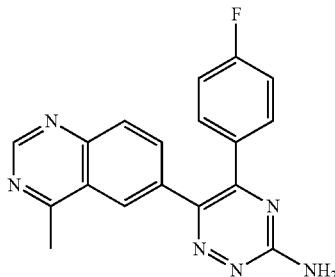<br>5-(4-Fluorophenyl)-6-(4-methylquinazolin-6-yl)-1,2,4-triazin-3-amine 19 |
| 20 | 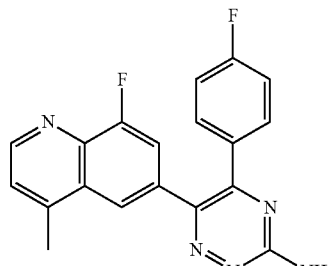<br>6-(8-Fluoro-4-methylquinolin-6-yl)-5-(4-fluorophenyl)-1,2,4-triazin-3-amine 20 |
| 21 | 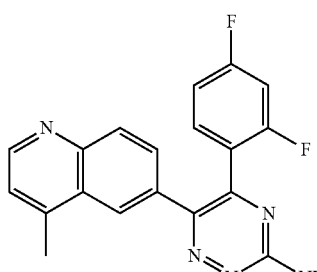<br>5-(2,4-Difluorophenyl)-6-(4-methylquinolin-6-yl)-1,2,4-triazin-3-amine 21 |
| 22 | 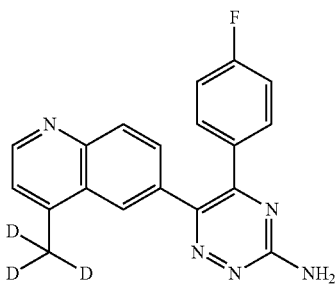<br>5-(4-Fluorophenyl)-6-[4-(trideuteromethyl)-6-quinolinyl]-1,2,4-triazin-3-amine 22 |
| 23 | 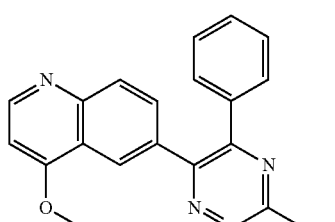<br>6-(4-Methoxyquinolin-6-yl)-5-phenyl-1,2,4-triazin-3-amine 23 |
| 24 | 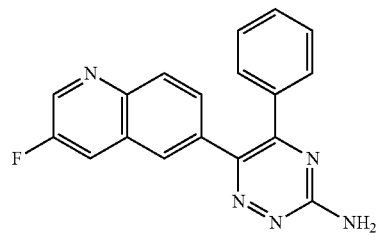<br>6-(3-Fluoroquinolin-6-yl)-5-phenyl-1,2,4-triazin-3-amine 24 |

-continued

| Example No. | Structure and name of the compound |
|---|---|
| 25 | 6-(8-Methoxyquinolin-6-yl)-5-phenyl-1,2,4-triazin-3-amine 25 |
| 26 | 5-(3-Fluorophenyl)-6-(8-fluoroquinolin-6-yl)-1,2,4-triazin-3-amine 26 |
| 27 | 6-(4-Chloroquinolin-6-yl)-5-(4-fluorophenyl)-1,2,4-triazin-3-amine 27 |
| 28 | 6-(3-Methylquinolin-6-yl)-5-phenyl-1,2,4-triazin-3-amine 28 |
| 29 | 5-Phenyl-6-(quinazolin-6-yl)-1,2,4-triazin-3-amine 29 |
| 30 | 5-(4-Fluorophenyl)-6-(quinolin-6-yl)-1,2,4-triazin-3-amine 30 |
| 31 | 6-(8-Fluoro-4-methylquinolin-6-yl)-5-(2-fluorophenyl)-1,2,4-triazin-3-amine 31 |
| 32 | 5-(4-Fluorophenyl)-6-(8-fluoroquinolin-6-yl)-1,2,4-triazin-3-amine 32 |

| Example No. | Structure and name of the compound |
|---|---|
| 33 | 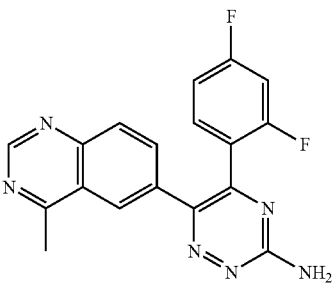<br>5-(2,4-Difluorophenyl)-6-(4-methylquinazolin-6-yl)-1,2,4-triazin-3-amine 33 |
| 34 | 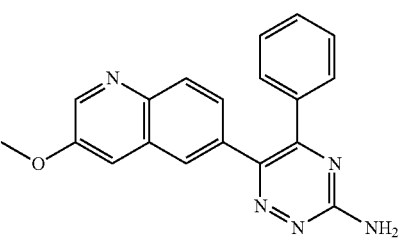<br>6-(3-Methoxyquinolin-6-yl)-5-phenyl-1,2,4-triazin-3-amine 34 |
| 35 | 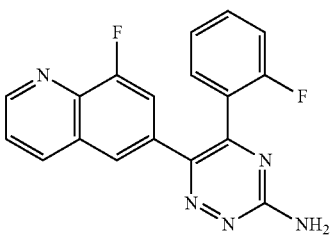<br>5-(2-Fluorophenyl)-6-(8-fluoroquinolin-6-yl)-1,2,4-triazin-3-amine 35 |
| 36 | 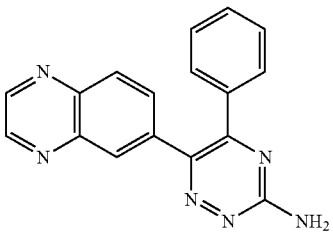<br>5-Phenyl-6-(quinoxalin-6-yl)-1,2,4-triazin-3-amine 36 |
| 37 | 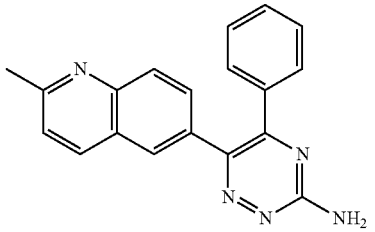<br>6-(2-Methylquinolin-6-yl)-5-phenyl-1,2,4-triazin-3-amine 37 |
| 38 | 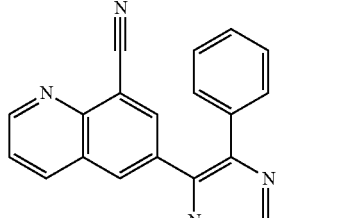<br>6-(3-Amino-5-phenyl-1,2,4-triazin-6-yl)quinoline-8-carbonitrile 38 |
| 39 | 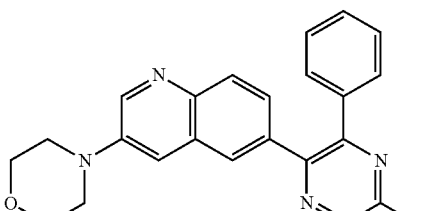<br>6-(3-Morpholinoquinolin-6-yl)-5-phenyl-1,2,4-triazin-3-amine 39 |
| 40 | 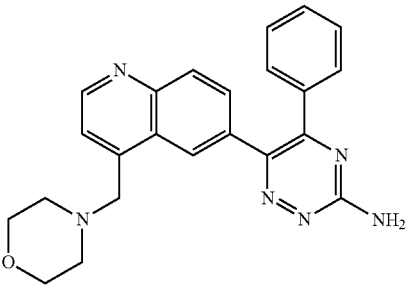<br>6-(4-(Morpholinomethyl)quinolin-6-yl)-5-phenyl-1,2,4-triazin-3-amine 40 |

| Example No. | Structure and name of the compound |
|---|---|
| 41 | 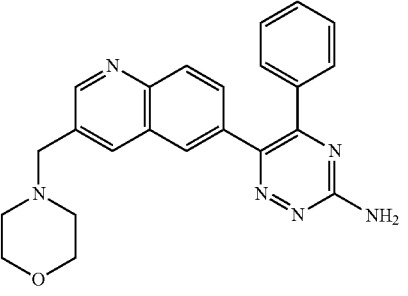

41

6-(3-(Morpholinomethyl)quinolin-6-yl)-5-phenyl-1,2,4-triazin-3-amine 41 |
| 42 | 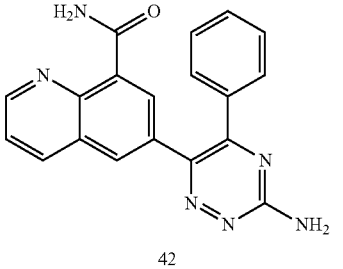 [SMILES: NC(=O)c1cc(-c2nnc(N)nc2-c2ccccc2)cc2cccnc12]

42

6-(3-Amino-5-phenyl-1,2,4-triazin-6-yl)quinoline-8-carboxamide 42 |
| 43 | 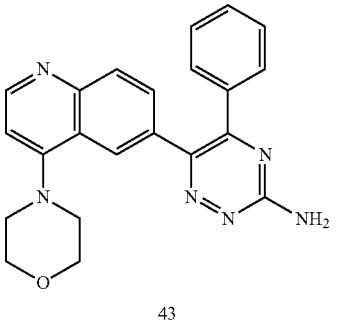 [SMILES: Nc1nnc(-c2ccc3nccc(N4CCOCC4)c3c2)c(-c2ccccc2)n1]

43

6-(4-Morpholinoquinolin-6-yl)-5-phenyl-1,2,4-triazin-3-amine 43 |
| 44 | 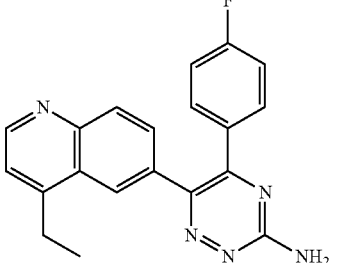

44

6-(4-Ethylquinolin-6-yl)-5-(4-fluorophenyl)-1,2,4-triazin-3-amine 44 |

| Example No. | Structure and name of the compound |
|---|---|
| 45 | 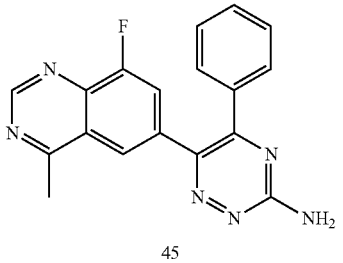 [SMILES: Cc1ncnc2c(F)cc(-c3nnc(N)nc3-c3ccccc3)cc12]

45

6-(8-Fluoro-4-methylquinazolin-6-yl)-5-phenyl-1,2,4-triazin-3-amine 45 |
| 46 | 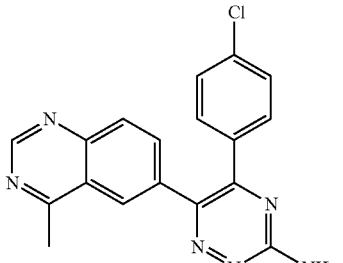

46

5-(4-Chlorophenyl)-6-(4-methylquinazolin-6-yl)-1,2,4-triazin-3-amine 46 |
| 47 | 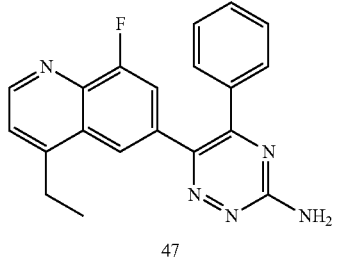 [SMILES: CCc1ccnc2c(F)cc(-c3nnc(N)nc3-c3ccccc3)cc12]

47

6-(4-Ethyl-8-fluoroquinolin-6-yl)-5-phenyl-1,2,4-triazin-3-amine 47 |
| 48 | 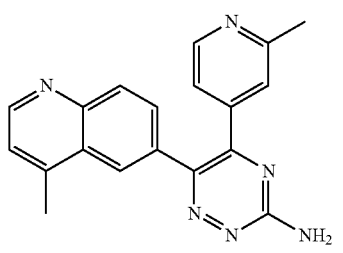

48

5-(2-Methylpyridin-4-yl)-6-(4-methylquinolin-6-yl)-1,2,4-triazin-3-amine 48 |

| Example No. | Structure and name of the compound |
|---|---|
| 49 | 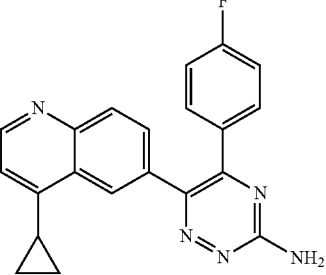<br>6-(4-Cyclopropylquinolin-6-yl)-5-(4-fluorophenyl)-1,2,4-triazin-3-amine 49 |
| 50 | 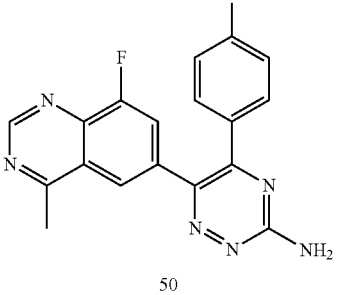<br>6-(8-Fluoro-4-methylquinazolin-6-yl)-5-(4-fluorophenyl)-1,2,4-triazin-3-amine 50 |
| 51 | 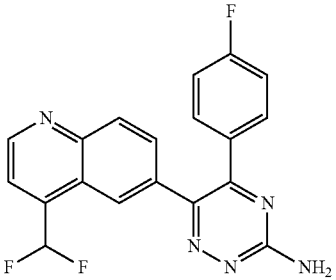<br>6-(4-(Difluoromethyl)quinolin-6-yl)-5-(4-fluorophenyl)-1,2,4-triazin-3-amine 51 |
| 52 | 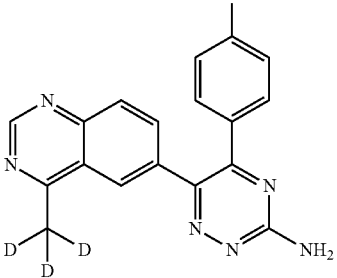<br>5-(4-Fluorophenyl)-6-(4-(methyl-d3)quinazolin-6-yl)-1,2,4-triazin-3-amine 52 |
| 53 | 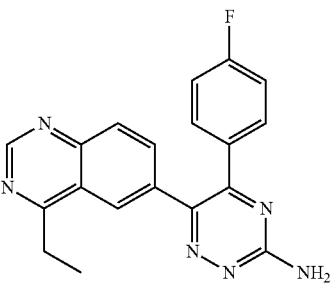<br>6-(4-Ethylquinazolin-6-yl)-5-(4-fluorophenyl)-1,2,4-triazin-3-amine 53 |
| 54 | 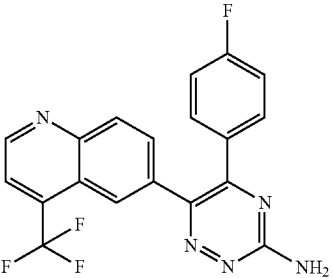<br>5-(4-Fluorophenyl)-6-(4-(trifluoromethyl)quinolin-6-yl)-1,2,4-triazin-3-amine 54 |
| 55 | 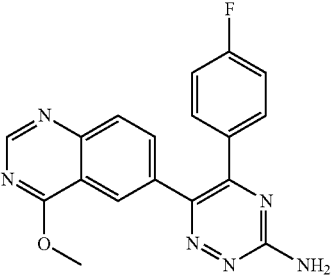<br>5-(4-Fluorophenyl)-6-(4-methoxyquinazolin-6-yl)-1,2,4-triazin-3-amine 55 | or a tautomer, mesomer, racemate, enantiomer, or diastereomer thereof, or a mixture thereof, or a pharmaceutically acceptable salt thereof.

In another aspect, the present invention relates to a method for preparing the compound of formula (I), comprising a step of:

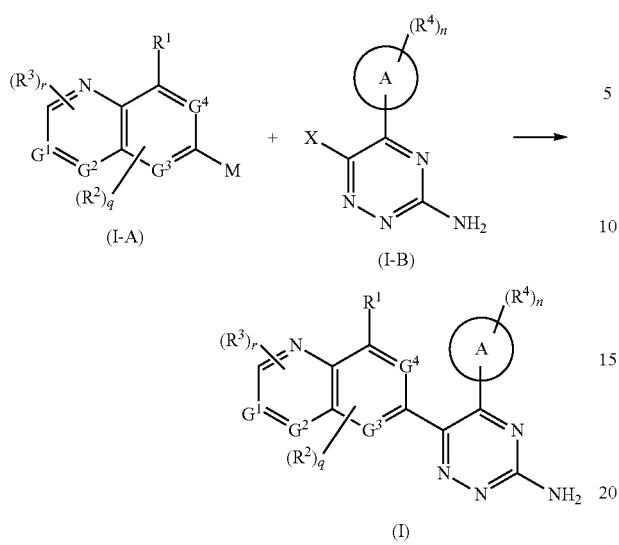

subjecting a compound of formula (I-A) and a compound of formula (I-B) to a coupling reaction to obtain the compound of formula (I), wherein:
X is halogen;
M is

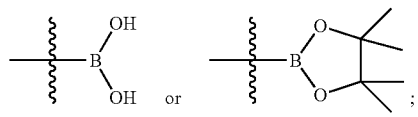

ring A, $G^1$-$G^4$, $R^1$-$R^4$, r, q and n are as defined in formula (I).

In another aspect, the present invention relates to a method for preparing the compound of formula (Iaa), comprising a step of:

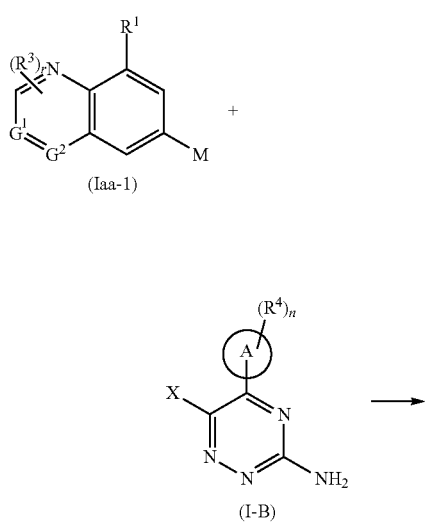

subjecting a compound of formula (Iaa-1) and a compound of formula (I-B) to a coupling reaction to obtain the compound of formula (Iaa), wherein:
X is halogen;
M is

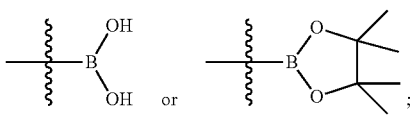

ring A, $G^1$, $G^2$, $R^1$, $R^3$, $R^4$, r and n are as defined in formula (I).

In another aspect, the present invention relates to a method for preparing the compound of formula (II), comprising a step of:

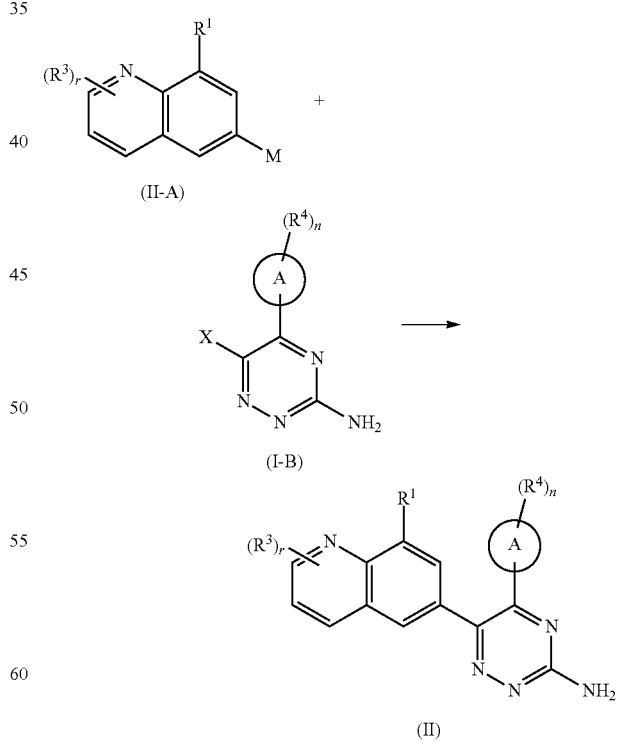

subjecting a compound of formula (II-A) and a compound of formula (I-B) to a coupling reaction to obtain the compound of formula (II), wherein:
X is halogen;
M is

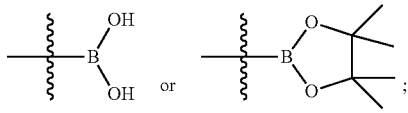

ring A, $R^1$, $R^3$, $R^4$, r and n are as defined in formula (I).

In another aspect, the present invention relates to a method for preparing the compound of formula (III), comprising a step of:

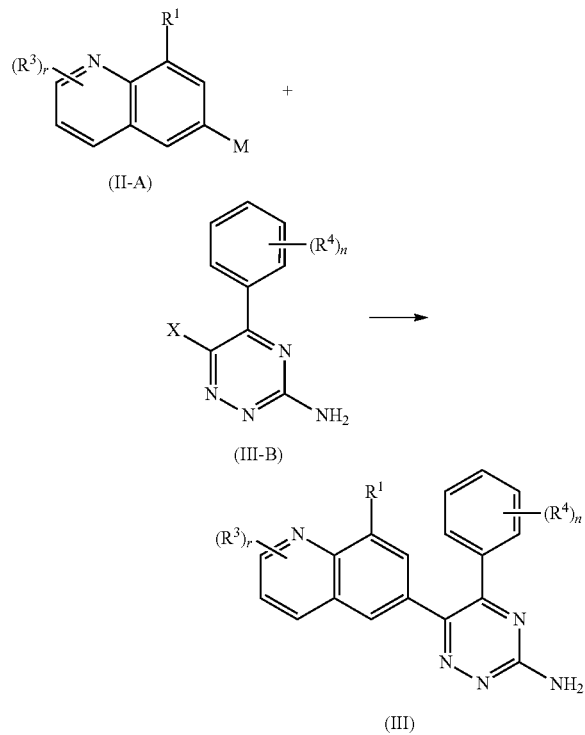

subjecting a compound of formula (II-A) and a compound of formula (III-B) to a coupling reaction to obtain the compound of formula (III),
wherein:
X is halogen;
M is

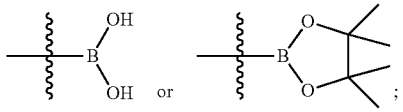

$R^1$, $R^3$, $R^4$, r and n are as defined in formula (I).

In another aspect, the present invention relates to a pharmaceutical composition comprising a therapeutically effective amount of the compound of formula (I), or a tautomer, mesomer, racemate, enantiomer, or diastereomer thereof, or a mixture thereof, or a pharmaceutically acceptable salt thereof, and one or more pharmaceutically acceptable carriers, diluents or excipients.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for treating a disease or condition ameliorated by the inhibition of the $A_{2a}$ receptor.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for treating a disease or condition ameliorated by the inhibition of the $A_{2b}$ receptor.

In the context of the present invention, the disease or condition ameliorated by the inhibition of the $A_{2a}$ receptor or the $A_{2b}$ receptor is selected from the group consisting of cancer, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior; preferably cancer selected from the group consisting of melanoma, brain tumor (glioma with malignant astroglia and oligodendroglioma and the like), esophageal cancer, stomach cancer, liver cancer, pancreatic cancer, colorectal cancer (colon cancer, rectal cancer and the like), lung cancer (non-small cell lung cancer, small cell lung cancer, primary or metastatic squamous carcinoma and the like), kidney cancer, breast cancer, ovarian cancer, prostate cancer, skin cancer, neuroblastoma, sarcoma, osteochondroma, osteoma, osteosarcoma, seminoma, testicular tumor, uterine cancer (cervical cancer, endometrial cancer and the like), head and neck cancer (maxillary cancer, laryngeal cancer, pharyngeal cancer, tongue cancer, intraoral cancer and the like), multiple myeloma, malignant lymphoma (reticular sarcoma, lymphosarcoma, Hodgkin's lymphoma and the like), polycythemia vera, leukemia (acute myeloid leukemia, chronic myeloid leukemia, acute lymphocytic leukemia, chronic lymphocytic leukemia and the like), thyroid tumor, ureteral tumor, bladder tumor, gallbladder cancer, cholangiocarcinoma, chorionic epithelioma, pediatric tumor (Ewing's familial sarcoma, Wilms' sarcoma, rhabdomyosarcoma, angiosarcoma, embryonic testicular cancer, neuroblastoma, retinoblastoma, hepatoblastoma, nephroblastoma and the like) and the like; and more preferably lung cancer.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for treating cancer, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain damage, neuroinflammation and addictive behavior, and preferably cancer.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for treating cancer selected from the group consisting of melanoma, brain tumor (glioma with malignant astroglia and oligodendroglioma and the like), esophageal cancer, stomach cancer, liver cancer, pancreatic cancer, colorectal cancer (colon cancer, rectal cancer and the like), lung cancer (non-small cell lung cancer, small cell lung cancer, primary or metastatic squamous carcinoma and the like), kidney cancer, breast cancer, ovarian cancer, prostate cancer, skin cancer, neuroblastoma, sarcoma, osteochondroma, osteoma, osteosarcoma, seminoma, testicular tumor, uterine cancer (cervical cancer, endometrial cancer and the like), head and neck cancer (maxillary cancer, laryngeal cancer, pharyngeal cancer, tongue cancer, intraoral cancer and the like), multiple myeloma, malignant lymphoma (reticular sarcoma, lymphosarcoma, Hodgkin's lymphoma and the like), polycythemia vera, leukemia (acute myeloid leukemia, chronic myeloid leukemia, acute lymphocytic leukemia, chronic lymphocytic leukemia and the like), thyroid tumor, ureteral tumor, bladder tumor, gallbladder cancer, cholangiocarcinoma, chorionic epithelioma, pediatric tumor (Ewing's familial sarcoma, Wilms' sarcoma, rhabdomyosarcoma, angiosarcoma, embryonic testicular cancer, neuroblastoma, retinoblastoma, hepatoblastoma, nephroblastoma and the like) and the like.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for treating lung cancer, and preferably non-small cell lung cancer.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for inhibiting the $A_{2a}$ receptor.

The present invention further relates to a use of the compound of formula (I), or a tautomer, mesomer, racemate, enantiomer, or diastereomer thereof, or a mixture thereof, or a pharmaceutically acceptable salt thereof, or the pharmaceutical composition comprising the same in the preparation of a medicament for inhibiting the $A_{2b}$ receptor.

The present invention also relates to a method for inhibiting the $A_{2a}$ receptor, comprising a step of administrating to a patient in need thereof a therapeutically effective amount of the compound of formula (I), or a tautomer, mesomer, racemate, enantiomer, or diastereomer thereof, or a mixture thereof, or a pharmaceutically acceptable salt thereof, or the pharmaceutical composition comprising the same.

The present invention also relates to a method for inhibiting the $A_{2b}$ receptor, comprising a step of administrating to a patient in need thereof a therapeutically effective amount of the compound of formula (I), or a tautomer, mesomer, racemate, enantiomer, or diastereomer thereof, or a mixture thereof, or a pharmaceutically acceptable salt thereof, or the pharmaceutical composition comprising the same.

The present invention also relates to a method for treating a disease or condition ameliorated by the inhibition of the Ata receptor, comprising a step of administrating to a patient in need thereof a therapeutically effective amount of the compound of formula (I), or a tautomer, mesomer, racemate, enantiomer, or diastereomer thereof, or a mixture thereof, or a pharmaceutically acceptable salt thereof, or the pharmaceutical composition comprising the same.

The present invention also relates to a method for treating a disease or condition ameliorated by the inhibition of the $A_{2b}$ receptor, comprising a step of administrating to a patient in need thereof a therapeutically effective amount of the compound of formula (I), or a tautomer, mesomer, racemate, enantiomer, a diastereomer thereof, or a mixture thereof, or a pharmaceutically acceptable salt thereof, or the pharmaceutical composition comprising the same.

The present invention relates to a method for treating cancer, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior, and preferably cancer, comprising a step of administrating to a patient in need thereof a therapeutically effective amount of the compound of formula (I), or a tautomer, mesomer, racemate, enantiomer, or diastereomer thereof, or a mixture thereof, or a pharmaceutically acceptable salt thereof, or the pharmaceutical composition comprising the same.

The present invention further relates to a method for treating cancer selected from the group consisting of melanoma, brain tumor (glioma with malignant astroglia and oligodendroglioma and the like), esophageal cancer, stomach cancer, liver cancer, pancreatic cancer, colorectal cancer (colon cancer, rectal cancer and the like), lung cancer (non-small cell lung cancer, small cell lung cancer, primary or metastatic squamous carcinoma and the like), kidney cancer, breast cancer, ovarian cancer, prostate cancer, skin cancer, neuroblastoma, sarcoma, osteochondroma, osteoma, osteosarcoma, seminoma, testicular tumor, uterine cancer (cervical cancer, endometrial cancer and the like), head and neck cancer (maxillary cancer, laryngeal cancer, pharyngeal cancer, tongue cancer, intraoral cancer and the like), multiple myeloma, malignant lymphoma (reticular sarcoma, lymphosarcoma, Hodgkin's lymphoma and the like), polycythemia vera, leukemia (acute myeloid leukemia, chronic myeloid leukemia, acute lymphocytic leukemia, chronic lymphocytic leukemia and the like), thyroid tumor, ureteral tumor, bladder tumor, gallbladder cancer, cholangiocarcinoma, chorionic epithelioma, pediatric tumor (Ewing's familial sarcoma, Wilms' sarcoma, rhabdomyosarcoma, angiosarcoma, embryonic testicular cancer, neuroblastoma, retinoblastoma, hepatoblastoma, nephroblastoma and the like) and the like, comprising a step of administrating to a patient in need thereof a therapeutically effective amount of the compound of formula (I), or a tautomer, mesomer, racemate, enantiomer, or diastereomer thereof, or a mixture thereof, or a pharmaceutically acceptable salt thereof, or the pharmaceutical composition comprising the same.

The present invention further relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use as a medicament.

The present invention also relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use as an $A_{2a}$ receptor antagonist.

The present invention also relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use as an $A_{2b}$ receptor antagonist.

The present invention also relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use in treating a disease or condition ameliorated by the inhibition of the $A_{2a}$ receptor.

The present invention also relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use in treating a disease or condition ameliorated by the inhibition of the $A_{2b}$ receptor.

The present invention also relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use in treating cancer, depression, cognitive function disorder, neurodegenerative disorder (Parkinson's disease, Huntington's disease, Alzheimer's disease or amyotrophic lateral sclerosis and the like), attention-related disorder, extrapyramidal syndrome, abnormal movement disorder, cirrhosis, liver fibrosis, fatty liver, dermal fibrosis, sleep disorder, stroke, brain injury, neuroinflammation and addictive behavior, and preferably cancer.

The present invention further relates to the compound of formula (I), or a tautomer, mesomer, racemate, enantiomer, or diastereomer thereof, or a mixture thereof, or a pharmaceutically acceptable salt thereof, or the pharmaceutical composition comprising the same, for use in treating cancer selected from the group consisting of melanoma, brain tumor (glioma with malignant astroglia and oligodendroglioma and the like), esophageal cancer, stomach cancer, liver cancer, pancreatic cancer, colorectal cancer (colon cancer, rectal cancer and the like), lung cancer (non-small cell lung cancer, small cell lung cancer, primary or metastatic squamous carcinoma and the like), kidney cancer, breast cancer, ovarian cancer, prostate cancer, skin cancer, neuroblastoma, sarcoma, osteochondroma, osteoma, osteosarcoma, seminoma, testicular tumor, uterine cancer (cervical cancer, endometrial cancer and the like), head and neck cancer (maxillary cancer, laryngeal cancer, pharyngeal cancer, tongue cancer, intraoral cancer and the like), multiple myeloma, malignant lymphoma (reticular sarcoma, lymphosarcoma, Hodgkin's lymphoma and the like), polycythemia vera, leukemia (acute myeloid leukemia, chronic myeloid leukemia, acute lymphocytic leukemia, chronic lymphocytic leukemia and the like), thyroid tumor, ureteral tumor, bladder tumor, gallbladder cancer, cholangiocarcinoma, chorionic epithelioma, pediatric tumor (Ewing's familial sarcoma, Wilms' sarcoma, rhabdomyosarcoma, angiosarcoma, embryonic testicular cancer, neuroblastoma, retinoblastoma, hepatoblastoma, nephroblastoma and the like) and the like.

Pharmaceutical compositions containing the active ingredient can be in a form suitable for oral administration, for example, a tablet, troche, lozenge, aqueous or oily suspension, dispersible powder or granule, emulsion, hard or soft capsule, syrup or elixir. Oral compositions can be prepared according to any known method in the art for the preparation of pharmaceutical composition. Such composition can contain one or more ingredients selected from the group consisting of sweeteners, flavoring agents, colorants and preservatives, in order to provide a pleasing and palatable pharmaceutical preparation. Tablets contain the active ingredient in admixture with nontoxic pharmaceutically acceptable excipients suitable for the manufacture of tablets.

An aqueous suspension contains the active ingredient in admixture with excipients suitable for the manufacture of an aqueous suspension. The aqueous suspension can also contain one or more preservatives such as ethyl paraben or n-propyl paraben, one or more colorants, one or more flavoring agents, and one or more sweeteners.

An oil suspension can be formulated by suspending the active ingredient in a vegetable oil. The oil suspension can contain a thickener. The aforementioned sweeteners and flavoring agents can be added to provide a palatable formulation.

The active ingredient in admixture with the dispersants or wetting agents, suspending agent or one or more preservatives can be prepared as a dispersible powder or granule suitable for the preparation of an aqueous suspension by adding water. Suitable dispersants or wetting agents and suspending agents are exemplified by those already mentioned above. Additional excipients, such as sweeteners, flavoring agents and colorants, can also be added. These compositions can be preserved by adding an antioxidant, such as ascorbic acid.

The pharmaceutical composition of the present invention can also be in the form of an oil-in-water emulsion.

The pharmaceutical composition can be in the form of a sterile injectable aqueous solution. Acceptable vehicles or solvents that can be used are water, Ringer's solution or isotonic sodium chloride solution. The sterile injectable formulation can be a sterile injectable oil-in-water microemulsion in which the active ingredient is dissolved in the oil phase. For example, the active ingredient is dissolved in a mixture of soybean oil and lecithin. The oil solution is then added into a mixture of water and glycerol, and processed to form a micro-emulsion. The injectable solution or microemulsion can be introduced into a patient's bloodstream by local bolus injection. Alternatively, the solution and microemulsion are preferably administrated in a manner that maintains a constant circulating concentration of the compound of the present invention. In order to maintain this constant concentration, a continuous intravenous delivery device can be used. An example of such a device is Deltec CADD-PLUS. TM. 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium.

The compound of the present invention can be administrated in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug. Such materials include cocoa butter, glycerin gelatin, hydrogenated vegetable oils, mixtures of polyethylene glycols with various molecular weights and fatty acid esters of polyethylene glycols.

It is well known to those skilled in the art that the dosage of a drug depends on a variety of factors including but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently optionally selected from the group consisting of H atom, D atom, halogen, alkyl, alkoxy, haloalkyl, hydroxy, hydroxyalkyl, cyano, amino, nitro, cycloalkyl, heterocyclyl, aryl and heteroaryl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of H atom, D atom, halogen, alkyl, alkoxy, haloalkyl, hydroxy, hydroxyalkyl, cyano, amino, nitro, cycloalkyl, heterocyclyl, aryl and heteroaryl.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, more preferably, 3 to 10 ring atoms wherein 1 to 4 atoms are heteroatoms, and more preferably 5 to 6 ring atoms wherein 1 to 3 atoms are heteroatoms. Non-limiting examples of monocyclic heterocyclyl include pyrrolidinyl, tetrahydropyranyl, 1,2,3,6-tetrahydropyridyl, piperidinyl, piperazinyl, morpholinyl, thiomorpholinyl, homopiperazinyl and the like. Polycyclic heterocyclyl includes a heterocyclyl having a spiro ring, fused ring or bridged ring.

The ring of heterocyclyl can be fused to the ring of aryl, heteroaryl or cycloalkyl, wherein the ring bound to the parent structure is heterocyclyl. Non-limiting examples thereof include:

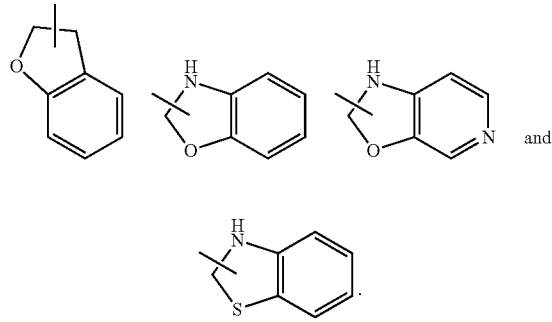

The heterocyclyl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term "aryl" refers to a 6 to 14 membered all-carbon monocyclic ring or polycyclic fused ring (i.e., each ring in the system shares an adjacent pair of carbon atoms with another ring in the system) having a conjugated π-electron system, preferably 6 to 10 membered aryl, for example, phenyl and naphthyl. The ring of aryl can be fused to the ring of heteroaryl, heterocyclyl or cycloalkyl, wherein the ring bound to the parent structure is aryl ring. Non-limiting examples thereof include:

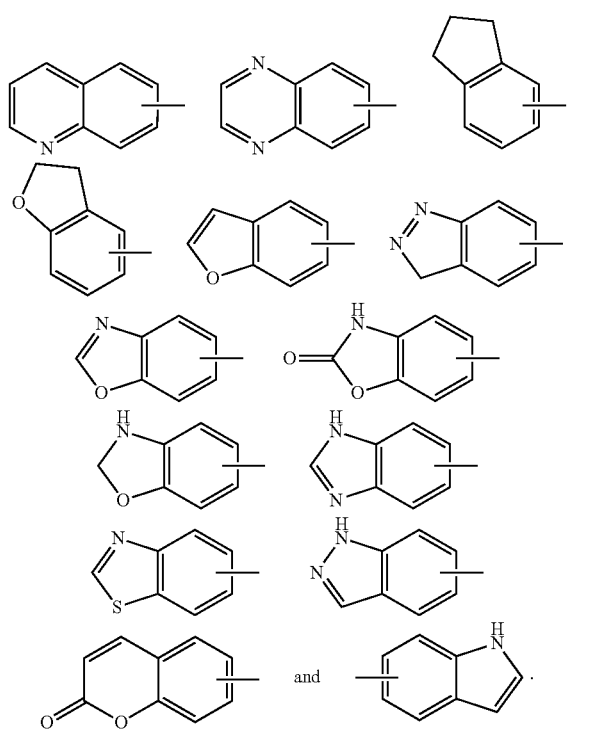

The aryl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term "heteroaryl" refers to a 5 to 14 membered heteroaromatic system having 1 to 4 heteroatoms selected from the group consisting of O, S and N. The heteroaryl is preferably 5 to 10 membered heteroaryl, more preferably 5 or 6 membered heteroaryl, for example, furanyl, thienyl, pyridyl, pyrrolyl, N-alkylpyrrolyl, pyrimidinyl, pyrazinyl, pyridazinyl, imidazolyl, pyrazolyl, tetrazolyl and the like. The ring of heteroaryl can be fused to the ring of aryl, heterocyclyl or cycloalkyl, wherein the ring bound to the parent structure is heteroaryl ring. Non-limiting examples thereof include:

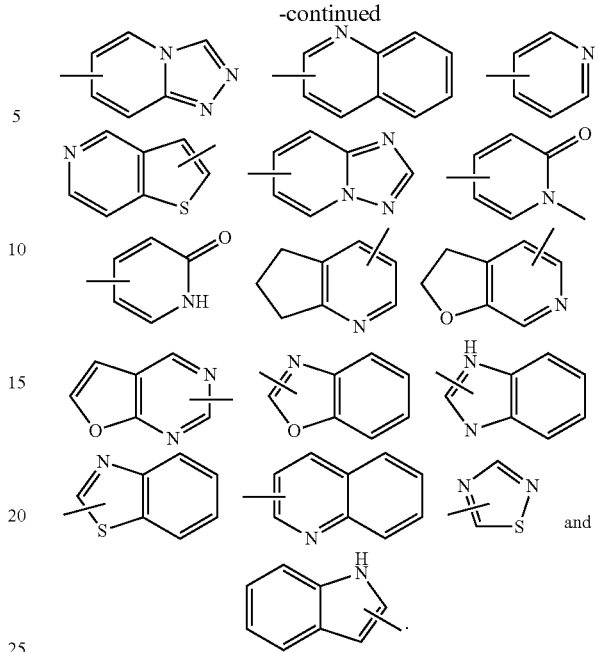

The heteroaryl can be substituted or unsubstituted. When substituted, the substituent group(s) can be substituted at any available connection point. The substituent group(s) is preferably one or more group(s) independently optionally selected from the group consisting of hydrogen, halogen, alkyl, alkoxy, haloalkyl, hydroxy, hydroxyalkyl, cyano, amino, nitro, cycloalkyl, heterocyclyl, aryl and heteroaryl.

The term "haloalkyl" refers to an alkyl group substituted by one or more halogens, wherein the alkyl is as defined above.

The term "deuterated alkyl" refers to an alkyl group substituted by one or more deuterium atoms, wherein the alkyl is as defined above.

The term "hydroxy" refers to an —OH group.

The term "hydroxyalkyl" refers to an alkyl group substituted by hydroxy(s), wherein the alkyl is as defined above.

The term "halogen" refers to fluorine, chlorine, bromine or iodine.

The term "hydroxy" refers to an —OH group.

The term "amino" refers to a —NH$_2$ group.

The term "cyano" refers to a —CN group.

The term "nitro" refers to a —NO$_2$ group.

The term "carbonyl" refers to a C=O group.

The term "carboxy" refers to a —C(O)OH group.

The term "carboxylate group" refers to a —C(O)O(alkyl) group or a —C(O)O(cycloalkyl) group, wherein the alkyl and cycloalkyl are as defined above.

The term "acyl halide" refers to a compound containing a —C(O)-halogen group.

The present invention also comprises the compounds of formula (I) in various deuterated forms. Each of the available hydrogen atoms attached to the carbon atom can be independently replaced by a deuterium atom. Those skilled in the art can synthesize a compound of formula (I) in a deuterated form with reference to the relevant literature. Commercially available deuterated starting materials can be employed in the preparation of the compound of formula (I) in deuterated form, or they can be synthesized by conventional techniques with deuterated reagents including, but not limited to, deuterated borane, trideuterated borane in tetrahydrofuran, deuterated lithium aluminum hydride, deuterated iodoethane, deuterated iodomethane and the like.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following technical solutions:

Scheme I

A method for preparing the compound of formula (I) of the present invention or a tautomer, mesomer, racemate, enantiomer, or diastereomer thereof, or a mixture thereof, or a pharmaceutically acceptable salt thereof, comprises the following steps of:

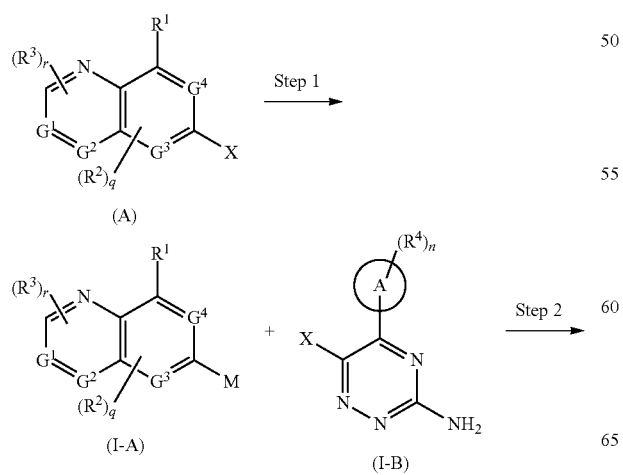

in Step 1, a compound of formula (A) is reacted with boric acid or a borate compound in the presence of a catalyst under an alkaline condition to obtain a compound of formula (I-A);

in Step 2, the compound of formula (I-A) is reacted with a compound of formula (I-B) in the presence of a catalyst under an alkaline condition to obtain the compound of formula (I).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, tetratriphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Wherein:

X is halogen;

M is

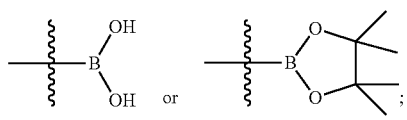

ring A, $G^1$-$G^4$, $R^1$-$R^4$, r, q and n are as defined in formula (I).

Scheme II

A method for preparing the compound of formula (Iaa) of the present invention or a tautomer, mesomer, racemate, enantiomer, or diastereomer thereof, or a mixture thereof, or a pharmaceutically acceptable salt thereof, comprises the following steps of:

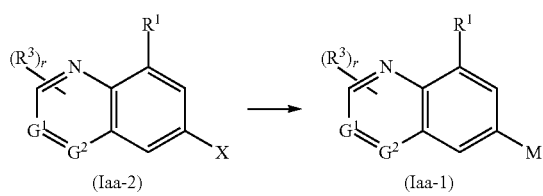

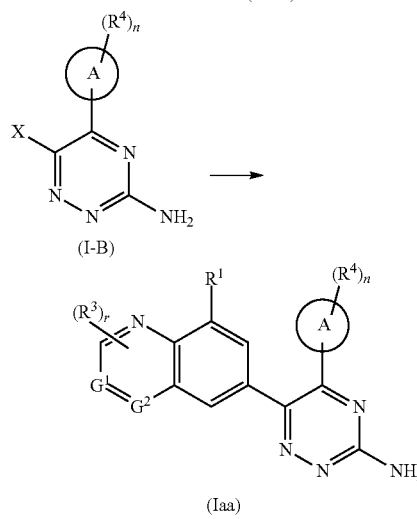

in Step 1, a compound of formula (Iaa-2) is reacted with boric acid or a borate compound in the presence of a catalyst under an alkaline condition to obtain a compound of formula (Iaa-1);

in Step 2, the compound of formula (Iaa-1) is reacted with a compound of formula (I-B) in the presence of a catalyst under an alkaline condition to obtain the compound of formula (Iaa).
Wherein:
X is halogen;
M is

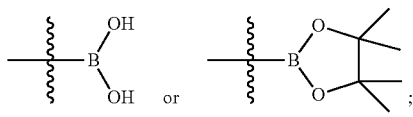

ring A, $G^1$, $G^2$, $R^1$, $R^3$, $R^4$, r and n are as defined in formula (I).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, tetratriphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Scheme III

A method for preparing the compound of formula (Ibb) of the present invention or a tautomer, mesomer, racemate, enantiomer, or diastereomer thereof, or a mixture thereof, or a pharmaceutically acceptable salt thereof, comprises the following steps of:

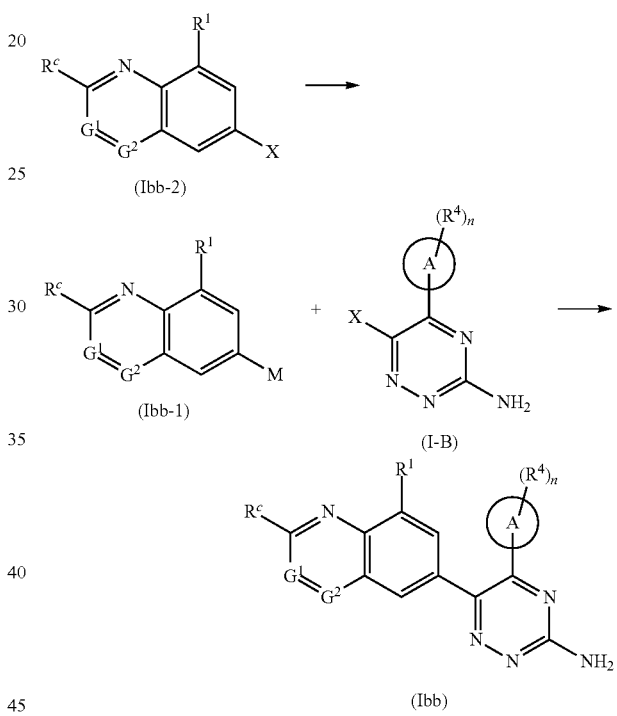

in Step 1, a compound of formula (Ibb-2) is reacted with boric acid or a borate compound in the presence of a catalyst under an alkaline condition to obtain a compound of formula (Ibb-1);

in Step 2, the compound of formula (Ibb-1) is reacted with a compound of formula (I-B) in the presence of a catalyst under an alkaline condition to obtain the compound of formula (Ibb).
Wherein:
X is halogen;
M is

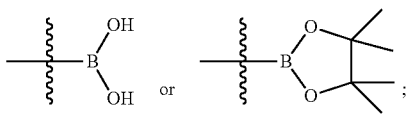

ring A, $G^1$, $G^2$, $R^1$, $R^3$, $R^4$, r and n are as defined in formula (I).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, tetratriphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Scheme IV

A method for preparing the compound of formula (II) of the present invention or a tautomer, mesomer, racemate, enantiomer, or diastereomer thereof, or a mixture thereof, or a pharmaceutically acceptable salt thereof, comprises the following steps of:

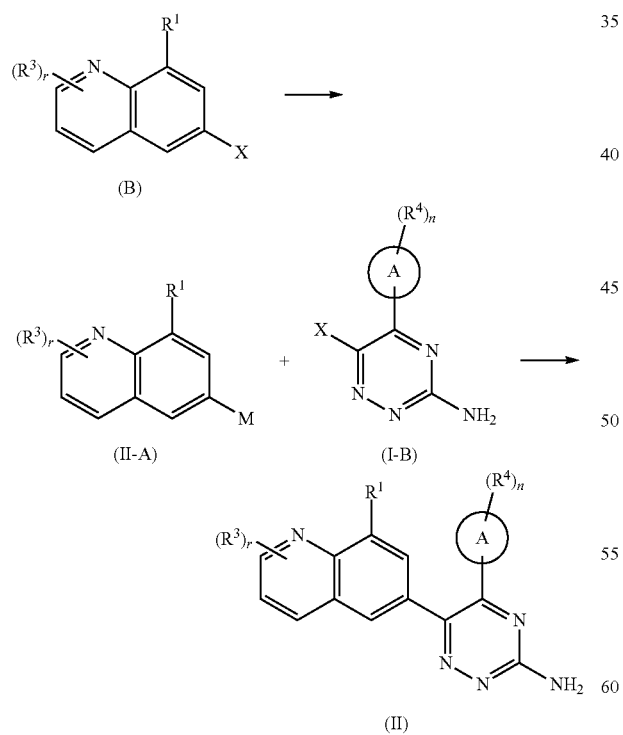

in Step 1, a compound of formula (B) is reacted with boric acid or a borate compound in the presence of a catalyst under an alkaline condition to obtain a compound of formula (II-A);

in Step 2, the compound of formula (II-A) is reacted with a compound of formula (I-B) in the presence of a catalyst under an alkaline condition to obtain the compound of formula (II).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, tetratriphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Wherein:
X is halogen;
M is

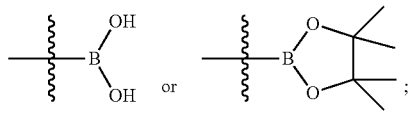

ring A, $R^1$, $R^3$, $R^4$, r and n are as defined in formula (I).

Scheme V

A method for preparing the compound of formula (III) of the present invention or a tautomer, mesomer, racemate, enantiomer, or diastereomer thereof, or a mixture thereof, or a pharmaceutically acceptable salt thereof, comprises the following steps of:

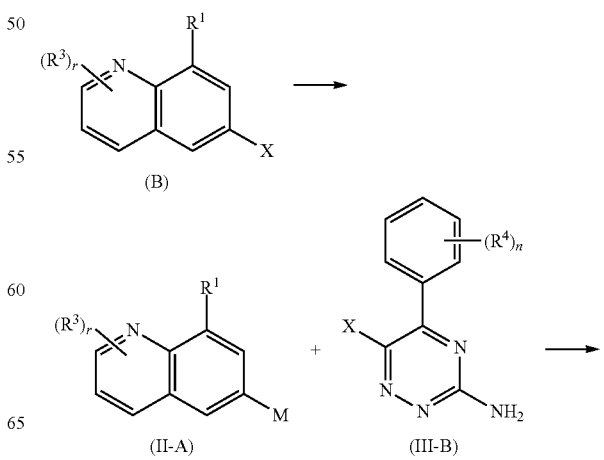

-continued

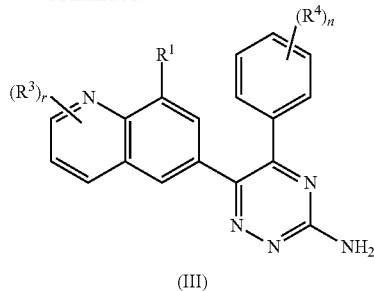

(III)

in Step 1, a compound of formula (B) is reacted with boric acid or a borate compound in the presence of a catalyst under an alkaline condition to obtain a compound of formula (II-A);

in Step 2, the compound of formula (II-A) is reacted with a compound of formula (III-B) in the presence of a catalyst under an alkaline condition to obtain the compound of formula (III).

The reagent that provides an alkaline condition includes organic bases and inorganic bases. The organic bases include, but are not limited to, triethylamine, N,N-diisopropylethylamine, n-butyllithium, lithium diisopropylamide, lithium bis(trimethylsilyl)amine, potassium acetate, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide.

The catalyst includes, but is not limited to, Pd/C, tetratriphenylphosphine palladium, palladium dichloride, palladium acetate, bis(dibenzylideneacetone)palladium, chloro(2-dicyclohexylphosphino-2',4',6'-triisopropyl-1,1'-biphenyl)[2-(2'-amino-1,1'-biphenyl)]palladium, [1,1'-bis(diphenylphosphino)ferrocene]dichloropalladium, 1,1'-bis(dibenzylphosphoryl)ferrocene palladium dichloride and tris(dibenzylideneacetone)dipalladium, and preferably [1,1'-bis(diphenylphosphino)ferrocene]dichloropalladium.

The above reactions are preferably carried out in a solvent. The solvent used includes, but is not limited to, acetic acid, methanol, ethanol, n-butanol, toluene, tetrahydrofuran, dichloromethane, petroleum ether, ethyl acetate, n-hexane, dimethyl sulfoxide, 1,4-dioxane, glycol dimethyl ether, water, N,N-dimethylformamide, and mixtures thereof.

Wherein:
X is halogen;
M is

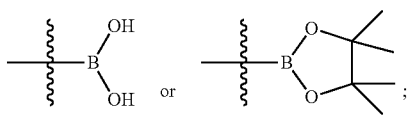

$R^1$, $R^3$, $R^4$, r and n are as defined in formula (I).

PREFERRED EMBODIMENTS

The present invention will be further described with reference to the following examples, but the examples should not be considered as limiting the scope of the present invention.

EXAMPLES

The structures of the compounds were identified by nuclear magnetic resonance (NMR) and/or mass spectrometry (MS). NMR shifts (δ) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) was determined on an Agilent HPLC 1200DAD, Agilent HPLC 1200VWD and Waters HPLC e2695-2489 high pressure liquid chromatographs.

Chiral HPLC was determined on an Agilent 1260 DAD high performance liquid chromatograph.

High performance liquid preparation was carried out on Waters 2767, Waters 2767-SQ Detecor2, Shimadzu LC-20AP and Gilson-281 preparative chromatographs.

Chiral preparation was carried out on a Shimadzu LC-20AP preparative chromatograph.

CombiFlash rapid preparation instrument used was Combiflash Rf200 (TELEDYNE ISCO).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for silica gel column chromatography.

Prep Star SD-1 (Varian Instruments Inc.) or SFC-multigram (Berger Instruments Inc.) was used for chiral preparative column chromatography.

The average kinase inhibition rates and IC$_{50}$ values were determined by a NovoStar ELISA (BMG Co., Germany).

The known starting materials of the present invention can be prepared by the known methods in the art, or can be purchased from ABCR GmbH & Co. KG Acros Organnics, Aldrich Chemical Company, Accela ChemBio Inc., or Dari chemical Company, etc.

Unless otherwise stated, the reactions were carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, with the above operation was repeated three times.

CEM Discover-S 908860 type microwave reactor was used in microwave reactions.

Unless otherwise stated, the solution refers to an aqueous solution.

Unless otherwise stated, the reaction temperature is room temperature from 20° C. to 30° C.

The reaction process in the examples was monitored by thin layer chromatography (TLC). The developing solvent used in the reactions, the eluent system in column chromatography and the developing solvent system in thin layer chromatography for purification of the compounds included: A: dichloromethane/methanol system, B: n-hexane/ethyl acetate system, C: petroleum ether/ethyl acetate system, and D: dichloromethane/ethyl acetate/methanol system. The ratio of the volume of the solvent was adjusted according to the polarity of the compounds, and a small quantity of alkaline reagent such as triethylamine or acidic reagent such as acetic acid can also be added for adjustment.

Example 1

6-(8-Methylquinolin-6-yl)-5-phenyl-1,2,4-triazin-3-amine

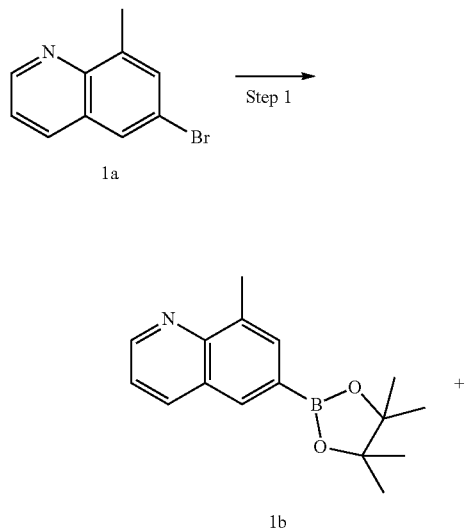

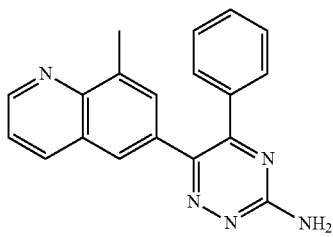

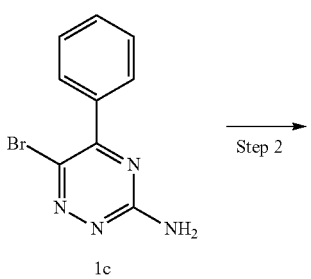

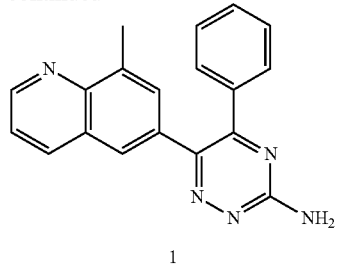

Step 1

8-Methyl-6-(4,4,5,5-tetramethyl-1,3,2-dioxaborolan-2-yl)quinoline 1b

6-Bromo-8-methylquinoline 1a (444 mg, 2.00 mmol, prepared according to the known method disclosed in "*Journal of Organic Chemistry*, 2014, 79(11), 5379-5385"), bis(pinacolato)diboron (508 mg, 2.00 mmol), [1,1'-bis(diphenylphosphino)ferrocene]dichloropalladium (292 mg, 0.40 mmol) and potassium acetate (588 mg, 6.00 mmol) were dissolved successively in 10 mL of glycol dimethyl ether under an argon atmosphere. The reaction solution was heated to 80° C., and stirred for 12 hours. The reaction was stopped, and the reaction solution was cooled to room temperature and filtrated. The filtrate was added with 20 mL of ethyl acetate, washed with water (10 mL) and saturated sodium chloride solution (10 mL) successively, dried over anhydrous sodium sulfate, and filtrated. The filtrate was concentrated under reduced pressure, and the residue was purified by thin layer chromatography with developing solvent system B to obtain the title product 1b (320 mg), yield: 59.5%.

MS m/z (ESI): 270.1 [M+1].

Step 2

6-(8-Methylquinolin-6-yl)-5-phenyl-1,2,4-triazin-3-amine 1

Compound 1b (54 mg, 0.20 mmol), 6-bromo-5-phenyl-1,2,4-triazin-3-amine 1c (50 mg, 0.20 mmol, prepared according to the known method disclosed in "*Journal of Medicinal Chemistry*, 2012, 55(5), 1898-1903"), [1,1'-bis(diphenylphosphino)ferrocene]dichloropalladium (29 mg, 0.04 mmol) and potassium carbonate (82 mg, 0.60 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was added with 20 mL of ethyl acetate, washed with water (10 mL) and saturated sodium chloride solution (10 mL) successively, dried over anhydrous sodium sulfate, and filtrated. The filtrate was concentrated under reduced pressure, and the residue was purified by high performance liquid chromatography with developing solvent system A to obtain the title product 1 (20 mg), yield: 32.2%.

MS m/z (ESI): 314.4 [M+1].

$^1$H NMR (400 MHz, DMSO-d$_6$) δ 8.92 (m, 1H), 8.22-8.24 (d, 1H), 7.80 (s, 1H), 7.57 (s, 1H), 7.50-7.51 (m, 3H), 7.43-7.45 (m, 3H), 7.33-7.35 (m, 2H), 2.62 (s, 3H).

Example 2

6-(8-Fluoroquinolin-6-yl)-5-phenyl-1,2,4-triazin-3-amine 2

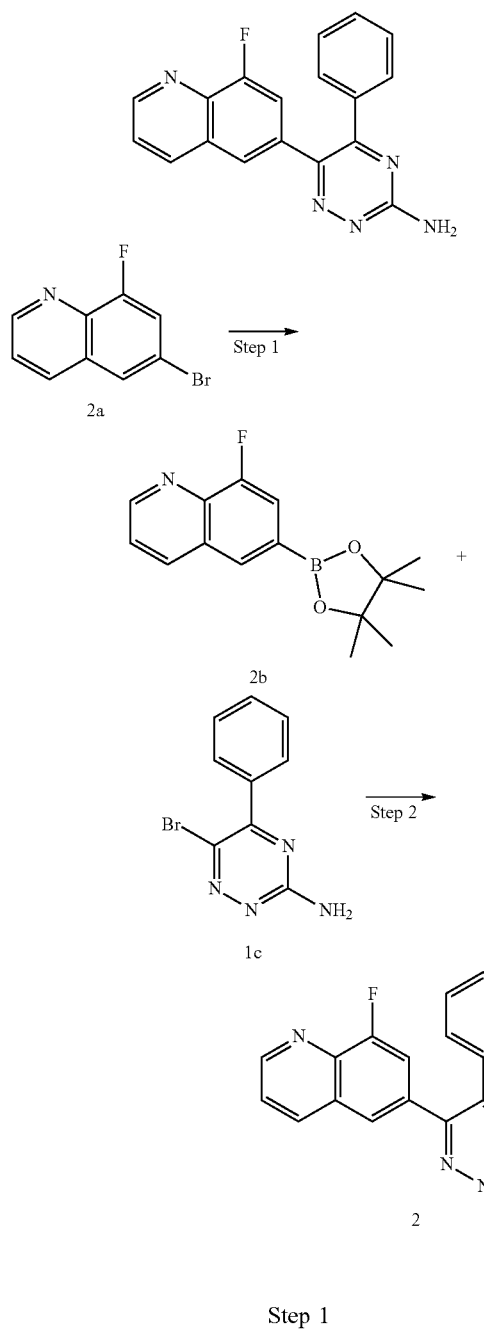

Step 1

8-Fluoro-6-(4,4,5,5-tetramethyl-1,3,2-dioxaborolan-2-yl)quinoline 2b

6-Bromo-8-fluoroquinoline 2a (226 mg, 1.00 mmol), bis(pinacolato)diboron (305 mg, 1.20 mmol), [1,1'-bis(diphenylphosphino)ferrocene]dichloropalladium (146 mg, 0.20 mmol) and potassium acetate (294 mg, 3.00 mmol) were dissolved successively in 10 mL of glycol dimethyl ether under an argon atmosphere. The reaction solution was heated to 80° C., and stirred for 12 hours. The reaction was stopped, and the reaction solution was cooled to room temperature and filtrated. The filtrate was concentrated under reduced pressure, and the residue was purified by CombiFlash rapid preparation instrument with elution system B to obtain the title product 2b (220 mg), yield: 80.1%.

MS m/z (ESI): 274.1 [M+1].

Step 2

6-(8-Fluoroquinolin-6-yl)-5-phenyl-1,2,4-triazin-3-amine 2

Compound 2b (109 mg, 0.40 mmol), compound 1c (100 mg, 0.40 mmol), [1,1'-bis(diphenylphosphino)ferrocene]dichloropalladium (58 mg, 0.08 mmol) and potassium carbonate (156 mg, 1.20 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 2 (20 mg), yield: 15.9%.

MS m/z (ESI): 318.4 [M+1].

$^1$H NMR (400 MHz, DMSO-$d_6$) δ 8.95 (m, 1H), 8.38-8.40 (d, 1H), 7.91 (s, 1H), 7.58-7.62 (m, 3H), 7.41-7.46 (m, 4H), 7.35-7.37 (m, 2H).

Example 3

5-Phenyl-6-(quinolin-6-yl)-1,2,4-triazin-3-amine

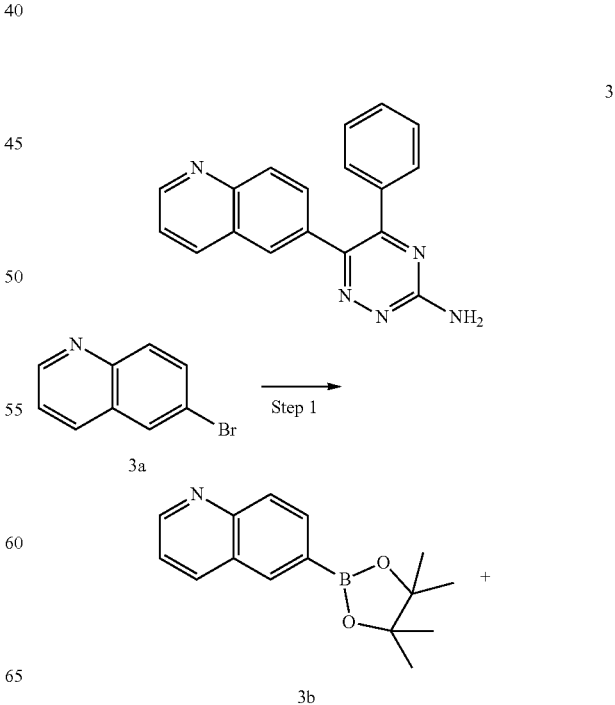

47
-continued

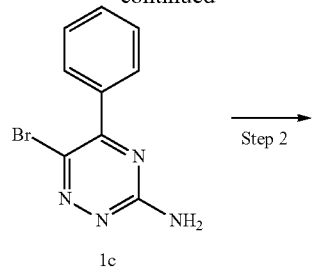
1c

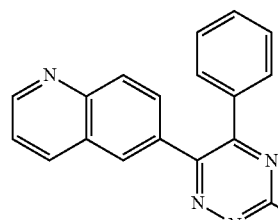
3

Step 1

6-(4,4,5,5-Tetramethyl-1,3,2-dioxaborolan-2-yl)quinoline 3b

6-Bromoquinoline 3a (1.0 g, 4.80 mmol, Accela ChemBio Inc.), bis(pinacolato)diboron (1.46 g, 5.76 mmol), [1,1'-bis(diphenylphosphino)ferrocene]dichloropalladium (0.7 g, 0.96 mmol) and potassium acetate (1.4 g, 14.40 mmol) were dissolved successively in 20 mL of glycol dimethyl ether under an argon atmosphere. The reaction solution was heated to 80° C., and stirred for 12 hours. The reaction was stopped, and the reaction solution was cooled to room temperature and filtrated. The filtrate was concentrated under reduced pressure, and the residue was purified by CombiFlash rapid preparation instrument with elution system B to obtain the title product 3b (1.2 g), yield: 98.4%.

MS m/z (ESI): 256.1 [M+1].

Step 2

5-Phenyl-6-(quinolin-6-yl)-1,2,4-triazin-3-amine 3

Compound 3b (203 mg, 0.80 mmol), compound 1c (200 mg, 0.80 mmol), [1,1'-bis(diphenylphosphino)ferrocene]dichloropalladium (116 mg, 0.16 mmol) and potassium carbonate (330 mg, 2.40 mmol) were dissolved successively in 24 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 3 (100 mg), yield: 42.0%.

MS m/z (ESI): 300.4 [M+1].

¹H NMR (400 MHz, DMSO-d₆) δ 8.90-8.91 (m, 1H), 8.32-8.34 (d, 1H), 8.10 (s, 1H), 7.89-7.91 (d, 1H), 7.52-7.59 (m, 4H), 7.43-7.44 (m, 3H), 7.33-7.35 (m, 2H).

48

Example 4

6-(8-Chloroquinolin-6-yl)-5-phenyl-1,2,4-triazin-3-amine

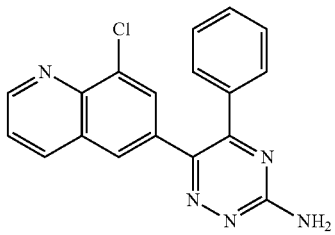
4

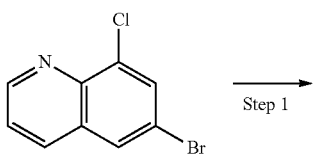
4a

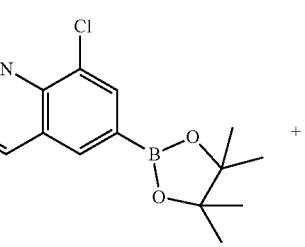
4b

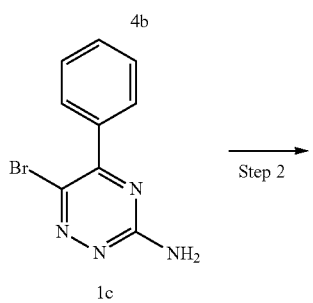
1c

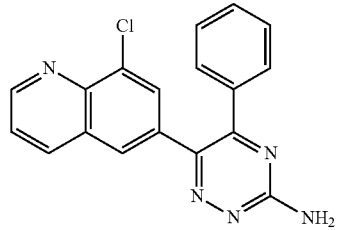
4

Step 1

8-Chloro-6-(4,4,5,5-tetramethyl-1,3,2-dioxaborolan-2-yl)quinoline 4b

6-Bromo-8-chloroquinoline 4a (300 mg, 1.24 mmol), bis(pinacolato)diboron (378 mg, 1.49 mmol), [1,1'-bis(diphenylphosphino)ferrocene]dichloropalladium (181 mg, 0.25 mmol) and potassium acetate (364 mg, 3.72 mmol) were dissolved successively in 50 mL of glycol dimethyl ether under an argon atmosphere. The reaction solution was heated to 80° C., and stirred for 12 hours. The reaction was stopped, and the reaction solution was cooled to room temperature and filtrated. The filtrate was concentrated under reduced pressure, and the residue was purified by CombiFlash rapid preparation instrument with elution system B to obtain the title product 4b (260 mg), yield: 72.6%.

MS m/z (ESI): 290.5 [M+1].

Step 2

6-(8-Chloroquinolin-6-yl)-5-phenyl-1,2,4-triazin-3-amine 4

Compound 4b (127 mg, 0.44 mmol), compound 1c (100 mg, 0.40 mmol), [1,1'-bis(diphenylphosphino)ferrocene]dichloropalladium (58 mg, 0.08 mmol) and potassium carbonate (165 mg, 1.20 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature, added with 20 mL of ethyl acetate, washed with saturated sodium chloride solution (10 mL), dried over anhydrous sodium sulfate, and filtrated. The filtrate was concentrated under reduced pressure, and the residue was purified by CombiFlash rapid preparation instrument with elution system A to obtain the title product 4 (30 mg), yield: 20.5%.

MS m/z (ESI): 334.4 [M+1].

$^1$H NMR (400 MHz, DMSO-$d_6$) δ 9.01-9.02 (m, 1H), 8.39-8.41 (d, 1H), 8.05 (s, 1H), 7.80 (s, 1H), 7.59-7.66 (m, 3H), 7.44-7.47 (m, 3H), 7.36-7.38 (m, 2H).

Example 5

5-(5-Methylfuran-2-yl)-6-(8-methylquinolin-6-yl)-1,2,4-triazin-3-amine

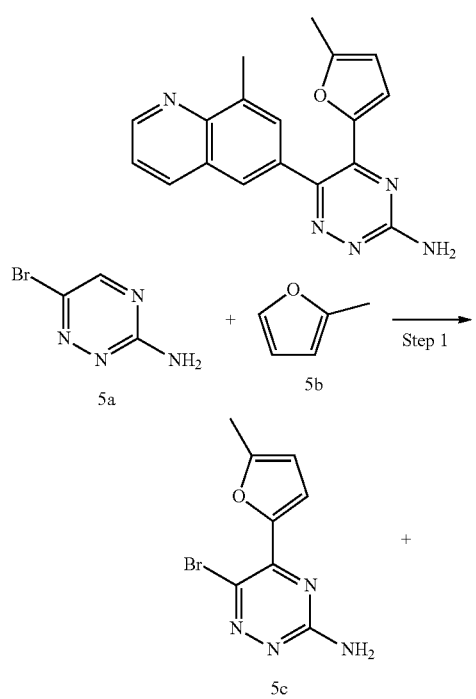

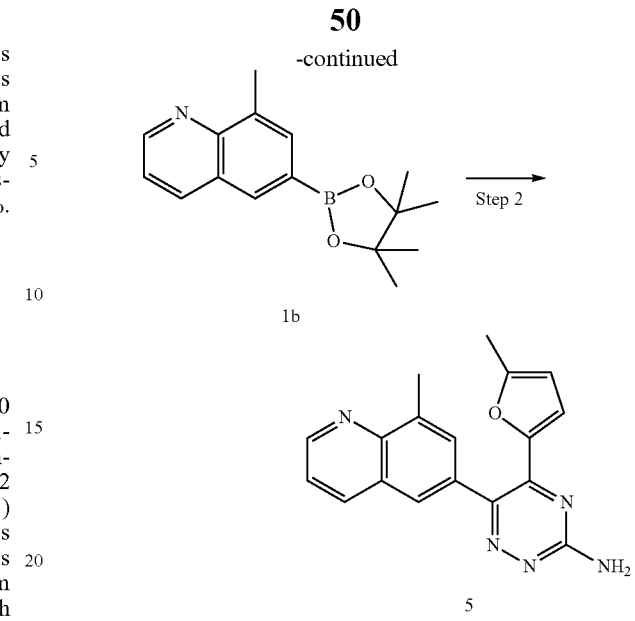

Step 1

6-Bromo-5-(5-methylfuran-2-yl)-1,2,4-triazin-3-amine 5c

6-Bromo-1,2,4-triazin-3-amine 5a (1.0 g, 5.72 mmol, prepared according to the known method disclosed in "*Journal of the American Chemical Society*, 2015, 137(26), 8388-8391"), 6 mL of trifluoroacetic acid and 6 mL of dichloromethane were added to a reaction flask. The reaction solution was added with 2-methylfuran 5b (567 μL, 6.29 mmol), and stirred at room temperature for 17 hours. The reaction was stopped, and the reaction solution was added dropwise with saturated sodium bicarbonate solution to adjust the pH>7. The reaction solution was added with 30 mL of a pre-prepared aqueous solution of potassium hydroxide (962 mg, 17.14 mmol) and potassium hexacyanoferrate (5.65 g, 17.14 mmol), and stirred at room temperature for 1 hour. The reaction was stopped, and the reaction solution was extracted with ethyl acetate (150 mL×3). The organic phases were combined, added with silica gel, and concentrated under reduced pressure. The residue was purified by CombiFlash rapid preparation instrument with elution system C to obtain the title product 5c (450 mg), yield: 30.9%.

MS m/z (ESI): 257.3 [M+1].

Step 2

5-(5-Methylfuran-2-yl)-6-(8-methylquinolin-6-yl)-1,2,4-triazin-3-amine 5

Compound 5c (80 mg, 0.31 mmol), compound 1b (127 mg, 0.47 mmol), [1,1'-bis(diphenylphosphino)ferrocene]dichloropalladium (23 mg, 0.031 mmol) and potassium carbonate (173 mg, 1.25 mmol) were dissolved successively in 12 mL of a mixed solution of 1,4-dioxane and water (V/V=5:1) under an argon atmosphere. The reaction solution was heated to 90° C., and stirred for 2 hours. The reaction was stopped, and the reaction solution was cooled to room temperature, added with 50 mL of water, and extracted with ethyl acetate (30 mL×3). The organic phases were combined, and concentrated under reduced pressure. The residue was purified by thin layer chromatography with developing solvent system B to obtain the title product 5 (33 mg), yield: 33.0%.

MS m/z (ESI): 318.4 [M+1].

$^1$H NMR (400 MHz, DMSO-d$_6$) δ 8.99-8.98 (m, 1H), 8.41-8.39 (m, 1H), 7.97 (s, 1H), 7.69 (s, 1H), 7.61-7.58 (m, 1H), 7.39 (s, 2H), 6.19-6.14 (m, 2H), 2.75 (s, 3H), 2.21 (s, 3H).

Example 6

5-(Furan-2-yl)-6-(8-methylquinolin-6-yl)-1,2,4-triazin-3-amine

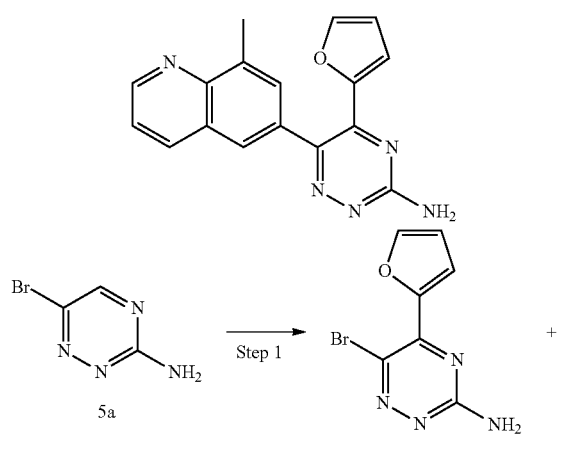

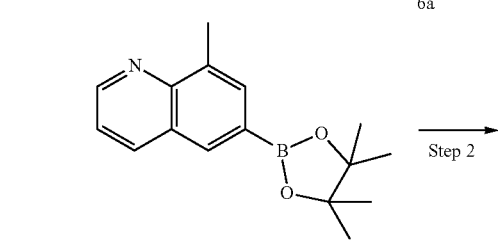

Step 1

6-Bromo-5-(5-methylfuran-2-yl)-1,2,4-triazin-3-amine 6a

Compound 5a (1.0 g, 5.72 mmol), 6 mL of trifluoroacetic acid and 6 mL of dichloromethane were added to a reaction flask. The reaction solution was added with furan (457 μL, 6.29 mmol), and stirred at room temperature for 17 hours. The reaction was stopped, and the reaction solution was added dropwise with saturated sodium bicarbonate solution to adjust the pH>7. The reaction solution was added with 20 mL of a pre-prepared aqueous solution of potassium hydroxide (962 mg, 17.14 mmol) and potassium hexacyanoferrate (5.65 g, 17.14 mmol), and stirred at room temperature for 1 hour. The reaction was stopped, and the reaction solution was extracted with dichloromethane (100 mL×4). The organic phases were combined, added with silica gel, and concentrated under reduced pressure. The residue was purified by CombiFlash rapid preparation instrument with elution system C to obtain the title product 6a (222 mg), yield: 16.1%.

MS m/z (ESI): 243.3 [M+1].

Step 2

5-(Furan-2-yl)-6-(8-methylquinolin-6-yl)-1,2,4-triazin-3-amine 6

Compound 6a (70 mg, 0.29 mmol), compound 1b (86 mg, 0.32 mmol), [1,1'-bis(diphenylphosphino)ferrocene]dichloropalladium (21 mg, 0.029 mmol) and potassium carbonate (160 mg, 1.16 mmol) were dissolved successively in 12 mL of a mixed solution of 1,4-dioxane and water (V/V=5:1) under an argon atmosphere. The reaction solution was heated to 90° C., and stirred for 2 hours. The reaction was stopped, and the reaction solution was cooled to room temperature, added with 50 mL of water, and extracted with ethyl acetate (30 mL×3). The organic phases were combined, and concentrated under reduced pressure. The residue was purified by thin layer chromatography with developing solvent system B to obtain the title product 6 (35 mg), yield: 39.8%.

MS m/z (ESI): 304.4 [M+1].

$^1$H NMR (400 MHz, DMSO-d$_6$) δ 9.04-9.02 (m, 1H), 8.21-8.19 (m, 1H), 7.91 (s, 1H), 7.68 (s, 1H), 7.56 (s, 1H), 7.50-7.47 (m, 1H), 6.44-6.43 (m, 1H), 6.38-6.36 (m, 1H), 5.50 (s, 2H), 2.86 (s, 3H).

Example 7

6-(8-Methylquinolin-6-yl)-5-(thiophen-2-yl)-1,2,4-triazin-3-amine

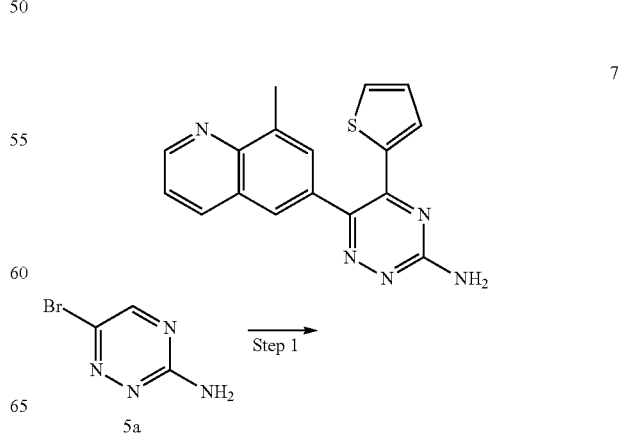

-continued

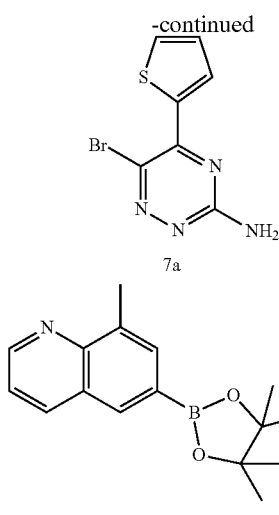

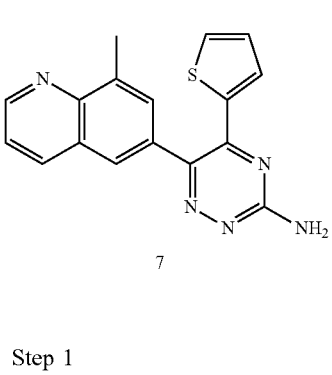

Step 1

6-Bromo-5-(thiophen-2-yl)-1,2,4-triazin-3-amine 7a

Compound 5a (1.0 g, 5.72 mmol), 6 mL of trifluoroacetic acid and 6 mL of dichloromethane were added to a reaction flask. The reaction solution was added with thiophene (503 μL, 6.29 mmol), and stirred at room temperature for 17 hours. The reaction was stopped, and the reaction solution was added dropwise with saturated sodium bicarbonate solution to adjust the pH>7. The reaction solution was added with 30 mL of a pre-prepared aqueous solution of potassium hydroxide (962 mg, 17.14 mmol) and potassium hexacyanoferrate (5.65 g, 17.14 mmol), and stirred at room temperature for 2 hours. The reaction was stopped, and the reaction solution was extracted with ethyl acetate (50 mL×3). The organic phases were combined, added with silica gel, and concentrated under reduced pressure. The residue was purified by CombiFlash rapid preparation instrument with elution system C to obtain the title product 7a (400 mg), yield: 27.2%.

MS m/z (ESI): 259.2 [M+1].

Step 2

6-(8-Methylquinolin-6-yl)-5-(thiophen-2-yl)-1,2,4-triazin-3-amine 7

Compound 7a (70 mg, 0.27 mmol), compound 1b (81 mg, 0.30 mmol), [1,1'-bis(diphenylphosphino)ferrocene]dichloropalladium (20 mg, 0.027 mmol) and potassium carbonate (150 mg, 1.09 mmol) were dissolved successively in 12 mL of a mixed solution of 1,4-dioxane and water (V/V=5:1) under an argon atmosphere. The reaction solution was heated to 90° C., and stirred for 2 hours. The reaction was stopped, and the reaction solution was cooled to room temperature, added with 50 mL of water, and extracted with ethyl acetate (50 mL×3). The organic phases were combined, and concentrated under reduced pressure. The residue was purified by thin layer chromatography with developing solvent system B to obtain the title product 7 (40 mg), yield: 46.0%.

MS m/z (ESI): 320.4 [M+1].

$^1$H NMR (400 MHz, DMSO-$d_6$) δ 9.00-8.99 (m, 1H), 8.42-8.40 (m, 1H), 8.02 (s, 1H), 7.77-7.76 (m, 1H), 7.72 (s, 1H), 7.62-7.59 (m, 1H), 7.41 (s, 2H), 6.94-6.92 (m, 1H), 6.82-6.81 (m, 1H), 2.75 (s, 3H).

Example 8

5-(4-Fluorophenyl)-6-(8-methylquinolin-6-yl)-1,2,4-triazin-3-amine

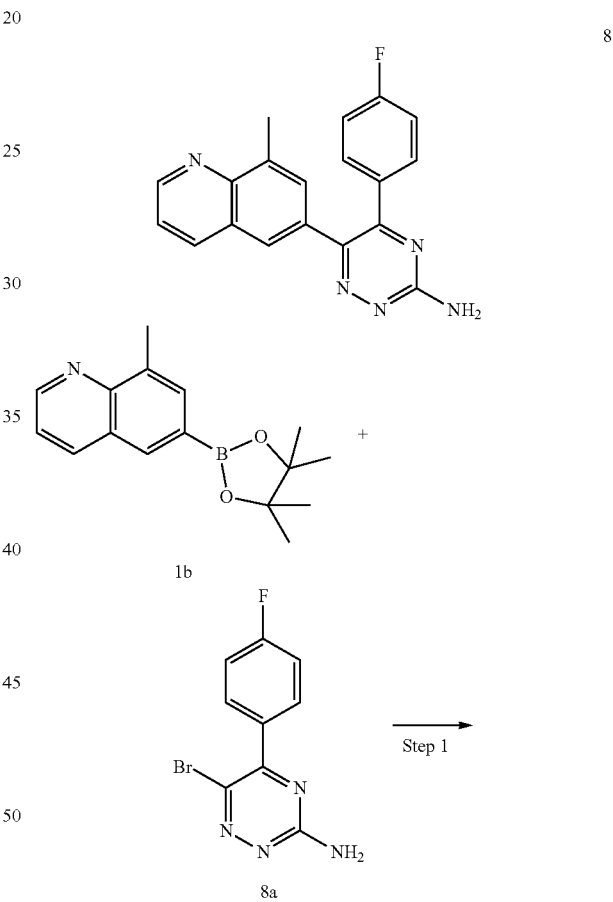

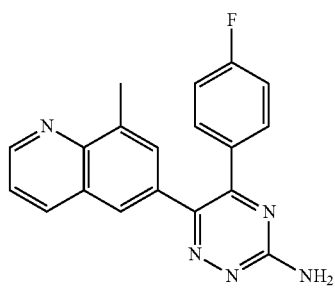

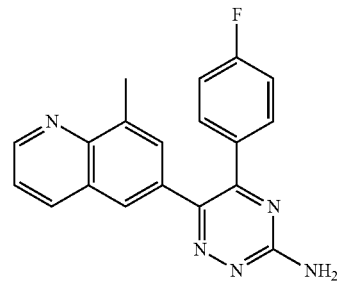

Step 1

5-(4-Fluorophenyl)-6-(8-methylquinolin-6-yl)-1,2,4-triazin-3-amine 8

Compound 1b (100 mg, 0.37 mmol), 6-bromo-5-(4-fluorophenyl)-1,2,4-triazin-3-amine 8a (100 mg, 0.37 mmol, prepared according to the known method disclosed in "*Journal of Medicinal Chemistry,* 2012, 55(5), 1898-1903"), [1,1'-bis(diphenylphosphino)ferrocene]dichloropalladium (54 mg, 0.074 mmol) and potassium carbonate (154 mg, 1.12 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 8 (15 mg), yield: 12.2%.

MS m/z (ESI): 332.4 [M+1].

$^1$H NMR (400 MHz, DMSO-d$_6$) δ 8.92-8.93 (m, 1H), 8.25-8.27 (d, 1H), 7.80 (s, 1H), 7.59 (s, 1H), 7.48-7.55 (m, 5H), 7.17-7.21 (m, 2H), 2.64 (s, 3H).

Example 9

5-Phenyl-6-(8-(trifluoromethyl)quinolin-6-yl)-1,2,4-triazin-3-amine 9

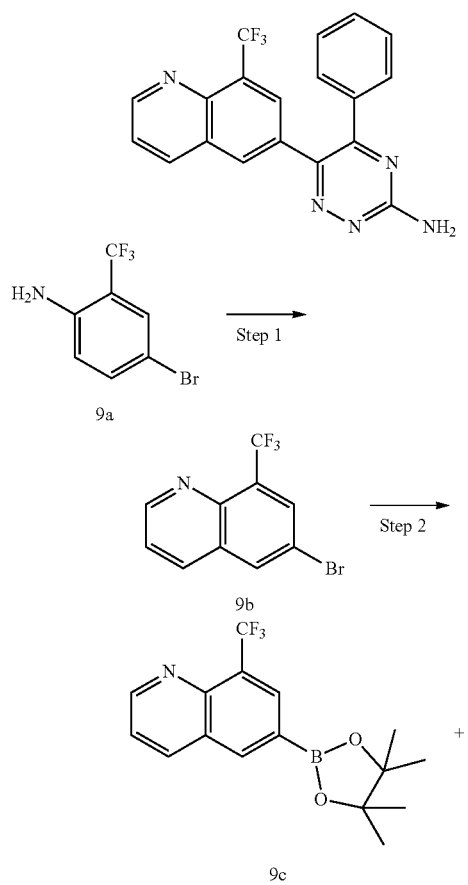

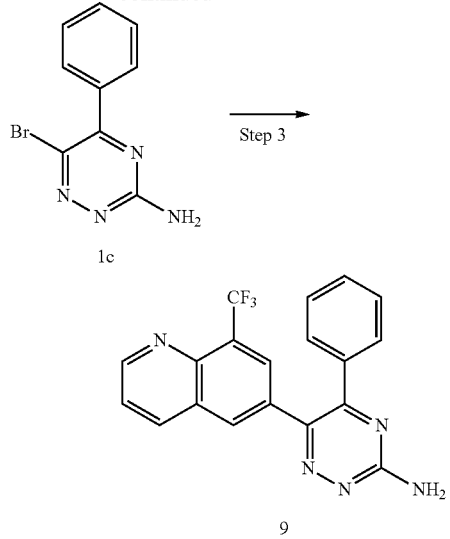

Step 1

6-Bromo-8-(trifluoromethyl)quinoline 9b

2-Amino-5-bromobenzotrifluoride 9a (1.1 g, 4.58 mmol), 1,2,3-propanetriol (1.69 g, 18.3 mmol) and iron (II) sulfate heptahydrate (204 mg, 0.73 mmol) were added to a reaction flask. The reaction solution was cooled to 0° C., and added dropwise with 0.8 mL of sulfuric acid. After completion of the addition, the reaction solution was heated to 120° C., and stirred for 4 hours. The reaction was stopped, and the reaction solution was cooled to room temperature, added with 20 mL of water, and extracted with ethyl acetate (30 mL×3). The organic phases were combined, and concentrated under reduced pressure. The residue was purified by CombiFlash rapid preparation instrument with elution system B to obtain the title product 9b (0.9 g), yield: 71.4%.

MS m/z (ESI): 210.6 [M+1].

Step 2

6-(4,4,5,5-Tetramethyl-1,3,2-dioxaborolan-2-yl)-8-(trifluoromethyl)quinoline 9c Compound 9b (276 mg, 1.00 mmol), bis(pinacolato)diboron (381 mg, 1.50 mmol), [1,1'-bis(diphenylphosphino)ferrocene]dichloropalladium (146 mg, 0.20 mmol) and potassium acetate (294 mg, 3.00 mmol) were dissolved successively in 15 mL of glycol dimethyl ether under an argon atmosphere. The reaction solution was heated to 80° C., and stirred for 12 hours. The reaction was stopped, and the reaction solution was cooled to room temperature and filtrated. The filtrate was concentrated under reduced pressure, and the residue was purified by CombiFlash rapid preparation instrument with elution system B to obtain the title product 9c (250 mg), yield: 77.4%.

MS m/z (ESI): 324.1 [M+1].

Step 3

5-Phenyl-6-(8-(trifluoromethyl)quinolin-6-yl)-1,2,4-triazin-3-amine 9

Compound 9c (129 mg, 0.40 mmol), 6-bromo-5-phenyl-1,2,4-triazin-3-amine 1c (100 mg, 0.40 mmol), [1,1'-bis (diphenylphosphino)ferrocene]dichloropalladium (58 mg, 0.08 mmol) and potassium carbonate (156 mg, 1.20 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature, and filtrated. The filtrate was concentrated under reduced pressure, and the residue was added with 20 mL of ethyl acetate, washed with saturated sodium chloride solution (10 mL), dried over anhydrous sodium sulfate, and filtrated. The filtrate was concentrated under reduced pressure, and the residue was purified by CombiFlash rapid preparation instrument with elution system A to obtain the title product 9 (50 mg), yield: 34.2%.

MS m/z (ESI): 368.4 [M+1].

$^1$H NMR (400 MHz, DMSO-d$_6$) δ 9.04-9.05 (m, 1H), 8.47-8.49 (d, 1H), 8.39 (s, 1H), 7.97 (s, 1H), 7.63-7.71 (m, 3H), 7.44-7.45 (m, 3H), 7.34-7.38 (m, 2H).

Example 10

6-(8-Isopropylquinolin-6-yl)-5-phenyl-1,2,4-triazin-3-amine 10

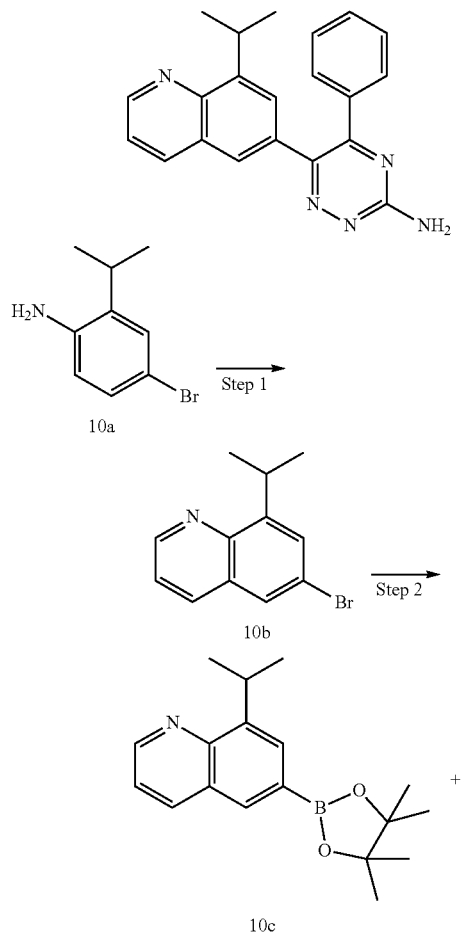

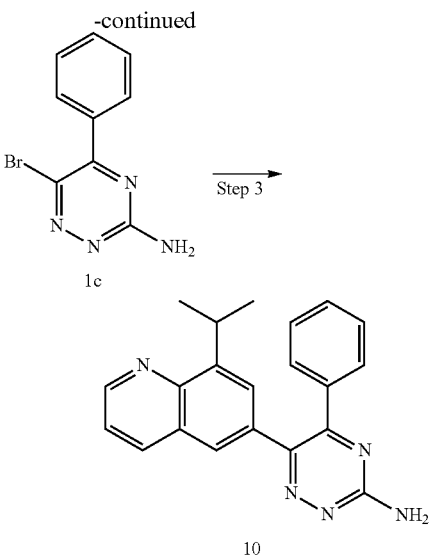

Step 1

6-Bromo-8-isopropylquinoline 10b

4-Bromo-2-isopropylaniline 10a (1.0 g, 4.70 mmol, prepared according to the known method disclosed in "Synthesis, 2013, 45(17), 2474-2480"), 1,2,3-propanetriol (2.1 g, 23.40 mmol) and iron (II) sulfate heptahydrate (0.2 g, 0.75 mmol) were added to a reaction flask. The reaction solution was cooled to 0° C., and added dropwise with 0.9 mL of sulfuric acid. After completion of the addition, the reaction solution was heated to 120° C., and stirred for 3 hours. The reaction was stopped, and the reaction solution was cooled to room temperature, added with 20 mL of water, and extracted with ethyl acetate (30 mL×3). The organic phases were combined, washed with saturated sodium chloride solution (20 mL), dried over anhydrous sodium sulfate, and filtrated. The filtrate was concentrated under reduced pressure, and the residue was purified by CombiFlash rapid preparation instrument with elution system B to obtain the title product 10b (0.6 g), yield: 51.7%.

MS m/z (ESI): 251.1 [M+1].

Step 2

8-Isopropyl-6-(4,4,5,5-tetramethyl-1,3,2-dioxaborolan-2-yl)quinoline 10c

Compound 10b (600 mg, 2.40 mmol), bis(pinacolato)diboron (731 mg, 2.88 mmol), [1,1'-bis(diphenylphosphino)ferrocene]dichloropalladium (350 mg, 0.48 mmol) and potassium acetate (705 mg, 7.20 mmol) were dissolved successively in 40 mL of glycol dimethyl ether under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 10c (450 mg), yield: 63.1%.

MS m/z (ESI): 298.2 [M+1].

Step 3

6-(8-Isopropylquinolin-6-yl)-5-phenyl-1,2,4-triazin-3-amine 10

Compound 10c (118 mg, 0.40 mmol), 6-bromo-5-phenyl-1,2,4-triazin-3-amine 1c (100 mg, 0.40 mmol), [1,1'-bis(diphenylphosphino)ferrocene]dichloropalladium (58 mg, 0.08 mmol) and potassium carbonate (165 mg, 1.20 mmol) were dissolved successively in 24 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 10 (40 mg), yield: 29.3%.

MS m/z (ESI): 342.4 [M+1].

$^1$H NMR (400 MHz, DMSO-$d_6$) δ 8.90-8.92 (m, 1H), 8.36-8.38 (d, 1H), 8.11 (s, 1H), 7.51-7.53 (m, 3H), 7.40-7.41 (m, 3H), 7.33-7.35 (m, 2H), 7.25 (m, 1H), 4.10-4.12 (m, 1H), 0.99-1.01 (s, 6H).

Example 11

6-(8-Ethylquinolin-6-yl)-5-phenyl-1,2,4-triazin-3-amine 11

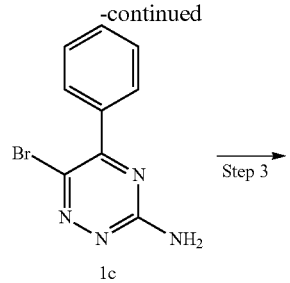

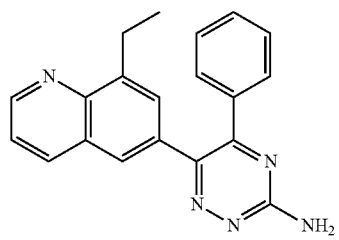

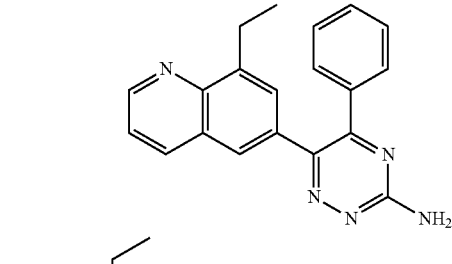

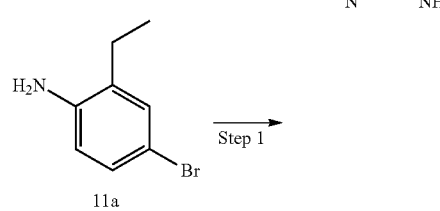

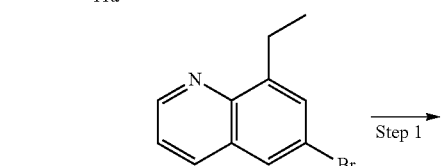

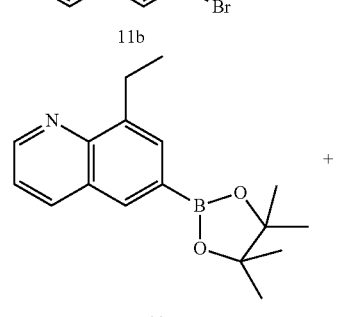

Step 1

6-Bromo-8-ethylquinoline 11b

4-Bromo-2-ethylaniline 11a (1.0 g, 5.00 mmol, Alfa), 1,2,3-propanetriol (2.3 g, 25.00 mmol) and iron (II) sulfate heptahydrate (0.22 g, 0.80 mmol) were added to a reaction flask. The reaction solution was cooled to 0° C., and added dropwise with 0.9 mL of sulfuric acid. After completion of the addition, the reaction solution was heated to 120° C., and stirred for 2 hours. The reaction was stopped, and the reaction solution was cooled to room temperature, added with 20 mL of water, and extracted with ethyl acetate (30 mL×3). The organic phases were combined, washed with saturated sodium chloride solution (20 mL), dried over anhydrous sodium sulfate, and filtrated. The filtrate was concentrated under reduced pressure, and the residue was purified by CombiFlash rapid preparation instrument with elution system B to obtain the title product 11b (0.9 g), yield: 76.3%.

MS m/z (ESI): 237.1 [M+1].

Step 2

8-Ethyl-6-(4,4,5,5-tetramethyl-1,3,2-dioxaborolan-2-yl)quinoline 11c

Compound 11b (472 mg, 2.00 mmol), bis(pinacolato)diboron (610 mg, 2.40 mmol), [1,1'-bis(diphenylphosphino)ferrocene]dichloropalladium (292 mg, 0.40 mmol) and potassium acetate (588 mg, 6.00 mmol) were dissolved successively in 30 mL of glycol dimethyl ether under an argon atmosphere. The reaction solution was heated to 80° C., and stirred for 3 hours. The reaction was stopped, and the reaction solution was cooled to room temperature and filtrated. The filtrate was concentrated under reduced pressure, and the residue was purified by silica gel column chromatography with elution system B to obtain the title product 11c (400 mg), yield: 70.7%.

MS m/z (ESI): 284.1 [M+1].

Step 3

6-(8-Ethylquinolin-6-yl)-5-phenyl-1,2,4-triazin-3-amine 11

Compound 11c (113 mg, 0.40 mmol), 6-bromo-5-phenyl-1,2,4-triazin-3-amine 1c (100 mg, 0.40 mmol), [1,1'-bis(diphenylphosphino)ferrocene]dichloropalladium (58 mg, 0.08 mmol) and potassium carbonate (165 mg, 1.20 mmol) were dissolved successively in 24 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 11 (20 mg), yield: 15.3%.

MS m/z (ESI): 328.4 [M+1].

$^1$H NMR (400 MHz, Pyridine-$d_5$) δ 8.93-8.95 (m, 1H), 8.52 (br, 2H), 8.10 (s, 1H), 8.06-8.10 (m, 1H), 7.72 (s, 1H), 7.65-7.67 (m, 2H), 7.32-7.35 (m, 1H), 7.26-7.28 (m, 3H), 3.30-3.32 (m, 2H), 1.22-1.25 (t, 3H).

Example 12

6-(8-Cyclopropylquinolin-6-yl)-5-phenyl-1,2,4-triazin-3-amine 12

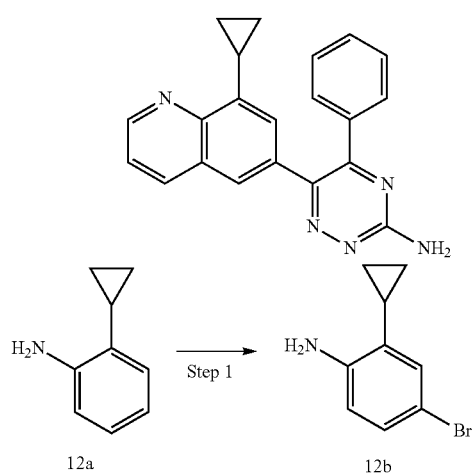

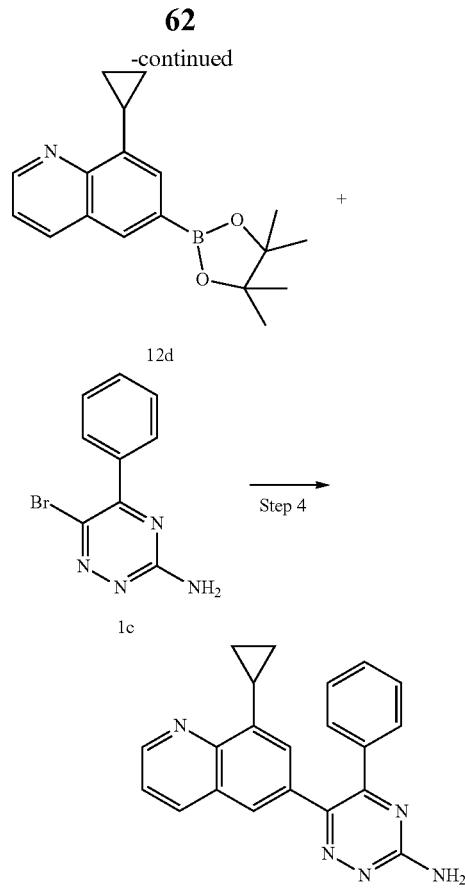

Step 1

4-Bromo-2-cyclopropylaniline 12b

2-Cyclopropylaniline 12a (1.0 g, 7.52 mmol, prepared according to the method disclosed in the patent application "WO201314997") was added to 100 mL of acetonitrile, followed by addition of N-bromosuccinimide (1.4 g, 7.89 mmol) and ammonium acetate (58 mg, 0.075 mmol). The reaction solution was stirred for 2 hours before the reaction was stopped. The reaction solution was added with 60 mL of water, and extracted with ethyl acetate (100 mL×3). The organic phases were combined, washed with saturated sodium chloride solution (50 mL), dried over anhydrous sodium sulfate, and filtrated. The filtrate was concentrated under reduced pressure, and the residue was purified by CombiFlash rapid preparation instrument with elution system B to obtain the title product 12b (0.85 g), yield: 53.5%.

MS m/z (ESI): 213.1 [M+1].

Step 2

6-Bromo-8-cyclopropylquinoline 12c

4-Bromo-2-ethylaniline 12b (500 mg, 2.36 mmol), 1,2,3-propanetriol (1.08 g, 11.80 mmol) and iron (II) sulfate heptahydrate (105 mg, 0.38 mmol) were added to a reaction flask. The reaction solution was cooled to 0° C., and added dropwise with 0.5 mL of sulfuric acid. After completion of the addition, the reaction solution was heated to 120° C., and stirred for 2 hours. The reaction was stopped, and the reaction solution was cooled to room temperature, added with 50 mL of water, and extracted with ethyl acetate (50 mL×3). The organic phases were combined, washed with saturated sodium chloride solution (50 mL), dried over anhydrous sodium sulfate, and filtrated. The filtrate was concentrated under reduced pressure, and the residue was purified by CombiFlash rapid preparation instrument with elution system B to obtain the title product 12c (0.4 g), yield: 68.5%.

MS m/z (ESI): 249.1 [M+1].

Step 3

8-Cyclopropyl-6-(4,4,5,5-tetramethyl-1,3,2-dioxaborolan-2-yl)quinoline 12d

Compound 12c (100 mg, 0.40 mmol), bis(pinacolato)diboron (123 mg, 0.48 mmol), [1,1'-bis(diphenylphosphino)ferrocene]dichloropalladium (59 mg, 0.08 mmol) and potassium acetate (118 mg, 1.20 mmol) were dissolved successively in 10 mL of glycol dimethyl ether under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 12d (94 mg), yield: 79.0%.

MS m/z (ESI): 296.2 [M+1].

Step 4

6-(8-Cyclopropylquinolin-6-yl)-5-phenyl-1,2,4-triazin-3-amine 12

Compound 12d (94 mg, 0.32 mmol), 6-bromo-5-phenyl-1,2,4-triazin-3-amine 1c (80 mg, 0.32 mmol), [1,1'-bis(diphenylphosphino)ferrocene]dichloropalladium (47 mg, 0.064 mmol) and potassium carbonate (132 mg, 0.96 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 12 (10 mg), yield: 9.2%.

MS m/z (ESI): 340.1 [M+1].

$^1$H NMR (400 MHz, DMSO-$d_6$) δ 8.92-8.94 (m, 1H), 8.35-8.38 (dd, 1H), 8.02 (s, 1H), 7.43-7.57 (m, 3H), 7.37-7.39 (m, 1H), 7.34-7.36 (m, 4H), 6.79-6.80 (m, 1H), 3.06-3.08 (m, 1H), 0.91-0.93 (m, 2H), 0.29-0.30 (m, 2H).

Example 13 (Comparative Example 1)

6-(Naphthalen-2-yl)-5-phenyl-1,2,4-triazin-3-amine

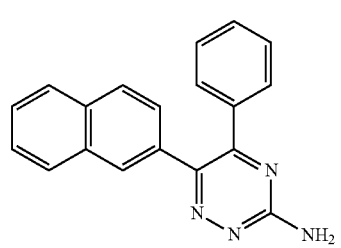

13

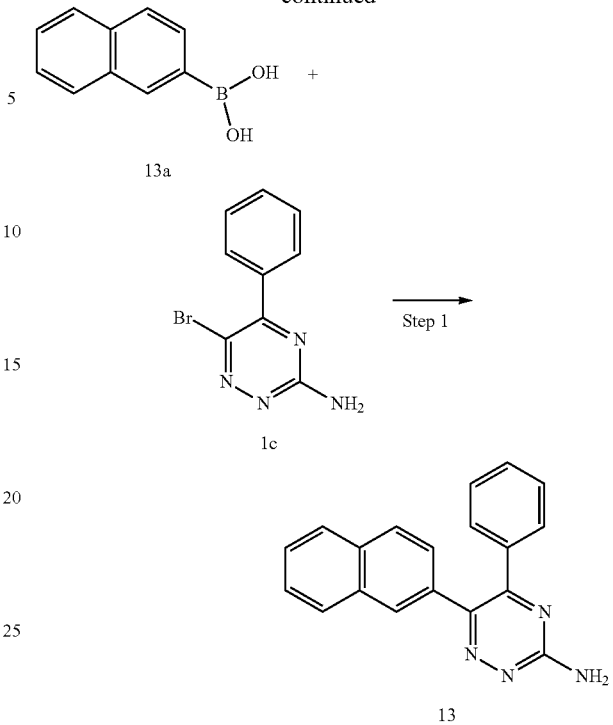

6-(Naphthalen-2-yl)-5-phenyl-1,2,4-triazin-3-amine 13

2-Naphthylboronic acid 13a (55 mg, 0.32 mmol), 6-bromo-5-phenyl-1,2,4-triazin-3-amine 1c (80 mg, 0.32 mmol), [1,1'-bis(diphenylphosphino)ferrocene]dichloropalladium (47 mg, 0.064 mmol) and potassium carbonate (132 mg, 0.96 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 13 (20 mg), yield: 21.3%.

MS m/z (ESI): 299.1 [M+1].

$^1$H NMR (400 MHz, DMSO-$d_6$) δ 8.02 (s, 1H), 7.80-7.87 (m, 3H), 7.31-7.52 (m, 10H).

Example 14

6-(4-Methylquinolin-6-yl)-5-phenyl-1,2,4-triazin-3-amine 14

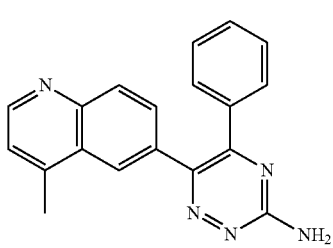

14

-continued

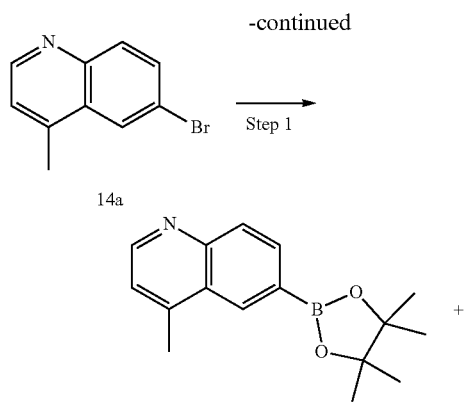

Step 1

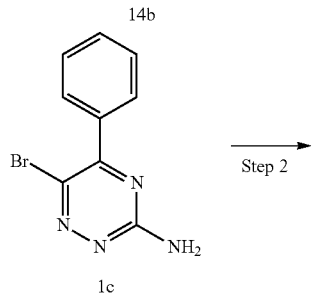

Step 2 chloropalladium (58 mg, 0.08 mmol) and potassium carbonate (165 mg, 1.20 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 14 (15 mg), yield: 12%.

MS m/z (ESI): 314.4 [M+1].

$^1$H NMR (400 MHz, DMSO-$d_6$) δ 8.74-8.75 (d, 1H), 8.02 (m, 1H), 7.90-7.93 (d, 1H), 7.71-7.73 (d, 1H), 7.63 (m, 2H), 7.42-7.44 (m, 3H), 7.34-7.36 (m, 3H), 2.46 (s, 3H).

Example 15

6-(4-Methylquinazolin-6-yl)-5-phenyl-1,2,4-triazin-3-amine 15

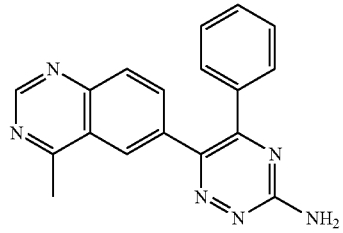

Step 1

Step 1

4-Methyl-6-(4,4,5,5-tetramethyl-1,3,2-dioxaborolan-2-yl)quinoline 14b

6-Bromo-4-methylquinoline 14a (444 mg, 2 mmol, prepared according to the known method disclosed in "*Tetrahedron*, 2003, 59(6), 813-819"), bis(pinacolato)diboron (762 mg, 3 mmol), [1,1'-bis(diphenylphosphino)ferrocene]dichloropalladium (292 mg, 0.40 mmol) and potassium acetate (588 mg, 6.00 mmol) were dissolved successively in 20 mL of dimethyl ether under an argon atmosphere. The reaction solution was heated to 80° C., and stirred for 12 hours. The reaction was stopped, and the reaction solution was cooled to room temperature and filtrated. The filtrate was concentrated under reduced pressure, and the residue was purified by CombiFlash rapid preparation instrument with elution system B to obtain the title product 14b (460 mg), yield: 85.5%.

MS m/z (ESI): 270.4 [M+1].

Step 2

6-(4-Methylquinolin-6-yl)-5-phenyl-1,2,4-triazin-3-amine 14

Compound 14b (107 mg, 0.4 mmol), compound 1c (100 mg, 0.4 mmol), [1,1'-bis(diphenylphosphino)ferrocene]di-

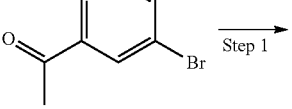

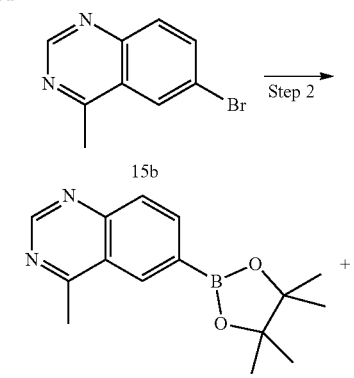

Step 2

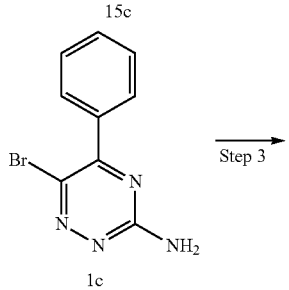

Step 3

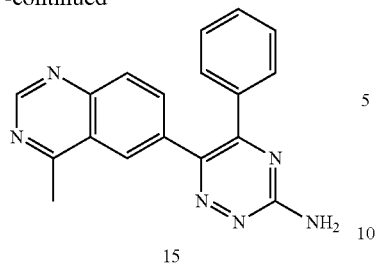

15

Step 1

6-Bromo-4-methylquinazoline 15b 1-(2-Amino-5-bromophenyl)ethanone 15a (1 g, 4.67 mmol, prepared according to the known method disclosed in "*Journal of Medicinal Chemistry*, 2015, 58(14), 5522-5537"), triethyl orthoformate (1.04 g, 7.01 mmol) and ammonium acetate (540.15 mg, 7.01 mmol) were added to a reaction flask. The reaction solution was stirred at 110° C. for 2 hours. The reaction was stopped, and the reaction solution was cooled to room temperature. The reaction solution was purified by CombiFlash rapid preparation instrument with elution system B to obtain the title product 15b (500 mg), yield: 47.98%.

Step 2

4-Methyl-6-(4,4,5,5-tetramethyl-1,3,2-dioxaborolan-2-yl)quinazoline 15c

Compound 15b (360 mg, 1.61 mmol), bis(pinacolato)diboron (409.82 mg, 1.61 mmol), [1,1'-bis(diphenylphosphino)ferrocene]dichloropalladium (236.17 mg, 322.77 µmol) and potassium acetate (475.16 mg, 4.84 mmol) were dissolved successively in 20 mL of dimethyl ether under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 15c (330 mg), yield: 75.7%.

MS m/z (ESI): 271.1[M+1].

Step 3

6-(4-Methylquinazolin-6-yl)-5-phenyl-1,2,4-triazin-3-amine 15

Compound 15c (108 mg, 399.80 µmol), compound 1c (100.38 mg, 399.80 µmmol), [1,1'-bis(diphenylphosphino)ferrocene]dichloropalladium (58.51 mg, 79.96 µmol) and potassium carbonate (165 mg, 1.2 mmol) were dissolved successively in 12 mL of a mixed solution of 1,4-dioxane and water (V/V=4:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 15 (52 mg), yield: 41.38%.

MS m/z (ESI): 315.2 [M+1].

$^1$H NMR (400 MHz, DMSO-$d_6$) δ 9.11 (s, 1H), 8.22 (s, 1H), 7.89-7.90 (m, 2H), 7.59 (m, 2H), 7.43-7.45 (m, 3H), 7.34-7.38 (m, 2H), 2.73 (s, 3H).

Example 16

6-(8-Fluoro-4-methylquinolin-6-yl)-5-phenyl-1,2,4-triazin-3-amine 16

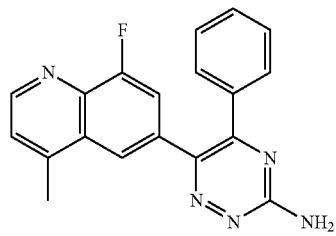

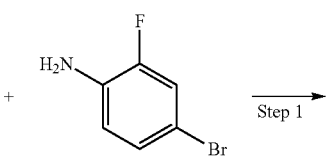

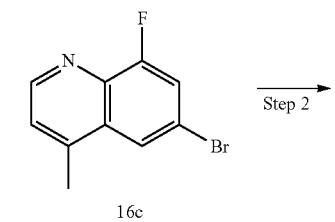

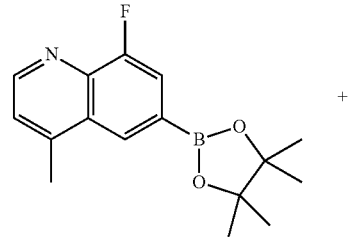

-continued

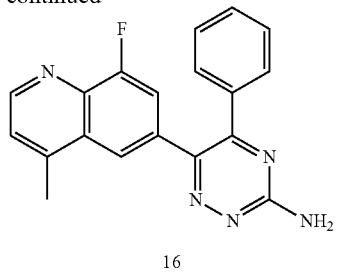

16

Step 1

6-Bromo-8-fluoro-4-methylquinoline 16c

4-Bromo-2-fluoro-aniline 16b (9.99 g, 52.58 mmol, prepared according to the known method disclosed in "*Tetrahedron Letters*, 2015, 56(41), 5646-5650") was dissolved in 300 mL of 1,4-dioxane, followed by dropwise addition of 5 mL of sulfuric acid. The reaction solution was heated to reflux, and then slowly added dropwise with 20 mL of but-3-en-2-one 16a (7.37 g, 105.15 mmol, prepared according to the known method disclosed in "*Tetrahedron Letters*, 2006, 47(37), 6635-6636") in 1,4-dioxane over 1.5 hours. After completion of the addition, the reaction solution was heated to reflux for 2 hours. The reaction solution was cooled to room temperature, and concentrated under reduced pressure. The residue was added with water, added dropwise with saturated sodium bicarbonate solution until the pH of the mixture was 10, and extracted with ethyl acetate three times. The organic phases were combined, washed once with saturated sodium chloride solution, dried over anhydrous sodium sulfate, and filtrated. The filtrate was concentrated under reduced pressure, and the residue was purified by CombiFlash rapid preparation instrument with elution system B to obtain the title product 16c (3.5 g), yield: 27.73%.

MS m/z (ESI):240.0 [M+1].

Step 2

8-Fluorine-4-methyl-6-(4,4,5,5-tetramethyl-1,3,2-dioxaborolan-2-yl)quinoline 16d Compound 16c (480 mg, 2.00 mmol), bis(pinacolato)diboron (761.59 mg, 3.00 mmol), [1,1'-bis(diphenylphosphino)ferrocene]dichloropalladium (292.60 mg, 399.88 µmol) and potassium acetate (588.68 mg, 6.00 mmol) were added to 20 mL of dimethyl ether under an argon atmosphere. The reaction solution was heated to 80° C., and stirred for 3 hours. The reaction was stopped, and the reaction solution was cooled to room temperature and filtrated. The filtrate was concentrated under reduced pressure, and the residue was purified by CombiFlash rapid preparation instrument with elution system B to obtain the title product 16d (460 mg), yield: 80.12%.

MS m/z (ESI): 288.1 [M+1].

Step 3

6-(8-Fluoro-4-methylquinolin-6-yl)-5-phenyl-1,2,4-triazin-3-amine 16

Compound 16d (110 mg, 383.09 µmol), compound 1c (96 mg, 383.09 µmol), [1,1'-bis(diphenylphosphino)ferrocene] dichloropalladium (56 mg, 76.62 µmol) and potassium carbonate (158.60 mg, 1.15 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 16 (18 mg), yield: 14.2%.

MS m/z (ESI): 332.4 [M+1].

$^1$H NMR (400 MHz, DMSO-d$_6$) δ 8.75-8.76 (m, 1H), 7.78 (s, 1H), 7.52-7.55 (m, 3H), 7.41-7.43 (m, 4H), 7.34-7.36 (m, 2H), 2.42 (s, 3H).

Example 17

5-(2-Fluorophenyl)-6-(4-methylquinolin-6-yl)-1,2,4-triazin-3-amine 17

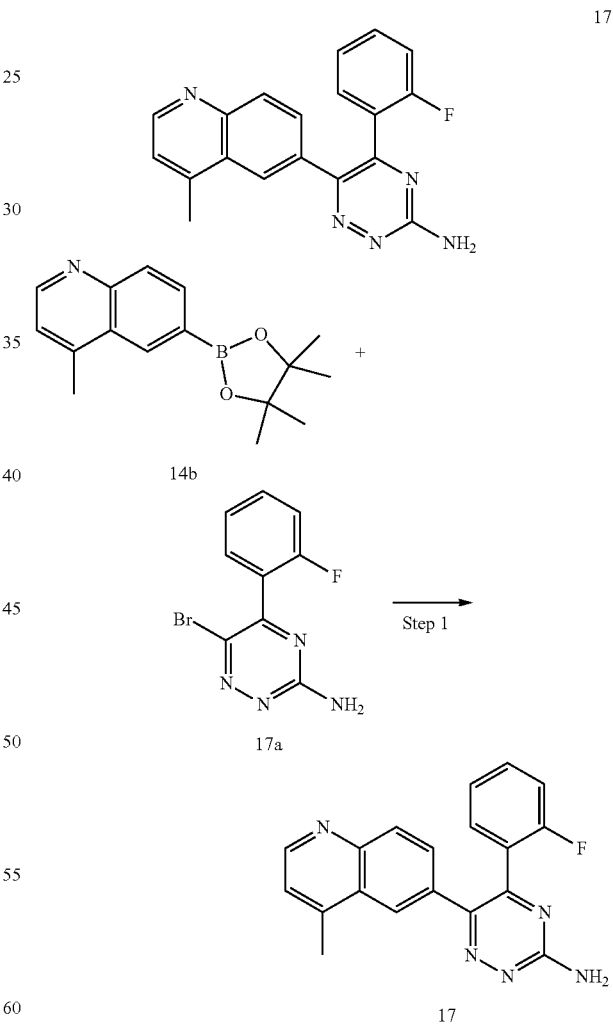

Compound 14b (100 mg, 371.55 µmol), 6-bromo-5-(2-fluorophenyl)-1,2,4-triazin-3-amine 17a (99.97 mg, 371.55 µmol, prepared according to the method disclosed in the patent application "WO2016102672A2"), [1,1'-bis(diphenylphosphino)ferrocene]dichloropalladium (54 mg, 74.35

μmol) and potassium carbonate (153.82 mg, 1.11 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 17 (50 mg), yield: 40.6%.

MS m/z (ESI): 332.4 [M+1].

$^1$H NMR (400 MHz, DMSO-d$_6$) δ 8.70-8.71 (m, 1H), 7.92-7.94 (m, 1H), 7.84-7.87 (m, 1H), 7.80 (s, 1H), 7.60-7.67 (m, 3H), 7.48-7.50 (m, 1H), 7.09-7.36 (m, 2H), 7.04-7.09 (m, 1H), 2.32 (s, 3H).

Example 18

5-(4-Fluorophenyl)-6-(4-methylquinolin-6-yl)-1,2,4-triazin-3-amine 18

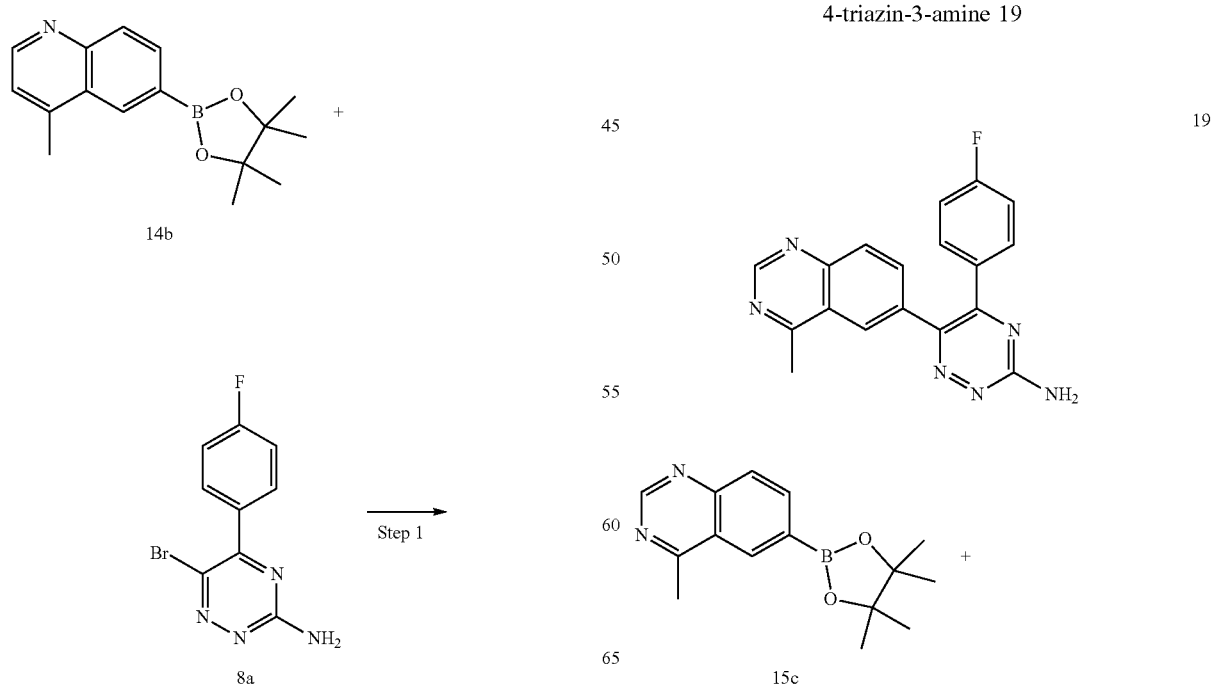

Compound 14b (100 mg, 371.55 μmol), compound 8a (99.97 mg, 371.55 μmol), [1,1'-bis(diphenylphosphino)ferrocene]dichloropalladium (54.37 mg, 74.31 μmol) and potassium carbonate (153.82 mg, 1.11 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 18 (15 mg), yield: 12.18%.

MS m/z (ESI): 332.1 [M+1].

$^1$H NMR (400 MHz, DMSO-d$_6$) δ 8.76-8.77 (m, 1H), 8.09 (m, 1H), 7.92-7.95 (d, 1H), 7.70-7.71 (m, 1H), 7.53 (m, 2H), 7.47-7.50 (m, 2H), 7.39-7.40 (m, 1H), 7.18-7.22 (m, 2H), 2.52 (s, 3H).

Example 19

5-(4-Fluorophenyl)-6-(4-methylquinazolin-6-yl)-1,2,4-triazin-3-amine 19

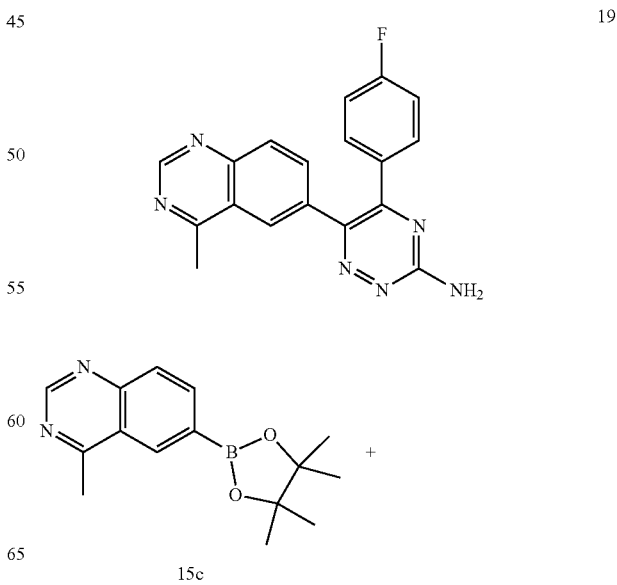

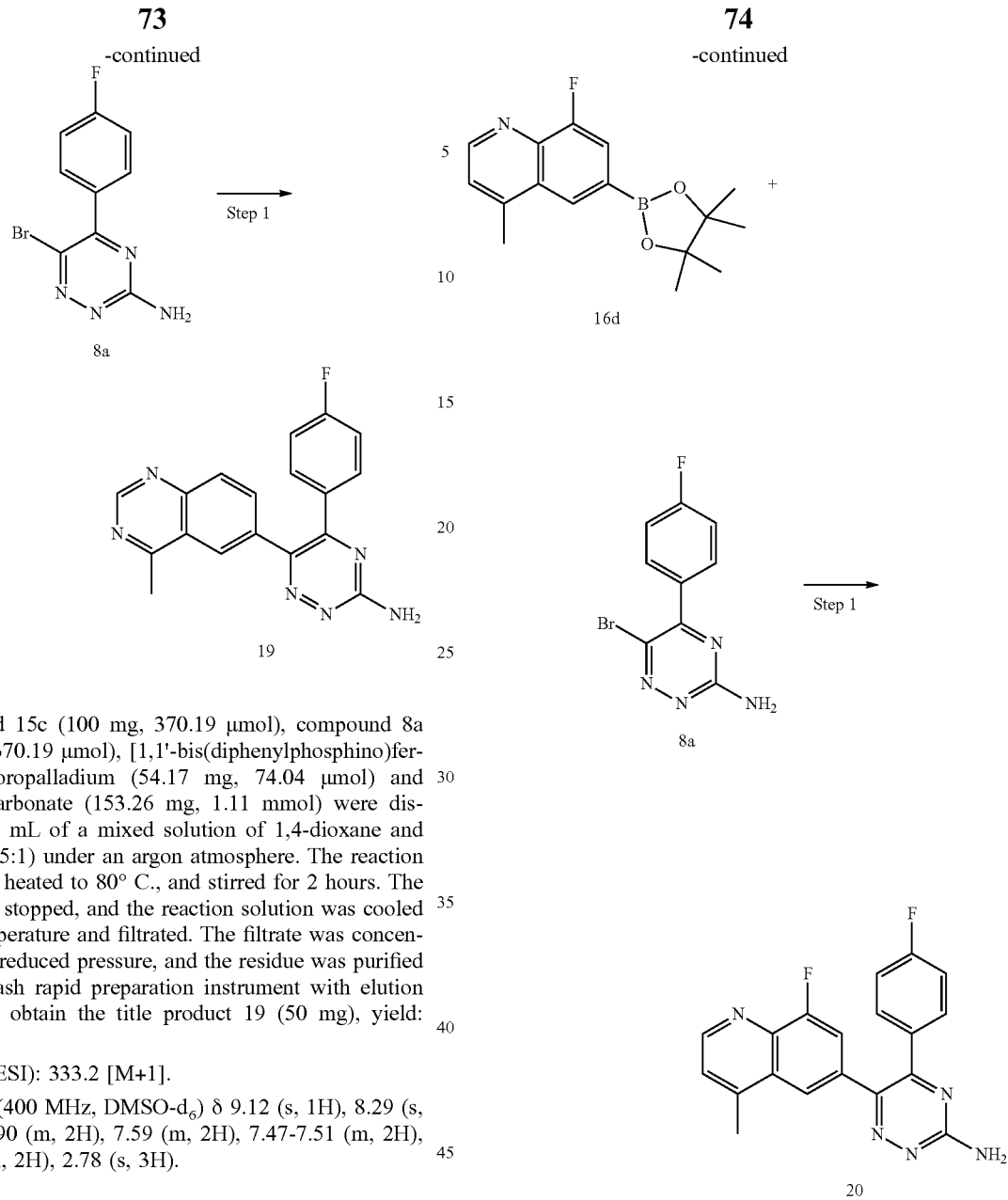

Compound 15c (100 mg, 370.19 μmol), compound 8a (99.61 mg, 370.19 μmol), [1,1'-bis(diphenylphosphino)ferrocene]dichloropalladium (54.17 mg, 74.04 μmol) and potassium carbonate (153.26 mg, 1.11 mmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 19 (50 mg), yield: 40.64%.

MS m/z (ESI): 333.2 [M+1].

$^1$H NMR (400 MHz, DMSO-d$_6$) δ 9.12 (s, 1H), 8.29 (s, 1H), 7.88-7.90 (m, 2H), 7.59 (m, 2H), 7.47-7.51 (m, 2H), 7.19-7.23 (m, 2H), 2.78 (s, 3H).

Example 20

6-(8-Fluoro-4-methylquinolin-6-yl)-5-(4-fluorophenyl)-1,2,4-triazin-3-amine 20

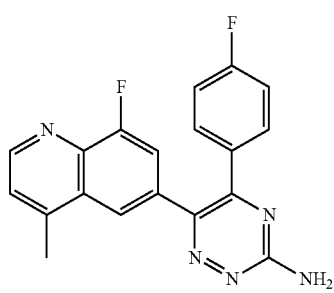

Compound 8a (100 mg, 371.65 μmol), compound 16d (106.71 mg, 371.65 μmol), [1,1'-bis(diphenylphosphino)ferrocene]dichloropalladium (54.39 mg, 74.33 μmol) and potassium carbonate (153.86 mg, 1.11 mmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 20 (50 mg), yield: 38.51%.

MS m/z (ESI): 350.4 [M+1].

$^1$H NMR (400 MHz, DMSO-d$_6$) δ 8.77-8.78 (m, 1H), 7.83 (s, 1H), 7.46-7.55 (m, 6H), 7.19-7.21 (m, 2H), 2.50 (s, 3H).

Example 21

5-(2,4-Difluorophenyl)-6-(4-methylquinolin-6-yl)-1,2,4-triazin-3-amine 21

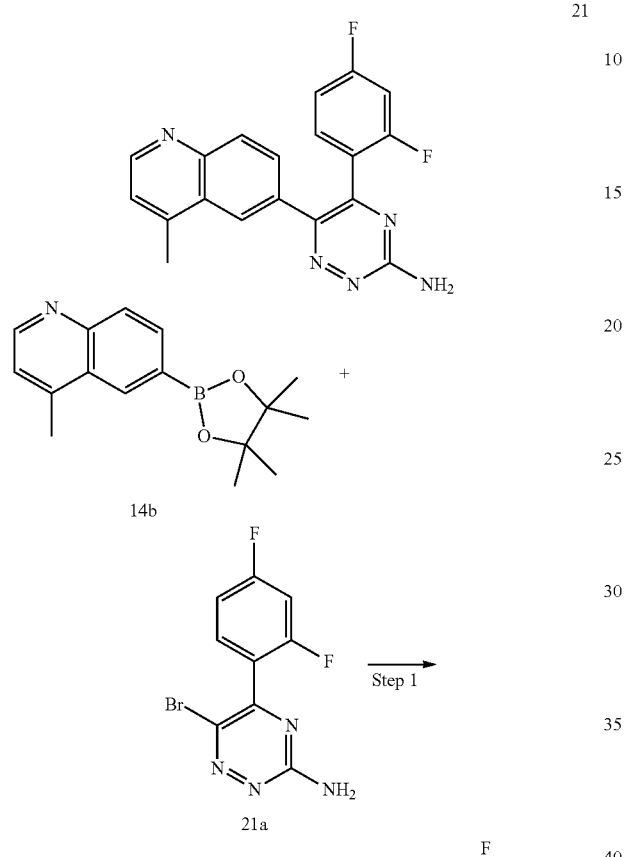

Compound 14b (68 mg, 252.65 μmol), 6-bromo-5-(2,4-difluorophenyl)-1,2,4-triazin-3-amine 21a (72.53 mg, 252.65 μmol, prepared according to the method disclosed in the patent application "WO2011095625A1"), [1,1'-bis(diphenylphosphino)ferrocene]dichloropalladium (36.97 mg, 50.53 μmol) and potassium carbonate (104.60 mg, 757.95 μmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 21 (40 mg), yield: 50.99%.

MS m/z (ESI): 350.2 [M+1].

$^1$H NMR (400 MHz, DMSO-$d_6$) δ 8.74-8.75 (m, 1H), 7.96-7.98 (d, 1H), 7.85-7.89 (m, 2H), 7.75-7.78 (m, 1H), 7.65 (m, 2H), 7.35-7.37 (m, 1H), 7.28-7.30 (m, 1H), 7.19-7.25 (m, 1H), 2.42 (s, 3H).

Example 22

5-(4-Fluorophenyl)-6-[4-(trideuteromethyl)-6-quinolinyl]-1,2,4-triazin-3-amine 22

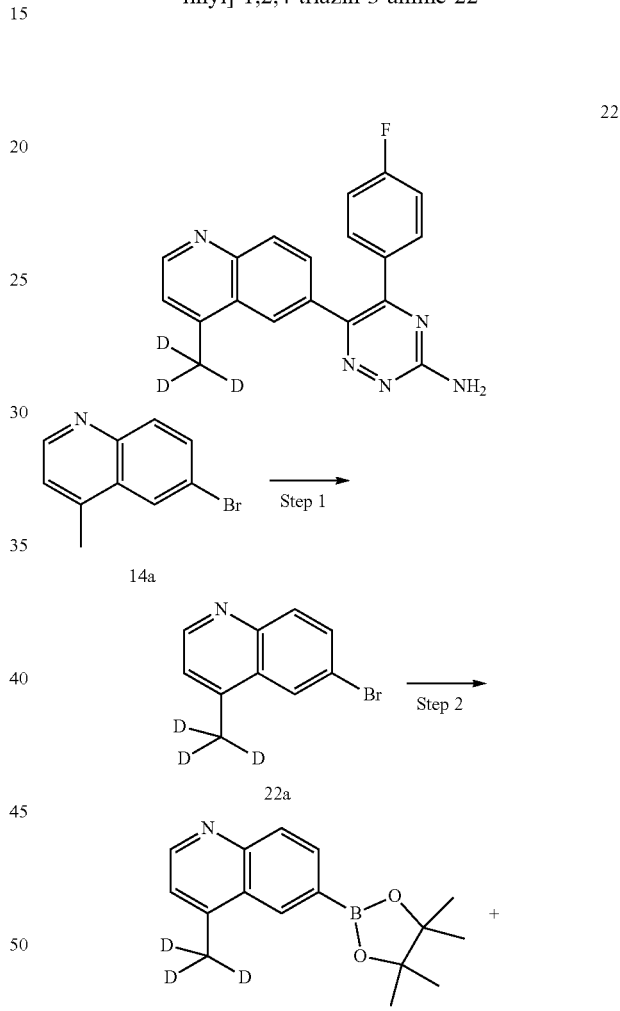

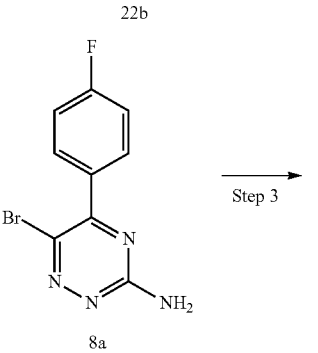

77

-continued

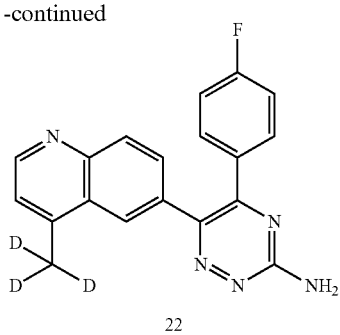

22

Step 1

6-Bromo-4-(trideuteromethyl)quinoline 22a

Compound 14a (222 mg, 999.64 μmol) and benzoic acid (12.21 mg, 99.96 μmol) were dissolved in 1 mL of deuteroxide. The reaction solution was stirred at 100° C. overnight, and then added with saturated sodium bicarbonate solution, and extracted with ethyl acetate three times. The organic phases were combined, and dried over anhydrous sodium sulfate. The residue was purified by CombiFlash rapid preparation instrument with elution system B. The purified solid and benzoic acid (12.21 mg, 99.96 μmol) were added successively to 1 mL of deuteroxide. The reaction solution was stirred at 100° C. overnight, and then added with saturated sodium bicarbonate solution, and extracted with ethyl acetate three times. The organic phases were combined, and dried over anhydrous sodium sulfate. The residue was purified by CombiFlash rapid preparation instrument with elution system B to obtain the title product 22a (100 mg), yield: 44.44%.

MS m/z (ESI): 225.0 [M+1].

Step 2

6-(4,4,5,5-Tetramethyl-1,3,2-dioxaborolan-2-yl)-4-(trideuteromethyl)quinoline 22b Compound 22a (100 mg, 444.25 μmol), bis(pinacolato) diboron (169.22 mg, 666.37 μmol), [1,1'-bis(diphenylphosphino)ferrocene]dichloropalladium (65.01 mg, 88.85 μmol) and potassium acetate (130.80 mg, 1.33 mmol) were added to 10 mL of 1,4-dioxane under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 22b (70 mg), yield: 57.9%.

MS m/z (ESI): 273.1 [M+1].

Step 3

5-(4-Fluorophenyl)-6-[4-(trideuteromethyl)-6-quinolinyl]-1,2,4-triazin-3-amine 22

Compound 22b (70 mg, 257.20 μmol), compound 8a (69.20 mg, 257.20 μmol), [1,1'-bis(diphenylphosphino)ferrocene]dichloropalladium (37.64 mg, 51.44 μmol) and potassium carbonate (106.48 mg, 771.59 μmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, cooled and filtrated. The residue was purified by CombiFlash rapid preparation instrument with elution system A, and the resulting crude product was purified by thin layer chromatography with developing solvent system A to obtain the title product 22 (29 mg), yield: 29.07%.

MS m/z (ESI): 335.5 [M+1].

$^1$H NMR (400 MHz, DMSO-d$_6$) δ 8.75-8.76 (m, 1H), 8.08 (s, 1H), 7.92-7.95 (d, 1H), 7.68-7.70 (d, 1H), 7.47-7.50 (m, 4H), 7.38-7.39 (m, 1H), 7.20-7.22 (m, 2H).

Example 23

6-(4-Methoxyquinolin-6-yl)-5-phenyl-1,2,4-triazin-3-amine 23

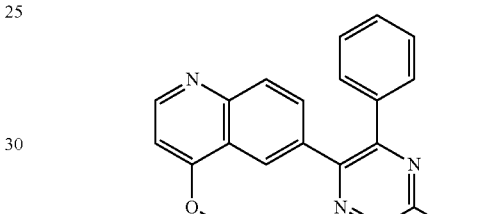

23

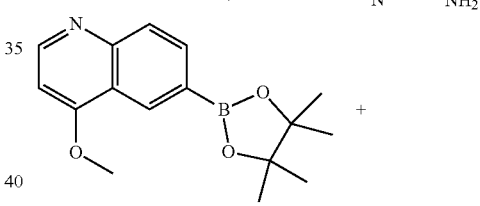

23a

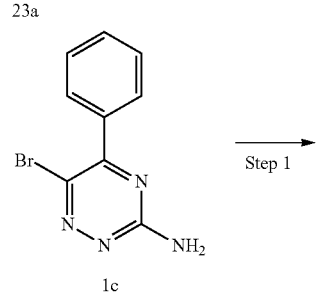

1c

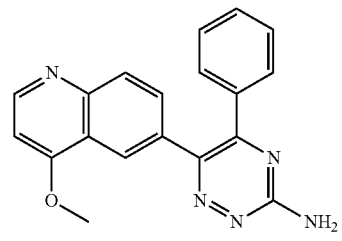

23

4-Methoxy-6-(4,4,5,5-tetramethyl-1,3,2-dioxaborolan-2-yl)quinoline 23a (114 mg, 0.4 mmol, prepared according to the method disclosed in the patent application "WO2011084402A1"), compound 1c (100 mg, 0.4 mmol), [1,1'-bis(diphenylphosphino)ferrocene]dichloropalladium (58 mg, 0.08 mmol) and potassium carbonate (165 mg, 1.2 mmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 23 (20 mg), yield: 15.3%.

MS m/z (ESI): 330.1 [M+1].

$^1$H NMR (400 MHz, DMSO-d$_6$) δ 8.74-8.75 (m, 1H), 8.30 (m, 1H), 7.79-7.81 (d, 1H), 7.48-7.51 (m, 3H), 7.40-7.44 (m, 3H), 7.33-7.35 (m, 2H), 7.03-7.05 (m, 1H), 4.02 (s, 3H).

Example 24

6-(3-Fluoroquinolin-6-yl)-5-phenyl-1,2,4-triazin-3-amine 24

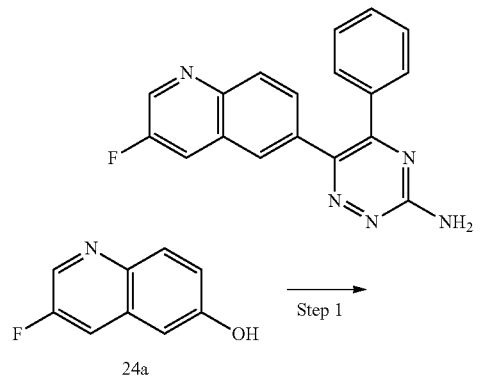

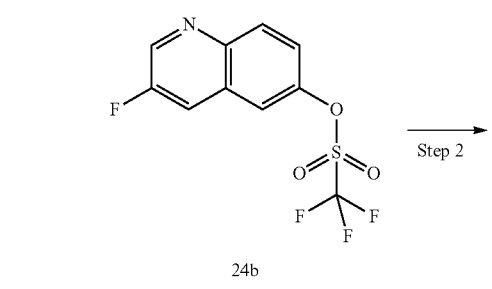

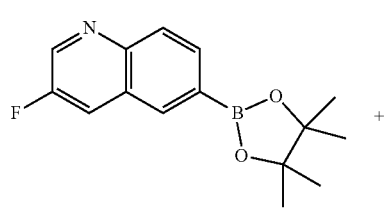

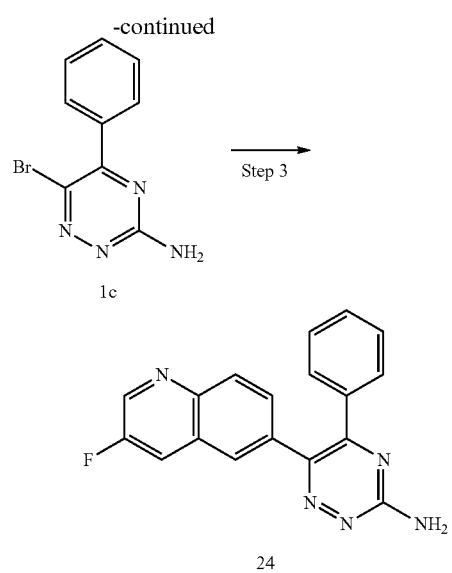

Step 1

3-Fluoroquinolin-6-yl trifluoromethanesulfonate 24b

3-Fluoroquinolin-6-ol 24a (489 mg, 3 mmol, prepared according to the known method disclosed in "*Synlett*, 2014, 25(6), 858-862") and pyridine (474 mg, 6 mmol) were dissolved in 10 mL of dichloromethane. The reaction solution was added dropwise with trifluoromethanesulfonic anhydride (0.55 mL, 3.3 mmol) at 0° C., and stirred for 2 hours. The reaction solution was added with water, and extracted with dichloromethane (20 mL×3). The organic phases were combined, washed with saturated sodium chloride solution (20 mL), dried over anhydrous sodium sulfate, and filtrated. The filtrate was concentrated under reduced pressure, and the residue was purified by CombiFlash rapid preparation instrument with elution system B to obtain the title product 24b (520 mg), yield: 58.7%.

MS m/z (ESI): 296.4 [M+1].

Step 2

3-Fluoro-6-(4,4,5,5-tetramethyl-1,3,2-dioxaborolan-2-yl)quinoline 24c

Compound 24b (100 mg, 0.34 mmol), bis(pinacolato)diboron (103 mg, 0.4 mmol), [1,1'-bis(diphenylphosphino)ferrocene]dichloropalladium (50 mg, 0.068 mmol) and potassium acetate (100 mg, 1 mmol) were dissolved successively in 20 mL of dimethyl ether under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 24c (70 mg), yield: 76%.

MS m/z (ESI): 274.4 [M+1].

Step 3

6-(3-Fluoroquinolin-6-yl)-5-phenyl-1,2,4-triazin-3-amine 24

Compound 24c (70 mg, 0.26 mmol), compound 1c (64 mg, 0.26 mmol), [1,1'-bis(diphenylphosphino)ferrocene]dichloropalladium (37 mg, 0.05 mmol) and potassium carbonate (106 mg, 0.77 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 24 (20 mg), yield: 25%.

MS m/z (ESI): 318.4 [M+1].

$^1$H NMR (400 MHz, DMSO-$d_6$) δ 8.94-8.95 (m, 1H), 8.26-8.29 (m, 1H), 8.17 (m, 1H), 7.92-7.95 (d, 1H), 7.51-7.55 (m, 3H), 7.41-7.44 (m, 3H), 7.34-7.36 (m, 2H).

Example 25

6-(8-Methoxyquinolin-6-yl)-5-phenyl-1,2,4-triazin-3-amine 25

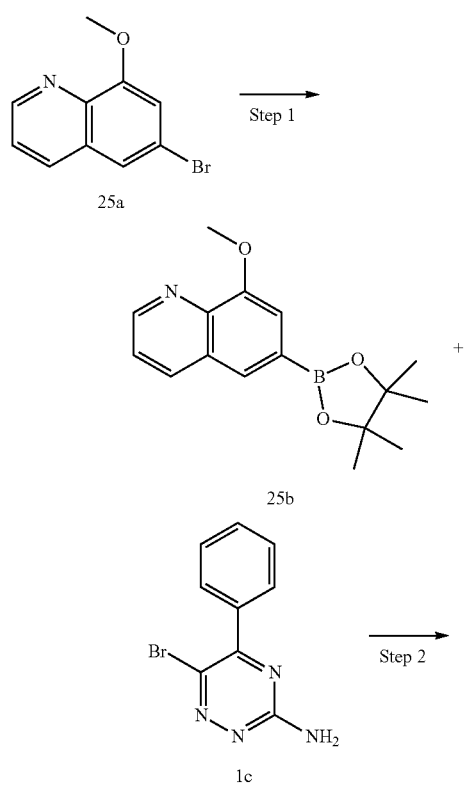

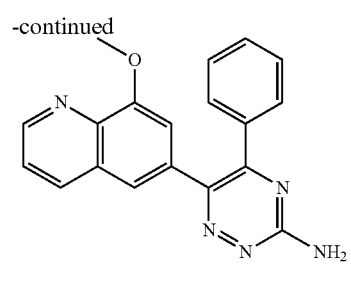

Step 1

8-Methoxy-6-(4,4,5,5-tetramethyl-1,3,2-dioxaborolan-2-yl)quinoline 25b

6-Bromo-8-methoxyquinoline 25a (530 mg, 2.2 mmol, prepared according to the known method disclosed in "*Journal of the American Chemical Society*, 2005, 127(1), 74-75"), bis(pinacolato)diboron (845 mg, 3.3 mmol), [1,1'-bis(diphenylphosphino)ferrocene]dichloropalladium (162 mg, 0.22 mmol) and potassium acetate (652 mg, 6.65 mmol) were dissolved successively in 10 mL of 1,4-dioxane under an argon atmosphere. The reaction solution was heated to 80° C., and stirred for 3 hours. The reaction was stopped, and the reaction solution was cooled to room temperature and filtrated through celite. The filter cake was washed with ethyl acetate, and the filtrate was concentrated under reduced pressure. The residue was purified by CombiFlash rapid preparation instrument with elution system B to obtain the title product 25b (410 mg), yield: 65%.

MS m/z (ESI): 286.1 [M+1].

Step 2

6-(8-Methoxyquinolin-6-yl)-5-phenyl-1,2,4-triazin-3-amine 25

Compound 25b (100 mg, 0.37 mmol), compound 1c (93 mg, 0.37 mmol), [1,1'-bis(diphenylphosphino)ferrocene]dichloropalladium (27 mg, 0.037 mmol) and potassium carbonate (10 mg, 0.074 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature, added with water, and extracted with ethyl acetate three times. The organic phases were combined, washed with saturated sodium chloride solution, dried over anhydrous sodium sulfate, and filtrated. The filtrate was concentrated under reduced pressure, and the residue was purified by preparative high performance liquid chromatography (Waters 2767-SQ Detecor2, elution system: ammonium bicarbonate, water, acetonitrile) to obtain the title product 25 (25 mg), yield: 21%.

MS m/z (ESI): 330.4 [M+1].

$^1$H NMR (400 MHz, DMSO-$d_6$) δ 8.82 (d, 1H), 8.25 (d, 1H), 7.62 (s, 1H), 7.51-7.53 (m, 3H), 7.42-7.44 (m, 3H), 7.34-7.36 (m, 2H), 7.98 (s, 1H), 3.65 (s, 3H).

Example 26

5-(3-Fluorophenyl)-6-(8-fluoroquinolin-6-yl)-1,2,4-triazin-3-amine 26

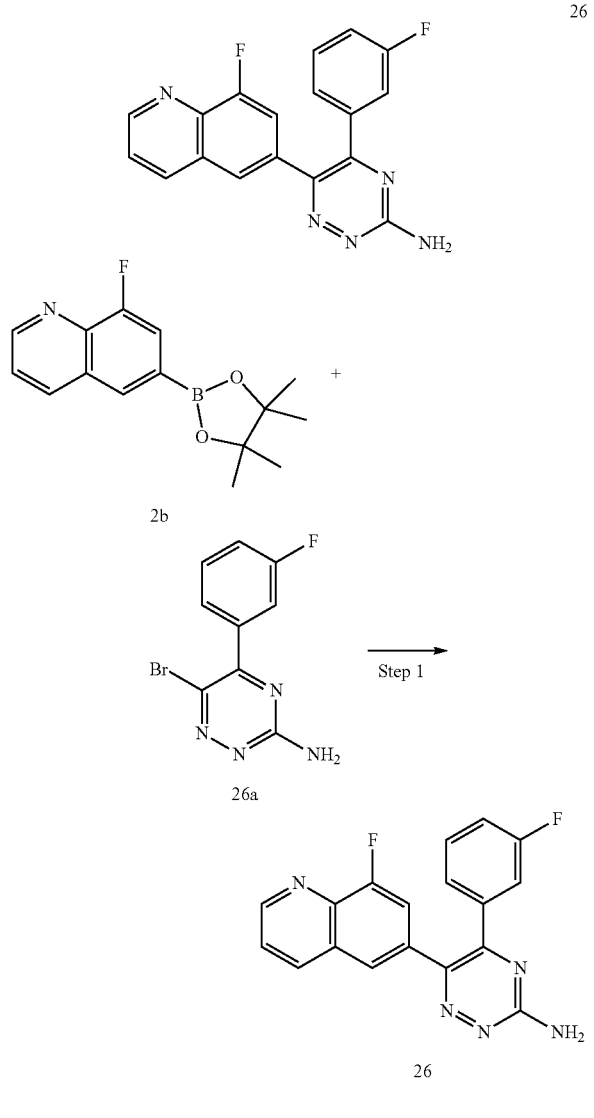

Compound 2b (101.50 mg, 371.65 µmol), 6-bromo-5-(3-fluorophenyl)-1,2,4-triazin-3-amine 26a (100 mg, 71.65 µmol, prepared according to the known method disclosed in "*Journal of Medicinal Chemistry*, 2012, 55(5), 1898-1903"), [1,1'-bis(diphenylphosphino)ferrocene]dichloropalladium (54.39 mg, 74.33 µmol) and potassium carbonate (153.86 mg, 1.11 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 26 (45 mg), yield: 36.11%.

MS m/z (ESI): 336.4 [M+1].

$^1$H NMR (400 MHz, DMSO-d$_6$) δ 8.94 (m, 1H), 8.37-8.39 (m, 1H), 7.88 (s, 1H), 7.53-7.61 (m, 3H), 7.44-7.47 (m, 1H), 7.26-7.35 (m, 3H), 7.15-7.17 (m, 1H).

Example 27

6-(4-Chloroquinolin-6-yl)-5-(4-fluorophenyl)-1,2,4-triazin-3-amine 27

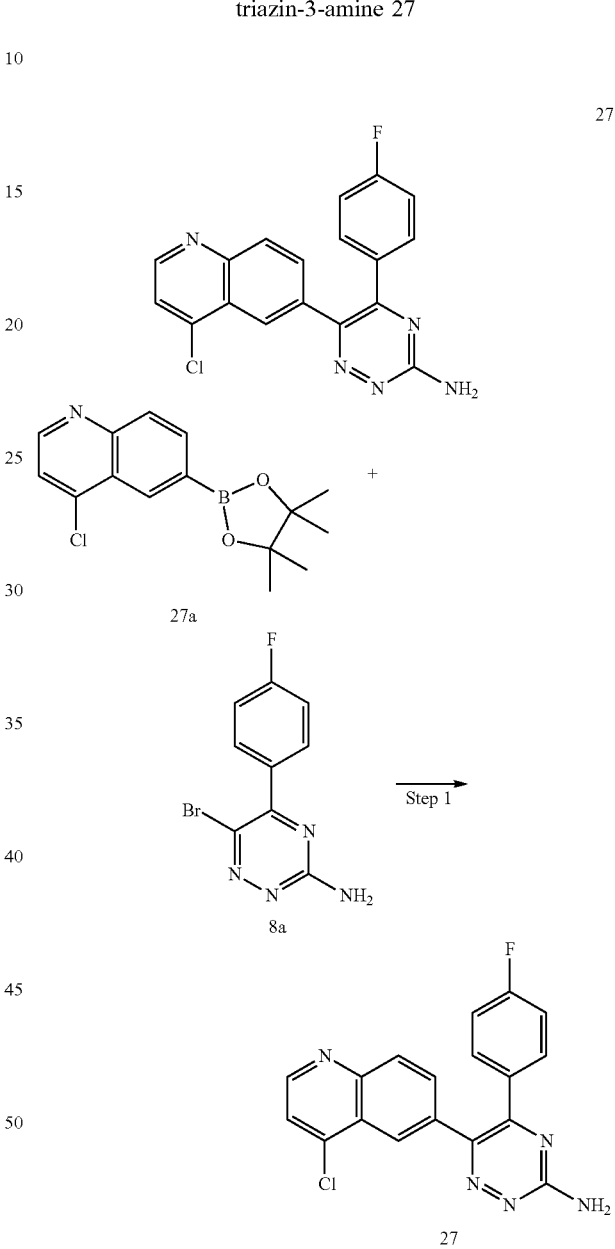

4-Chloro-6-(4,4,5,5-tetramethyl-1,3,2-dioxaborolan-2-yl)quinolone 27a (200 mg, 690.69 µmol, prepared according to the known method disclosed in "*Journal of Medicinal Chemistry*, 2011, 54(13), 4735-4751"), compound 8a (123.90 mg, 460.46 µmol), [1,1'-bis(diphenylphosphino)ferrocene]dichloropalladium (67.38 mg, 92.09 µmol) and potassium carbonate (190.63 mg, 1.38 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 27 (25 mg), yield: 15.43%.

MS m/z (ESI): 352.4 [M+1].

$^1$H NMR (400 MHz, DMSO-$d_6$) δ 8.85-8.86 (m, 1H), 8.26 (m, 1H), 8.02-8.04 (d, 1H), 7.76-7.79 (m, 2H), 7.60 (m, 2H), 7.48-7.52 (m, 2H), 7.19-7.23 (m, 2H).

Example 28

6-(3-Methylquinolin-6-yl)-5-phenyl-1,2,4-triazin-3-amine 28

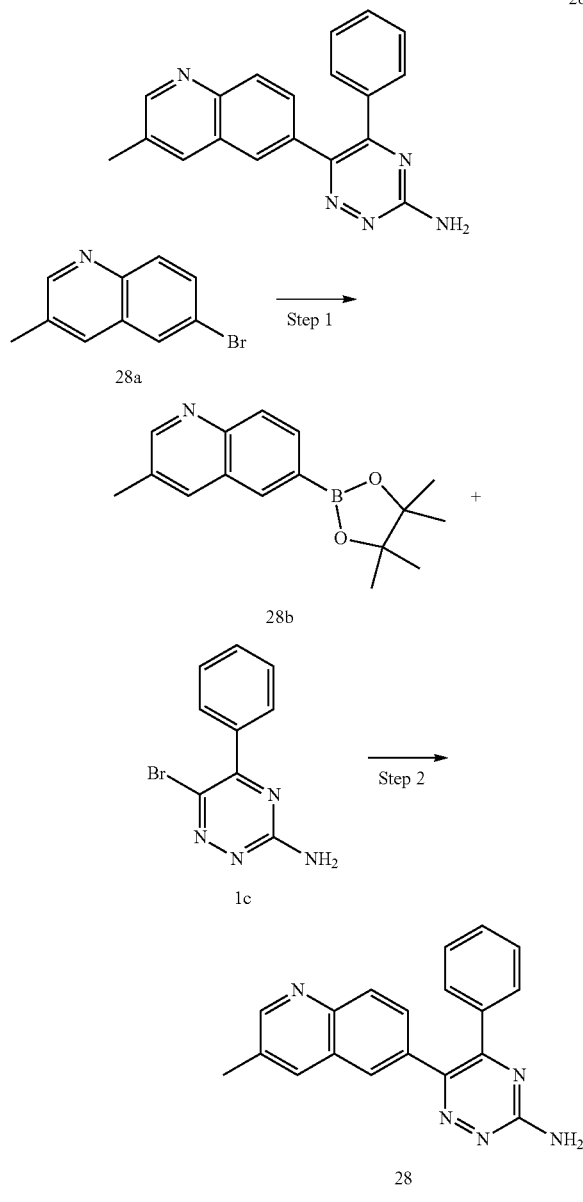

Step 1

3-Methyl-6-(4,4,5,5-tetramethyl-1,3,2-dioxaborolan-2-yl)quinoline 28b

6-Bromo-3-methylquinoline 28a (250 mg, 1.13 mmol, prepared according to the method disclosed in the patent application "WO2006132739A2"), bis(pinacolato)diboron (429 mg, 1.69 mmol), [1,1'-bis(diphenylphosphino)ferrocene]dichloropalladium (165 mg, 0.225 mmol) and potassium acetate (331 mg, 3.38 mmol) were dissolved successively in 20 mL of dimethyl ether under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system B to obtain the title product 28b (240 mg), yield: 79.2%.

MS m/z (ESI): 270.1 [M+1].

Step 2

6-(3-Methylquinolin-6-yl)-5-phenyl-1,2,4-triazin-3-amine 28

Compound 28b (107 mg, 0.4 mmol), compound 1c (100 mg, 0.4 mmol), [1,1'-bis(diphenylphosphino)ferrocene]dichloropalladium (58 mg, 0.08 mmol) and potassium carbonate (165 mg, 1.20 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 28 (50 mg), yield: 40%.

MS m/z (ESI): 314.1 [M+1].

$^1$H NMR (400 MHz, DMSO-$d_6$) δ 8.76-8.77 (m, 1H), 7.06 (s, 1H), 7.95-7.96 (m, 1H), 7.85-7.87 (d, 1H), 7.51-7.55 (m, 3H), 7.41-7.43 (m, 3H), 7.32-7.34 (m, 2H), 2.47 (s, 3H).

Example 29

5-Phenyl-6-(quinazolin-6-yl)-1,2,4-triazin-3-amine 29

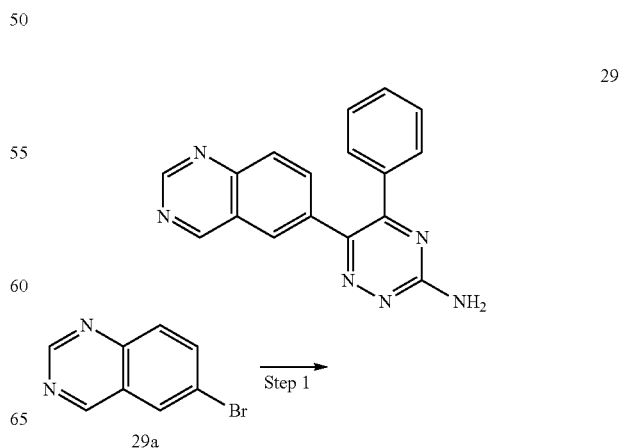

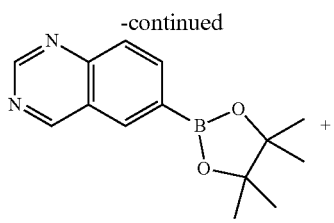

29b

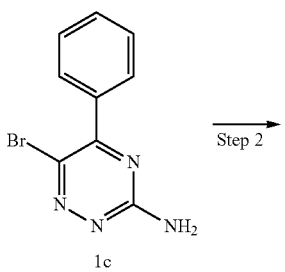

1c

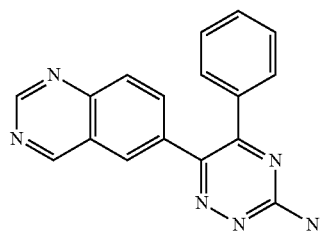

29

Step 1

6-(4,4,5,5-Tetramethyl-1,3,2-dioxaborolan-2-yl)quinazoline 29b

6-Bromoquinazoline 29a (418 mg, 2 mmol, prepared according to the known method disclosed in "*Science of Synthesis,* 2004, 16, 573-749"), bis(pinacolato)diboron (609 mg, 7.4 mmol), [1,1'-bis(diphenylphosphino)ferrocene]dichloropalladium (292 mg, 0.40 mmol) and potassium acetate (588 mg, 6.00 mmol) were dissolved successively in 20 mL of dimethyl ether under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 29b (450 mg), yield: 87.9%.

MS m/z (ESI): 257.1 [M+1].

Step 2

5-Phenyl-6-(quinazolin-6-yl)-1,2,4-triazin-3-amine 29

Compound 29b (81 mg, 0.32 mmol), compound 1c (80 mg, 0.32 mmol), [1,1'-bis(diphenylphosphino)ferrocene]dichloropalladium (47 mg, 0.064 mmol) and potassium carbonate (132 mg, 0.96 mmol) were dissolved successively in 12 mL of a mixed solution of 1,4-dioxane and water (V/V=5: 1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 29 (10 mg), yield: 5.1%.

MS m/z (ESI): 301.4 [M+1].

$^1$H NMR (400 MHz, DMSO-$d_6$) δ 9.60 (s, 1H), 9.30 (s, 1H), 8.31 (s, 1H), 7.89-7.91 (d, 1H), 7.80-7.82 (m, 1H), 7.60 (m, 2H), 7.42-7.44 (m, 3H), 7.34-7.36 (m, 2H).

Example 30

5-(4-Fluorophenyl)-6-(quinolin-6-yl)-1,2,4-triazin-3-amine 30

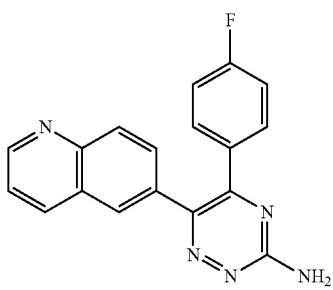

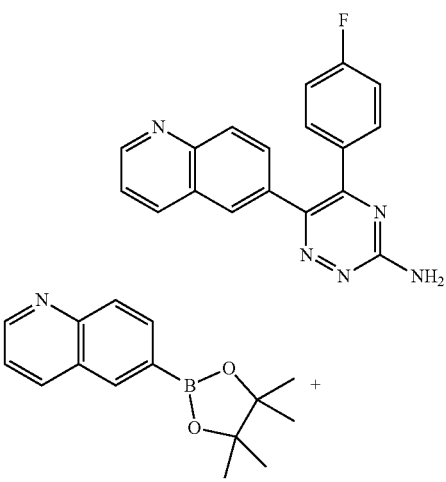

3b

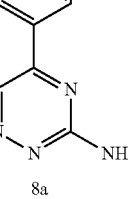

8a

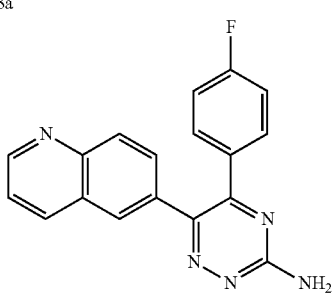

30

Compound 3b (94.81 mg, 371.65 μmol), compound 8a (100 mg, 371.65 μmol), [1,1'-bis(diphenylphosphino)ferrocene]dichloropalladium (54.39 mg, 74.33 μmol) and potassium carbonate (153.86 mg, 1.11 mmol) were dissolved in 12 mL of a mixed solution of 1,4-dioxane and water (V/V=5: 1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 30 (5 mg), yield: 4.24%.

MS m/z (ESI): 318.1 [M+1].

$^1$H NMR (400 MHz, DMSO-$d_6$) δ 8.91-8.92 (m, 1H), 8.36-8.38 (d, 1H), 8.11-8.12 (m, 1H), 7.92-7.94 (d, 1H), 7.47-7.59 (m, 6H), 7.17-7.21 (m, 2H).

Example 31

6-(8-Fluoro-4-methylquinolin-6-yl)-5-(2-fluorophenyl)-1,2,4-triazin-3-amine 31

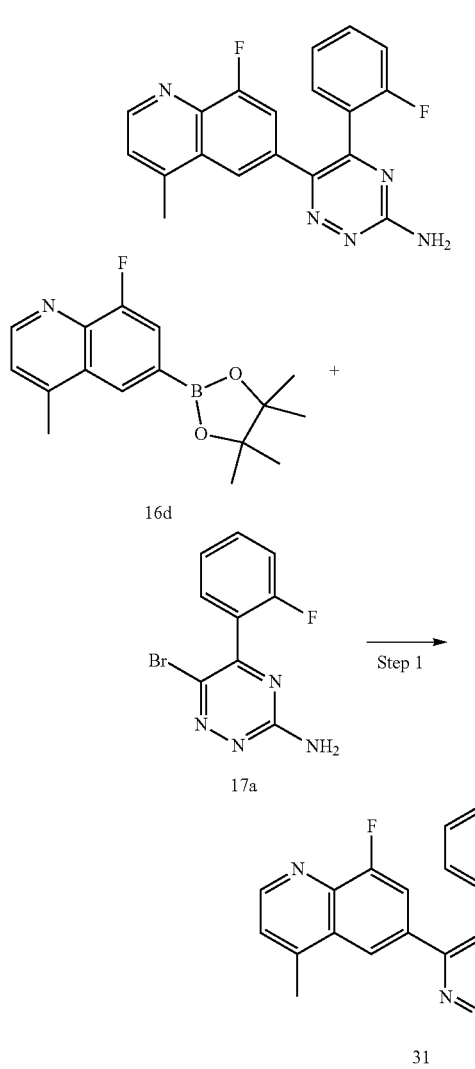

Compound 17a (100 mg, 371.65 μmol), compound 16d (106.71 mg, 371.65 μmol), [1,1'-bis(diphenylphosphino)ferrocene]dichloropalladium (54.39 mg, 74.33 μmol) and potassium carbonate (153.86 mg, 1.11 mmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 31 (50 mg), yield: 38.51%.

MS m/z (ESI): 350.4 [M+1].

$^1$H NMR (400 MHz, DMSO-$d_6$) δ 8.74-8.75 (m, 1H), 7.67-7.69 (m, 4H), 7.59 (s, 1H), 7.50-7.52 (m, 1H), 7.36-7.41 (m, 2H), 7.09-7.11 (m, 1H), 2.31 (s, 3H).

Example 32

5-(4-Fluorophenyl)-6-(8-fluoroquinolin-6-yl)-1,2,4-triazin-3-amine 32

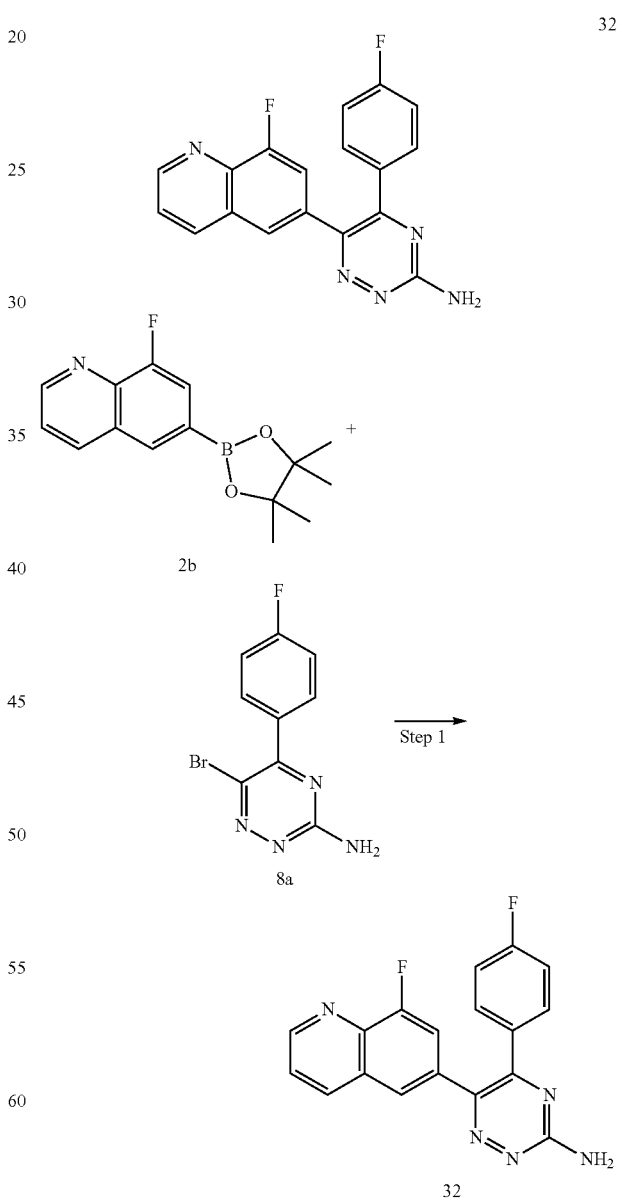

Compound 8a (100 mg, 371.65 μmol), compound 2b (101.50 mg, 371.65 μmol), [1,1'-bis(diphenylphosphino)ferrocene]dichloropalladium (54.39 mg, 74.33 μmol) and potassium carbonate (153.86 mg, 1.11 mmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A. The resulting crude product was purified by thin layer chromatography with developing solvent system D to obtain the title product 32 (20 mg), yield: 16.05%.

MS m/z (ESI): 336.1 [M+1].

$^1$H NMR (400 MHz, DMSO-d$_6$) δ 8.96-8.97 (m, 1H), 8.41-8.43 (d, 1H), 7.91 (s, 1H), 7.64-7.66 (m, 1H), 7.63 (m, 2H), 7.46-7.52 (m, 3H), 7.19-7.24 (m, 2H).

Example 33

5-(2,4-Difluorophenyl)-6-(4-methylquinazolin-6-yl)-1,2,4-triazin-3-amine 33

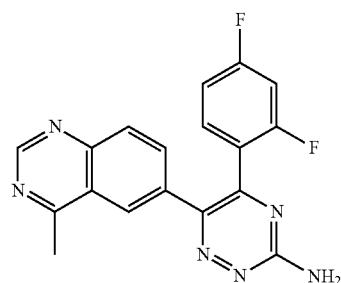

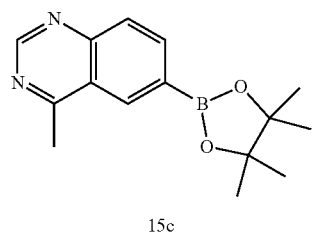

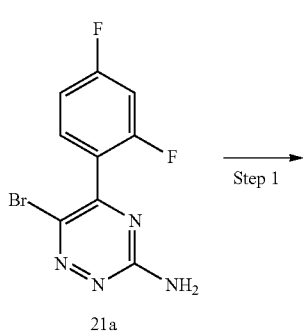

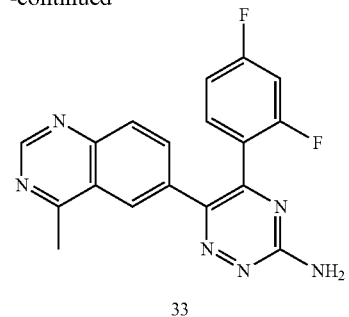

Compound 21a (100 mg, 349.56 μmol), compound 15c (94.43 mg, 349.56 μmol), [1,1'-bis(diphenylphosphino)ferrocene]dichloropalladium (51.16 mg, 69.91 μmol) and potassium carbonate (144.72 mg, 1.05 mmol) were dissolved in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 33 (55 mg), yield: 44.91%.

MS m/z (ESI): 351.4 [M+1].

$^1$H NMR (400 MHz, DMSO-d$_6$) δ 9.11 (s, 1H), 8.10 (s, 1H), 8.02-8.04 (d, 1H), 7.94-7.96 (d, 1H), 7.72-7.79 (m, 3H), 7.25-7.35 (m, 1H), 7.15-7.25 (m, 1H), 2.68 (s, 3H).

Example 34

6-(3-Methoxyquinolin-6-yl)-5-phenyl-1,2,4-triazin-3-amine 34

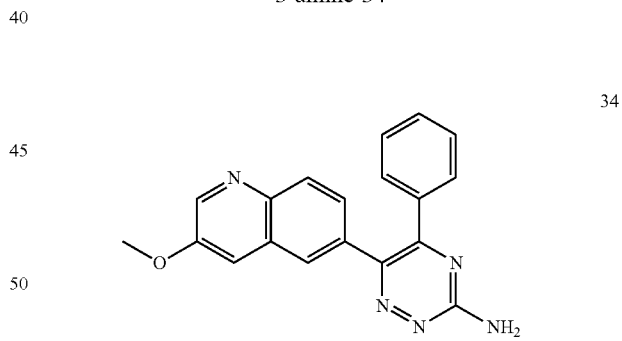

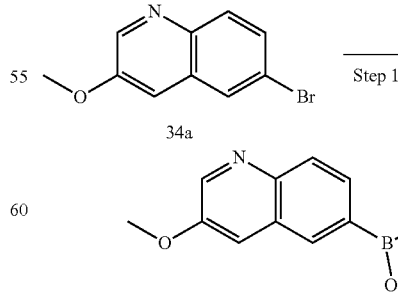

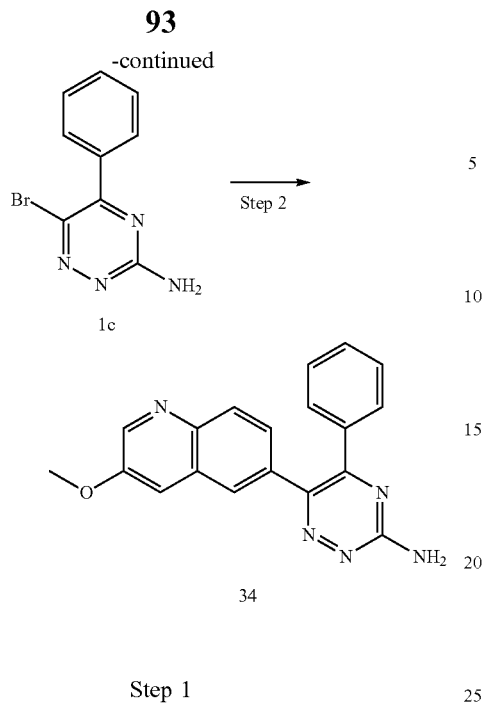

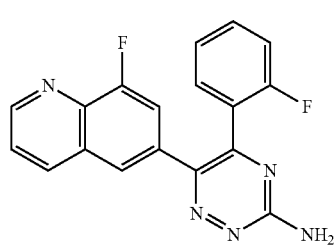

Step 1

3-Methoxy-6-(4,4,5,5-tetramethyl-1,3,2-dioxaborolan-2-yl)quinoline 34b

6-Bromo-3-methoxyquinoline 34a (120 mg, 0.5 mmol, prepared according to the method disclosed in the patent application "WO2012009194A1"), bis(pinacolato)diboron (192 mg, 0.76 mmol), [1,1'-bis(diphenylphosphino)ferrocene]dichloropalladium (74 mg, 0.1 mmol) and potassium acetate (148 mg, 1.5 mmol) were dissolved successively in 15 mL of dimethyl ether under an argon atmosphere. The reaction solution was heated to 80° C., and stirred for 4 hours. The reaction was stopped, and the reaction solution was cooled to room temperature and filtrated. The filtrate was concentrated under reduced pressure, and the residue was purified by CombiFlash rapid preparation instrument with elution system B to obtain the title product 34b (90 mg), yield: 62.9%.

MS m/z (ESI): 286.1 [M+1].

Step 2

6-(3-Methoxyquinolin-6-yl)-5-phenyl-1,2,4-triazin-3-amine 34

Compound 34b (79 mg, 0.279 mmol), compound 1c (70 mg, 0.279 mmol), [1,1'-bis(diphenylphosphino)ferrocene]dichloropalladium (41 mg, 0.056 mmol) and potassium carbonate (115 mg, 0.84 mmol) were dissolved successively in 12 mL of a mixed solution of 1,4-dioxane and water (V/V=5:1) under an argon atmosphere. The reaction solution was heated to 80° C., and stirred for 2 hours. The reaction was stopped, and the reaction solution was cooled to room temperature and filtrated. The filtrate was concentrated under reduced pressure, and the residue was purified by CombiFlash rapid preparation instrument with elution system A to obtain the title product 34 (30 mg), yield: 33%.

MS m/z (ESI): 330.4 [M+1].

¹H NMR (400 MHz, DMSO-d₆) δ 8.64-8.65 (m, 1H), 8.03-8.04 (m, 1H), 7.81-7.83 (d, 1H), 7.75-7.76 (m, 1H), 7.51 (m, 2H), 7.42-7.45 (m, 3H), 7.33-7.35 (m, 3H), 3.91 (s, 3H).

Example 35

5-(2-Fluorophenyl)-6-(8-fluoroquinolin-6-yl)-1,2,4-triazin-3-amine 35

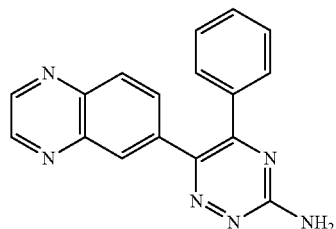

In accordance with the synthetic route of Example 32, the starting compound 8a in Step 1 was replaced with compound 17a, accordingly, the title product 35 (61 mg) was prepared.

MS m/z (ESI): 336.4 [M+1].

¹H NMR (400 MHz, DMSO-d₆) δ 8.90-8.91 (m, 1H), 8.29-8.31 (d, 1H), 7.77 (s, 1H), 7.60-7.66 (m, 3H), 7.58-7.59 (m, 1H), 7.42-7.49 (m, 2H), 7.11-7.34 (m, 1H), 7.08-7.11 (m, 1H).

Example 36

5-Phenyl-6-(quinoxalin-6-yl)-1,2,4-triazin-3-amine 36

In accordance with the synthetic route of Example 23, the starting compound 23a in Step 1 was replaced with 6-(4,4,5,5-tetramethyl-1,3,2-dioxaborolan-2-yl)quinoxaline 36a (prepared according to the known method disclosed in "Organic Letters, 2009, 11(13), 2860-2863"), accordingly, the title product 36 (20 mg) was prepared.

MS m/z (ESI): 301.4 [M+1].

¹H NMR (400 MHz, DMSO-d₆) δ 8.92-8.94 (m, 2H), 8.03-8.05 (m, 2H), 7.82-7.85 (m, 1H), 7.60 (m, 2H), 7.43-7.46 (m, 3H), 7.34-7.36 (m, 2H).

Example 37

6-(2-Methylquinolin-6-yl)-5-phenyl-1,2,4-triazin-3-amine 37

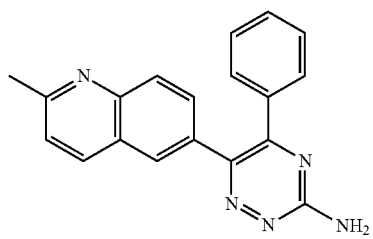

In accordance with the synthetic route of Example 23, the starting compound 23a in Step 1 was replaced with 2-methyl-6-(4,4,5,5-tetramethyl-1,3,2-dioxaborolan-2-yl)quinoline 37a (prepared according to the known method disclosed in "*Journal of the American Chemical Society*, 2015, 137(4), 1593-1600"), accordingly, the title product 37 (20 mg) was prepared.

MS m/z (ESI): 314.4 [M+1].

$^1$H NMR (400 MHz, DMSO-d$_6$) δ 8.19-8.21 (d, 1H), 8.02 (s, 1H), 7.78-7.80 (d, 1H), 7.50-7.53 (m, 3H), 7.40-7.43 (m, 4H), 7.32-7.34 (m, 2H), 2.65 (s, 3H).

Example 38

6-(3-Amino-5-phenyl-1,2,4-triazin-6-yl)quinoline-8-carbonitrile 38

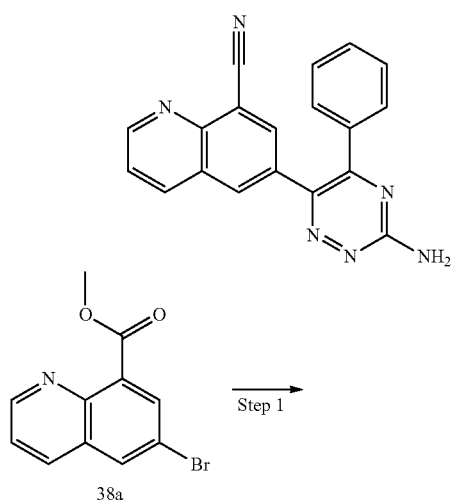

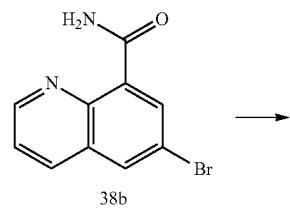

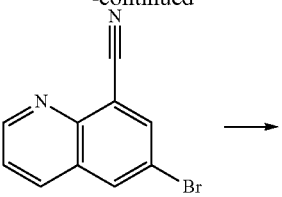

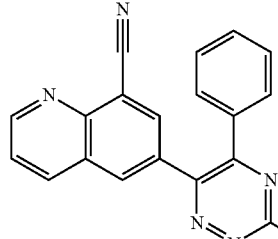

Step 1

6-Bromoquinoline-8-carboxamide 38b

Methyl 6-bromoquinoline-8-carboxylate 38a (400 mg, 1.5 mmol, prepared according to the method disclosed in the patent application "WO2011020193A1") was dissolved in 15 mL of methanol. The reaction solution was added dropwise with 5 mL of 40% aqueous ammonia, and stirred overnight. The reaction solution was added with water, and extracted with ethyl acetate three times. The organic phases were combined, washed with saturated sodium chloride solution, dried over anhydrous sodium sulfate, and filtrated. The filtrate was concentrated under reduced pressure, and the residue was purified by silica gel column chromatography with elution system B to obtain the title product 38b (280 mg), yield: 74%.

MS m/z (ESI): 251.0 [M+1].

Step 2

6-Bromoquinoline-8-carbonitrile 38c

Compound 38b (190 mg, 0.76 mmol) was dissolved in 20 mL of dichloromethane. The reaction solution was added successively with triethylamine (115 mg, 1.14 mmol) and trifluoroacetic anhydride (238 mg, 1.14 mmol), and stirred for 2 hours. The reaction solution was added with water, and extracted with dichloromethane three times. The organic phases were combined, washed with saturated sodium chloride solution, dried over anhydrous sodium sulfate, and filtrated. The filtrate was concentrated under reduced pressure, and the residue was pulped in methanol and filtrated. The filter cake was collected to obtain the title compound (180 mg), yield: 100%.

MS m/z (ESI): 232.9 [M+1].

In accordance with the similar synthetic route of Example 11, the starting compound 11b in Step 2 was replaced with 38c, accordingly, the title product 38 (25 mg) was prepared.

MS m/z (ESI): 325.4 [M+1].

$^1$H NMR (400 MHz, DMSO-d$_6$) δ 9.08 (d, 1H), 8.51 (d, 1H), 8.45 (s, 1H), 8.13 (s, 1H), 7.73 (d, 1H), 7.71 (brs, 2H), 7.43-7.45 (m, 3H), 7.36-7.38 (m, 2H).

Example 39

6-(3-Morpholinoquinolin-6-yl)-5-phenyl-1,2,4-triazin-3-amine 39

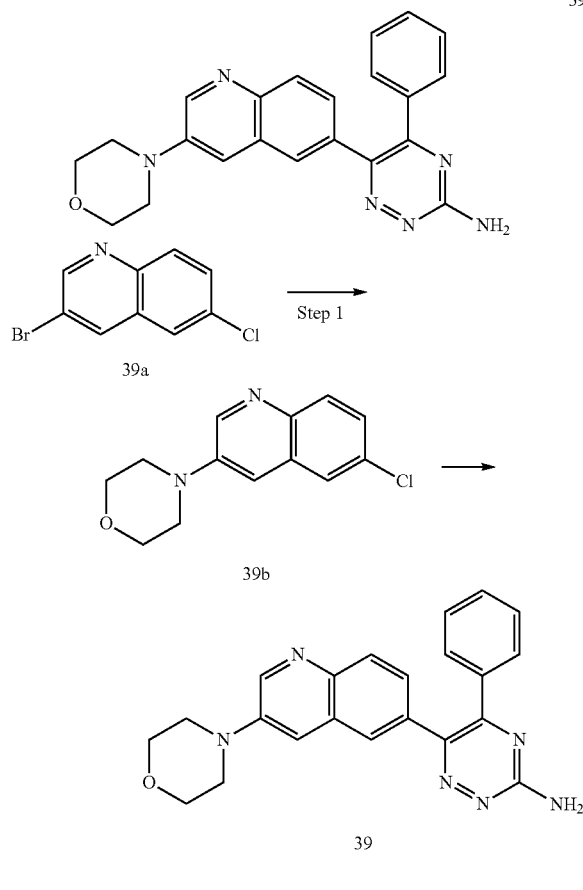

Step 1

4-(6-Chloroquinolin-3-yl)morpholine 39b

3-Bromo-6-chloroquinoline 39a (266 mg, 1.1 mmol, prepared according to the known method disclosed in "*Journal of Heterocyclic Chemistry*, 2015, 52(4), 1019-1025"), morpholine (87 mg, 1 mmol), palladium acetate (12 mg, 0.05 mmol), (±)-2,2'-bis-(diphenylphosphino)-1,1'-binaphthalene (31 mg, 0.05 mmol) and cesium carbonate (652 mg, 2 mmol) were dissolved in 10 mL of tetrahydrofuran under an argon atmosphere. The reaction solution was heated to 70° C., and stirred overnight. The reaction was stopped, and the reaction solution was cooled to room temperature and filtrated. The filtrate was concentrated under reduced pressure, and the residue was purified by CombiFlash rapid preparation instrument with elution system A to obtain the title product 39b (180 mg), yield: 66.2%.

MS m/z (ESI): 249.7 [M+1].

In accordance with the similar synthetic route of Example 11, the starting compound 11b in Step 2 was replaced with 39b, accordingly, the title product 39 (25 mg) was prepared.

MS m/z (ESI): 385.2 [M+1].

$^1$H NMR (400 MHz, DMSO-$d_6$) δ 8.88 (s, 1H), 7.93 (s, 1H), 7.73-7.76 (d, 1H), 7.40-7.52 (m, 6H), 7.26-7.33 (m, 3H), 3.80 (m, 4H), 3.28 (m, 4H).

Example 40

6-(4-(Morpholinomethyl)quinolin-6-yl)-5-phenyl-1,2,4-triazin-3-amine 40

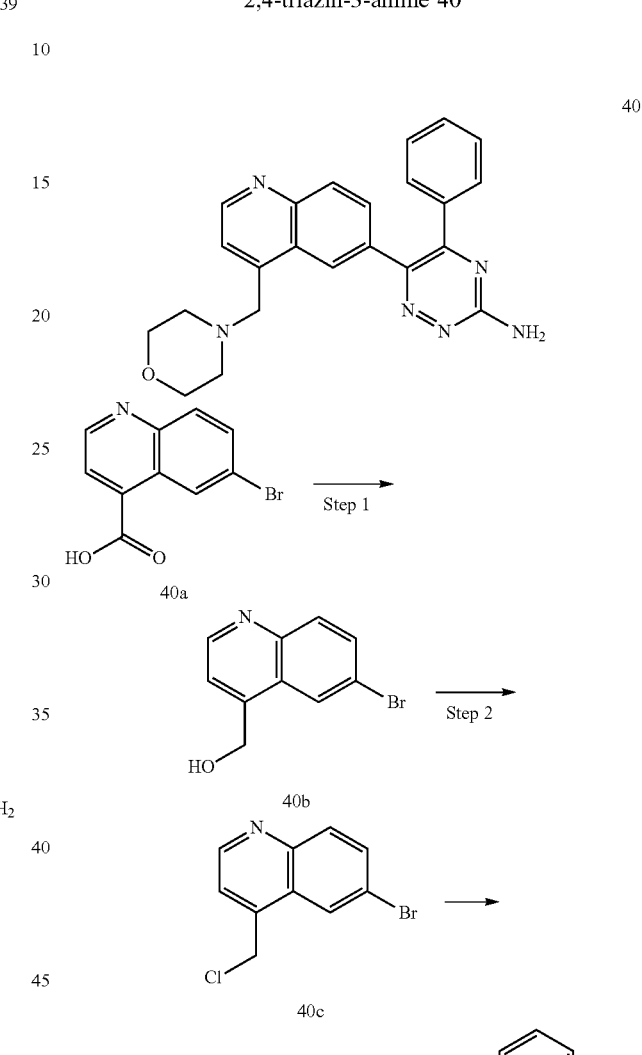

Step 1

(6-Bromoquinolin-4-yl)methanol 40b

Lithium aluminum hydride (150.76 mg, 3.97 mmol) was added to 50 mL of tetrahydrofuran. The reaction solution was added with 6-bromoquinoline-4-carboxylic acid 40a (1.0 g, 3.97 mmol, prepared according to the known method disclosed in "*Chinese Chemical Letters*, 2010, 21(1), 35-38") in batches at 0° C., and stirred for 2 hours. The reaction solution was added with 5 mL of water, and filtrated through celite. The filter cake was washed with ethyl acetate, and the filtrate was concentrated under reduced pressure. The residue was purified by CombiFlash rapid preparation instrument with elution system A to obtain the title product 40b (250 mg), yield: 26.5%.

Step 2

6-Bromo-4-(chloromethyl)quinoline 40c

Compound 40b (250 mg, 1.05 mmol) was added to 10 mL dichloromethane. The reaction solution was added with 2 mL of thionyl chloride, and stirred for 3 hours. The reaction solution was concentrated to dryness under reduced pressure, and the residue was purified by CombiFlash rapid preparation instrument with elution system A to obtain the title product 40c (180 mg), yield: 66.8%.

In accordance with the similar synthetic route of Example 39, the starting compound 39a in Step 1 was replaced with compound 40c, accordingly, the title product 40 (5 mg) was prepared.

MS m/z (ESI): 399.1 [M+1].

$^1$H NMR (400 MHz, DMSO-d$_6$) δ 8.82-8.83 (m, 1H), 8.16 (s, 1H), 7.98-8.00 (d, 1H), 7.86-7.88 (d, 1H), 7.53 (m, 2H), 7.42-7.47 (m, 4H), 7.35-7.37 (m, 2H), 3.61 (s, 2H), 3.49 (m, 4H), 2.30 (m, 4H).

Example 41

6-(3-(Morpholinomethyl)quinolin-6-yl)-5-phenyl-1,2,4-triazin-3-amine 41

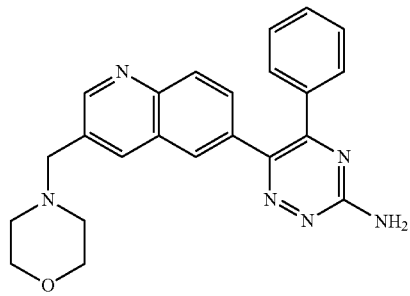

41

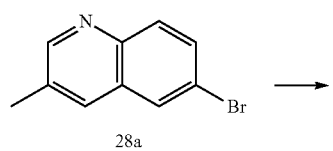

28a

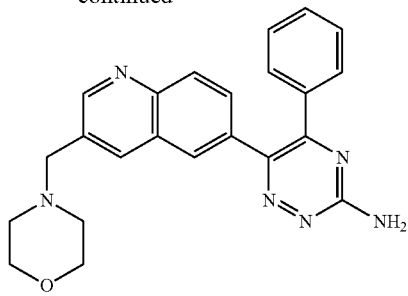

41

In accordance with the similar synthetic route of Example 40, the starting compound 40b in Step 2 was replaced with compound 28a, accordingly, the title product 41 (5 mg) was prepared.

MS m/z (ESI): 399.5 [M+1].

$^1$H NMR (400 MHz, DMSO-d$_6$) δ 8.82-8.83 (m, 1H), 8.16 (s, 1H), 8.01-8.06 (m, 1H), 7.84-7.86 (d, 1H), 7.48-7.50 (m, 3H), 7.37-7.41 (m, 3H), 7.30-7.32 (m, 2H), 3.64 (s, 2H), 3.56 (m, 4H), 2.39 (m, 4H).

Example 42

6-(3-Amino-5-phenyl-1,2,4-triazin-6-yl)quinoline-8-carboxamide 42

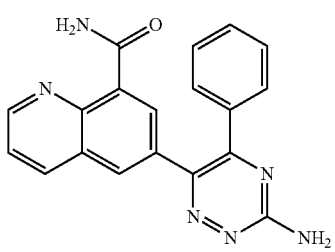

42

In accordance with the synthetic route of Example 14, the starting compound 14a in Step 1 was replaced with compound 38b, accordingly, the title product 42 (14 mg) was prepared.

MS m/z (ESI): 343.3 [M+1].

$^1$H NMR (400 MHz, DMSO-d$_6$) δ 10.16 (s, 1H), 9.01 (s, 1H), 8.55 (s, 1H), 8.45 (d, 1H), 8.19 (s, 1H), 7.90 (s, 1H), 7.64 (d, 1H), 7.58 (brs, 2H), 7.41-7.44 (m, 3H), 7.33-7.35 (m, 2H).

Example 43

6-(4-Morpholinoquinolin-6-yl)-5-phenyl-1,2,4-triazin-3-amine 43

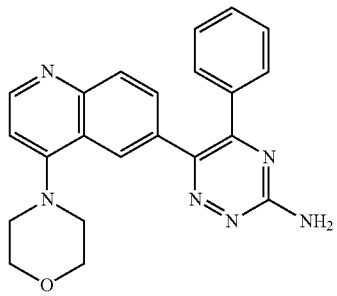

43

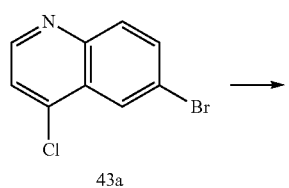

43a

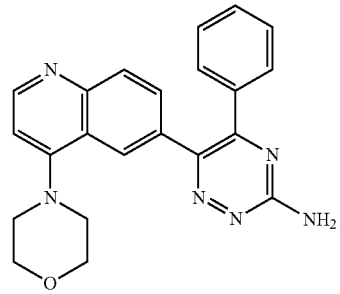

43

In accordance with the similar synthetic route of Example 39, the starting compound 39a in Step 1 was replaced with 6-bromo-4-chloroquinoline 43a (prepared according to the known method disclosed in "*Journal of Medicinal Chemistry*, 2015, 58(14), 5522-5537"), accordingly, the title compound 43 (50 mg) was prepared.

MS m/z (ESI): 385.2 [M+1].

$^1$H NMR (400 MHz, DMSO-d$_6$) δ 8.66-8.68 (m, 1H), 8.01-8.02 (m, 2H), 7.71 (s, 1H), 7.46-7.48 (m, 4H), 7.35-7.38 (m, 3H), 6.92-6.93 (m, 1H), 3.56-3.58 (m, 4H), 2.71-2.73 (m, 4H).

Example 44

6-(4-Ethylquinolin-6-yl)-5-(4-fluorophenyl)-1,2,4-triazin-3-amine 44

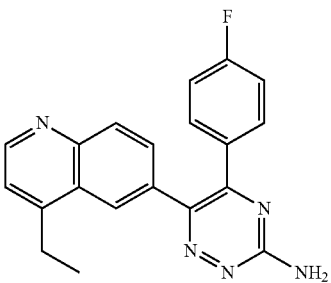

44

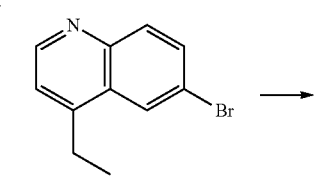

14a

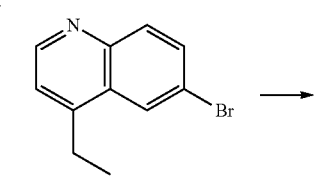

44a

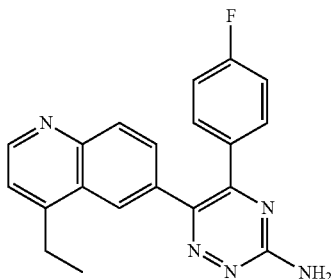

44

Step 1

6-Bromo-4-ethylquinoline 44a

Compound 14a (500 mg, 2.25 mmol) was dissolved in 50 mL of tetrahydrofuran. The reaction solution was added dropwise with diisopropylamino lithium (723.54 mg, 6.75 mmol) at −78° C., and stirred for 1 hour. The reaction solution was added with methyl iodide (3.20 g, 22.51 mmol), gradually warmed up to room temperature, and stirred overnight. The reaction solution was added with saturated aqueous ammonium chloride solution, and extracted with ethyl acetate three times. The organic phases were combined, washed with saturated sodium chloride solution once, dried over anhydrous sodium sulfate, and filtrated. The filtrate was concentrated under reduced pressure, and the residue was purified by CombiFlash rapid preparation instrument with elution system B to obtain the title product 44a (480 mg), yield: 90.3%.

In accordance with the similar synthetic route of Example 25, the starting compound 25a in Step 1 was replaced with compound 44a, and the starting compound 1c in Step 2 was replaced with compound 8a, accordingly, the title compound 44 (40 mg) was prepared.

MS m/z (ESI): 346.5 [M+1].

$^1$H NMR (400 MHz, DMSO-$d_6$) δ 8.78-8.79 (m, 1H), 7.98-8.03 (m, 2H), 7.81-7.83 (d, 1H), 7.47-7.51 (m, 4H), 7.36-7.37 (m, 1H), 7.17-7.22 (m, 2H), 2.88-2.90 (m, 2H), 1.05-1.09 (t, 3H).

Example 45

6-(8-Fluoro-4-methylquinazolin-6-yl)-5-phenyl-1,2,4-triazin-3-amine 45

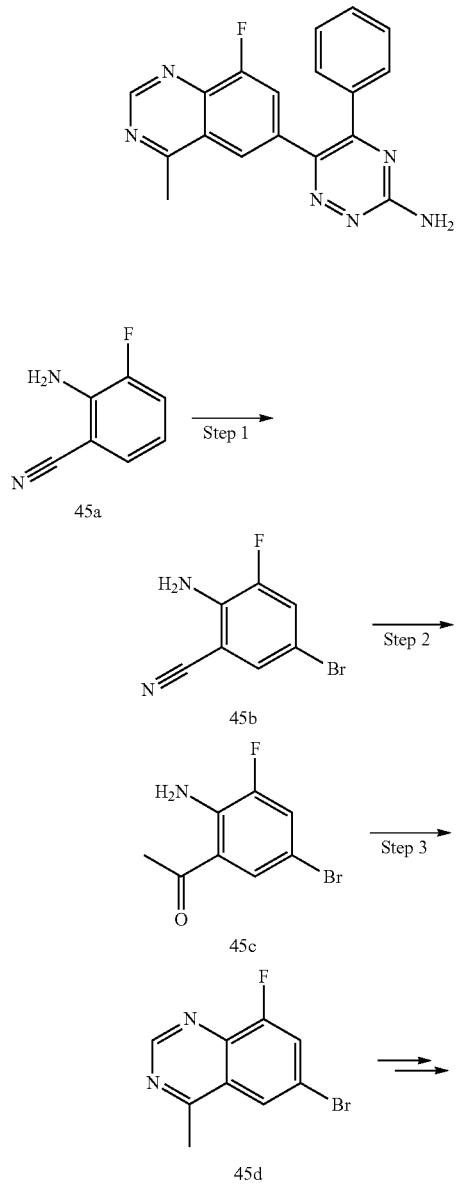

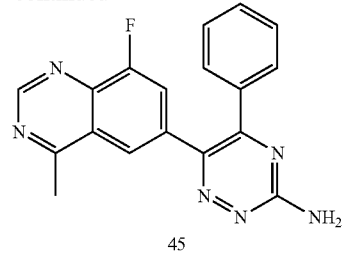

Step 1

2-Amino-5-bromo-3-fluorobenzonitrile 45b

2-Amino-3-fluorobenzonitrile 45a (1 g, 7.35 mmol, purchased from Shanghai Bide Pharmatech Ltd.) was dissolved in 50 mL of dichloromethane. The reaction solution was added with N-bromosuccinimide (1.37 g, 7.71 mmol), and stirred for 16 hours. The reaction solution was added with water, and extracted with dichloromethane (50 mL×3). The organic phases were combined, washed with saturated sodium chloride solution (20 mL), dried over anhydrous sodium sulfate, and concentrated under reduced pressure. The residue was purified by CombiFlash rapid preparation instrument with elution system B to obtain the title product 45b (1.25 g), yield: 79.13%.

MS m/z (ESI):215.0 [M+1].

Step 2

1-(2-Amino-5-bromo-3-fluorophenyl)ethan-1-one 45c

Compound 45b (1 g, 4.65 mmol) was dissolved in 60 mL of tetrahydrofuran. The reaction solution was added dropwise with methylmagnesium bromide (2.77 g, 23.25 mmol) at −10° C., and stirred for 4 hours. The reaction solution was added with water, and extracted with ethyl acetate (20 mL×3). The organic phases were combined, washed with saturated sodium chloride solution (20 mL), dried over anhydrous sodium sulfate, and concentrated under reduced pressure. The residue was purified by CombiFlash rapid preparation instrument with elution system B to obtain the title product 45c (900 mg), yield: 83.41%.

Step 3

6-Bromo-8-fluoro-4-methylquinazoline 45d

Compound 45c (0.9 g, 3.88 mmol), triethyl orthoformate (862 mg, 5.82 mmol) and ammonium acetate (448 mg, 5.82 mmol) were added to a 250 mL reaction flask. The reaction mixture was stirred at 110° C. for 2 hours, and then cooled. The residue was purified by CombiFlash rapid preparation instrument with elution system B to obtain the title product 45d (300 mg), yield: 32.09%.

MS m/z (ESI):241.0 [M+1].

In accordance with the synthetic route of Example 34, the starting compound 34a in Step 1 was replaced with compound 45d, accordingly, the title product 45 (40 mg, yield: 30.16%) was prepared.

MS m/z (ESI): 333.4 [M+1].

¹H NMR (400 MHz, DMSO-d₆) δ 9.16 (s, 1H), 8.03 (s, 1H), 7.76-7.79 (m, 1H), 7.65 (br, 2H), 7.44-7.46 (m, 3H), 7.38-7.40 (m, 2H), 2.72 (s, 3H).

Example 46

5-(4-Chlorophenyl)-6-(4-methylquinazolin-6-yl)-1,2,4-triazin-3-amine 46

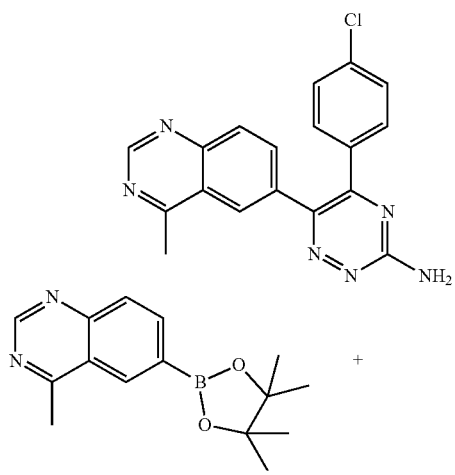

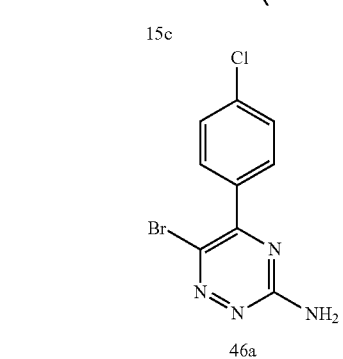

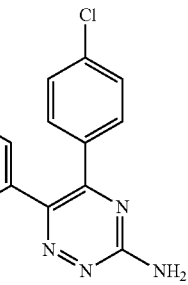

In accordance with the synthetic route of Example 15, the starting compound 1c in Step 3 was replaced with 6-bromo-5-(4-chlorophenyl)-1,2,4-triazin-3-amine 46a (prepared according to the method disclosed in the patent application "WO201195625A1"), accordingly, the title product 46 (42 mg, yield: 34.38%) was prepared.

MS m/z (ESI): 348.8 [M+1].

¹H NMR (400 MHz, DMSO-d₆) δ 9.12 (s, 1H), 8.30 (s, 1H), 7.87-7.90 (m, 2H), 7.62 (br, 2H), 7.45 (m, 4H), 2.79 (s, 3H).

Example 47

6-(4-Ethyl-8-fluoroquinolin-6-yl)-5-phenyl-1,2,4-triazin-3-amine 47

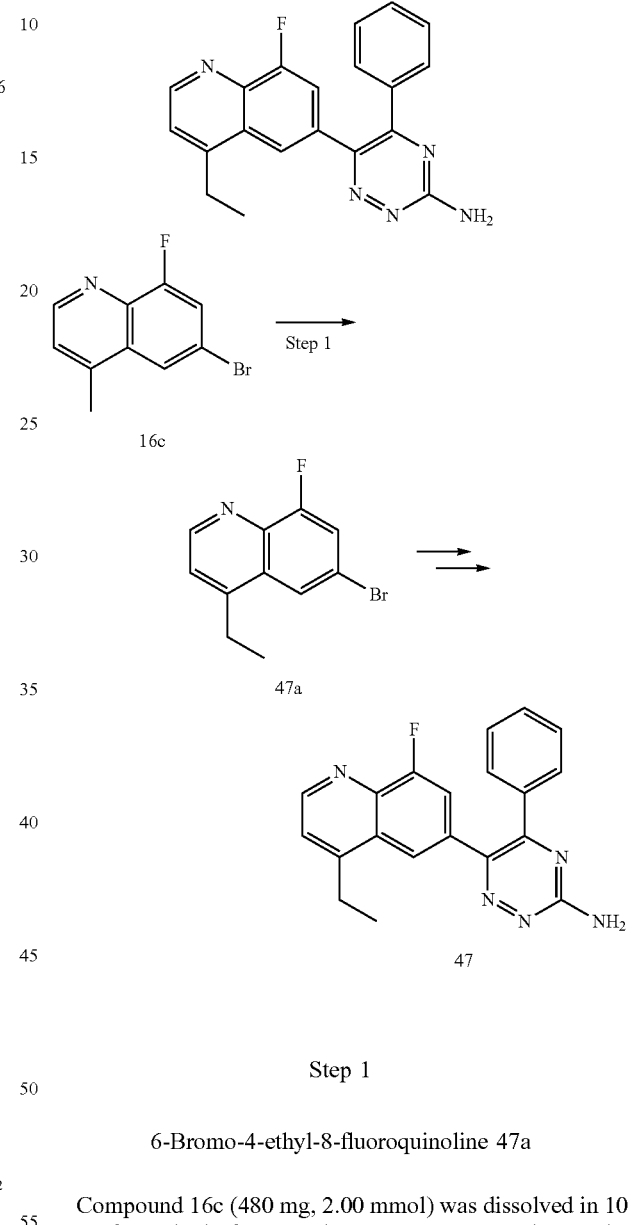

Step 1

6-Bromo-4-ethyl-8-fluoroquinoline 47a

Compound 16c (480 mg, 2.00 mmol) was dissolved in 10 mL of tetrahydrofuran under an argon atmosphere. The reaction solution was added dropwise with diisopropylamino lithium (257.02 mg, 2.40 mmol) at −78° C., and stirred for 1 hour. The reaction solution was then added with methyl iodide (297.98 mg, 2.10 mmol), and stirred for 2 hours. The reaction solution was added with water, and extracted with ethyl acetate (30 mL×3). The organic phases were combined, washed with saturated sodium chloride solution (20 mL), and dried over anhydrous sodium sulfate. The residue was purified by CombiFlash rapid preparation instrument with elution system B to obtain the title product 47a (120 mg), yield: 23.6%.

In accordance with the synthetic route of Example 14, the starting compound 14a in Step 1 was replaced with compound 47a, accordingly, the title product 47 (30 mg, yield: 37.37%) was prepared.

MS m/z (ESI): 346.5[M+1].

$^1$H NMR (400 MHz, DMSO-d$_6$) δ 8.81-8.82 (m, 1H), 7.79 (s, 1H), 7.58-7.66 (m, 1H), 7.47 (br, 2H), 7.36-7.45 (m, 6H), 2.81-2.82 (m, 2H), 0.99-1.03 (t, 3H).

Example 48

5-(2-Methylpyridin-4-yl)-6-(4-methylquinolin-6-yl)-1,2,4-triazin-3-amine 48

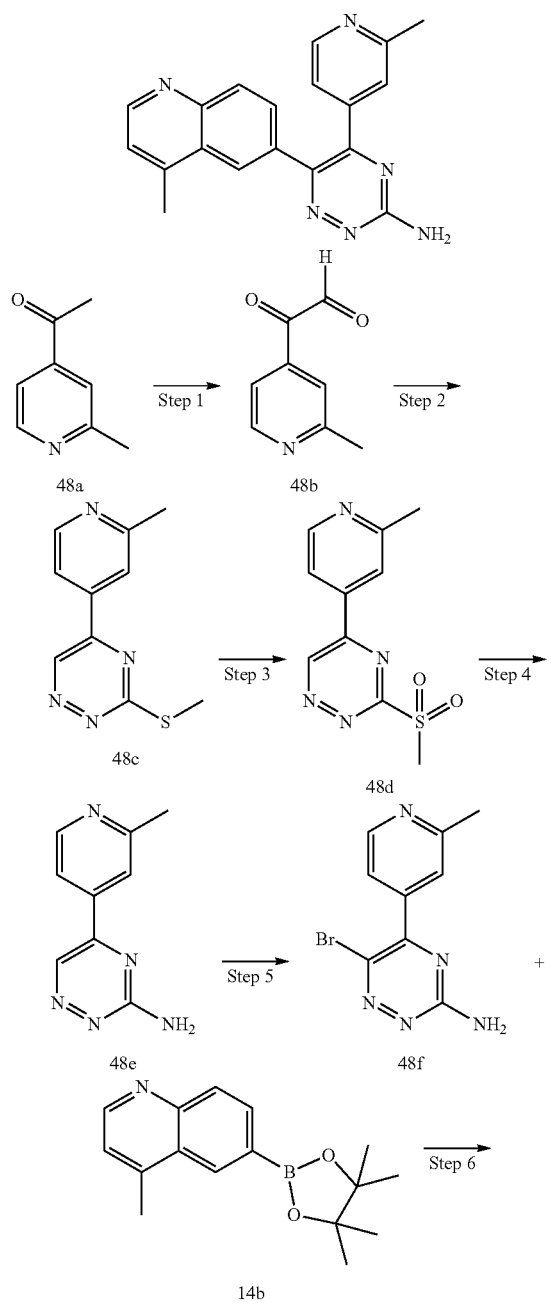

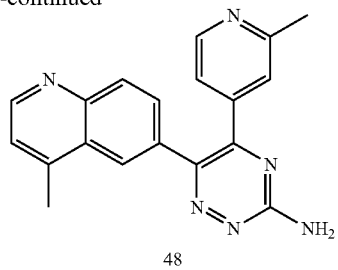

Step 1

2-(2-Methylpyridin-4-yl)-2-oxoacetaldehyde 48b 1-(2-Methylpyridin-4-yl)ethan-1-one 48a (4.29 g, 31.74 mmol, prepared according to the known method disclosed in "*Journal of Medicinal Chemistry*, 2015, 58(12), 5028-5037") was dissolved in 35 mL of dimethyl sulfoxide. The reaction solution was then added with 35 mL of hydrobromic acid, and stirred at 55° C. overnight. The reaction solution was used directly in the next step.

Step 2

5-(2-Methylpyridin-4-yl)-3-(methylthio)-1,2,4-triazine 48c

S-Methylisothiosemicarbazide hydroiodide (8.87 g, 38.06 mmol) and sodium bicarbonate (28 g, 333.31 mmol) were added to 300 mL of ethanol, followed by slow addition of the reaction solution containing the crude compound 48b (4.73 g, 31.71 mmol). After completion of the addition, the reaction solution was stirred at 80° C. for 1 hour. The reaction solution was concentrated under reduced pressure, added with water, and extracted with ethyl acetate (100 mL×2). The organic phases were combined, washed with water (80 mL×3) and saturated sodium chloride solution (80 mL), dried over anhydrous sodium sulfate, and concentrated under reduced pressure. The residue was purified by CombiFlash rapid preparation instrument with elution system A to obtain the title product 48c (5.6 g), yield: 80.90%.

MS m/z (ESI): 219.4[M+1].

Step 3

5-(2-Methylpyridin-4-yl)-3-methylsulfonyl-1,2,4-triazine 48d

Compound 48c (5.4 g, 24.74 mmol) was dissolved in 180 mL of dichloromethane, followed by addition of m-chloroperoxybenzoic acid (8 g, 46.36 mmol). The reaction solution was stirred for 3 hours. The reaction solution was filtrated, and the filtrate was concentrated under reduced pressure to obtain the crude title product 48d (8.5 g), which was used directly in the next step without purification.

Step 4

5-(2-Methylpyridin-4-yl)-1,2,4-triazin-3-amine 48e

The crude compound 48d (8.5 g, 33.96 mmol) was dissolved in 80 mL of dioxane. The reaction solution was added with 20 mL of aqueous ammonia, and stirred for 1 hour. The reaction solution was concentrated under reduced pressure, and the residue was purified by CombiFlash rapid preparation instrument with elution system A to obtain the title product 48e (1.6 g), yield: 25.17%.

MS m/z (ESI): 188.1[M+1].

Step 5

6-Bromo-5-(2-methylpyridin-4-yl)-1,2,4-triazin-3-amine 48f

Compound 48e (1.6 g, 8.55 mmol) was added to 200 mL of acetonitrile. The reaction solution was then added with N-bromosuccinimide (3.80 g, 21.37 mmol) and trifluoroacetic acid (1.95 g, 17.09 mmol), and stirred for 64 hours. The reaction solution was concentrated under reduced pressure, and added with water. The aqueous phase was extracted with ethyl acetate (100 mL×3). The organic phases were combined, dried over anhydrous sodium sulfate, and filtrated. The filtrate was concentrated under reduced pressure, and the residue was purified by CombiFlash rapid preparation instrument with elution system A to obtain the title product 48f (1.87 g), yield: 82.22%.

Step 6

5-(2-Methylpyridin-4-yl)-6-(4-methylquinolin-6-yl)-1,2,4-triazin-3-amine 48

Compound 14b (100 mg, 375 μmol), compound 48f (101 mg, 375 μmol), [1,1'-bis(diphenylphosphino)ferrocene]dichloropalladium (55 mg, 75 μmol) and potassium carbonate (155 mg, 1.13 mmol) were dissolved in 12 mL of a mixed solution of 1,4-dioxane and water (V/V=5:1) under an argon atmosphere. The reaction solution was stirred at 80° C. for 2 hours. The reaction solution was cooled, and filtrated through celite. The filtrate was concentrated under reduced pressure, and the residue was purified by CombiFlash rapid preparation instrument with elution system A to obtain the title product 48 (30 mg), yield: 24.31%.

MS m/z (ESI): 329.5[M+1].

$^1$H NMR (400 MHz, DMSO-$d_6$) δ 8.75-8.77 (m, 1H), 8.37-8.38 (m, 1H), 8.07 (s, 1H), 7.93-7.95 (m, 1H), 7.70-7.72 (m, 1H), 7.65 (br, 2H), 7.38-7.40 (m, 2H), 7.06-7.07 (m, 1H), 2.50 (s, 3H), 2.42 (s, 3H).

Example 49

6-(4-Cyclopropylquinolin-6-yl)-5-(4-fluorophenyl)-1,2,4-triazin-3-amine 49

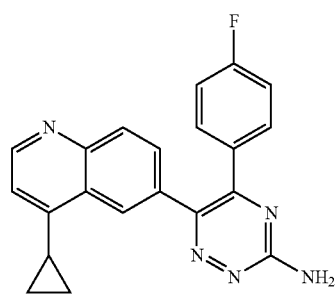

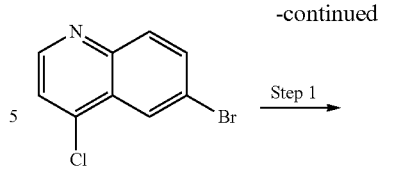

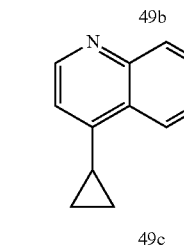

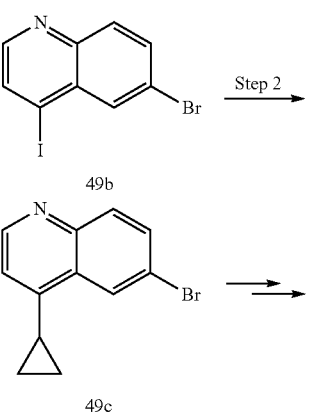

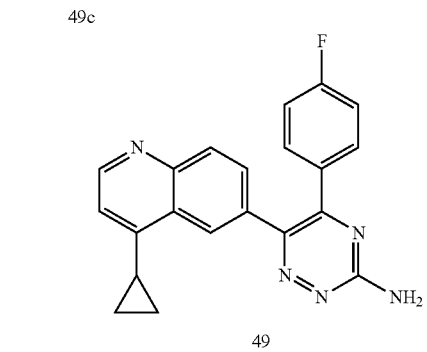

Step 1

6-Bromo-4-iodoquinoline 49b 5 mL of 4M hydrogen chloride in 1,4-dioxane were added to 6-bromo-4-chloroquinoline 49a (1 g, 4.12 mmol). The reaction solution was stirred for 10 minutes, and concentrated under reduced pressure for following use. The above concentrated residue was added with 60 mL of acetonitrile, followed by addition of sodium iodide (6.18 g, 41.24 mmol). The reaction solution was stirred under reflux for 16 hours. The reaction solution was cooled to room temperature, concentrated under reduced pressure, added with saturated sodium bicarbonate solution, and extracted with ethyl acetate (20 mL×3). The organic phases were combined, dried over anhydrous sodium sulfate, and concentrated under reduced pressure. The residue was purified by CombiFlash rapid preparation instrument with elution system B to obtain the title product 49b (850 mg), yield: 61.72%.

MS m/z (ESI): 333.9[M+1].

Step 2

6-Bromo-4-cyclopropylquinoline 49c

Compound 49b (350 mg, 1.05 mmol), cyclopropylboronic acid (99 mg, 1.15 mmol), [1,1'-bis(diphenylphosphino)ferrocene]dichloropalladium (153 mg, 209 μmop and potassium carbonate (433 mg, 3.14 mmol) were added to 30 mL of 1,4-dioxane under an argon atmosphere. The reaction solution was stirred at 80° C. for 16 hours. The reaction solution was cooled and filtrated. The filtrate was concentrated under reduced pressure, and the residue was purified by CombiFlash rapid preparation instrument with elution system B to obtain the title product 49c (110 mg), yield: 42.30%.

MS m/z (ESI): 250.1[M+1].

In accordance with the synthetic route of Example 22, the starting compound 22a in Step 2 was replaced with compound 49c, accordingly, the title product 49 (40 mg, yield: 27.53%) was prepared.

MS m/z (ESI): 358.5[M+1].

$^1$H NMR (400 MHz, DMSO-d$_6$) δ 8.74-8.75 (m, 1H), 8.34 (s, 1H), 7.96-7.98 (m, 1H), 7.78-7.80 (m, 1H), 7.48-7.52 (m, 4H), 7.18-7.22 (m, 2H), 7.14-7.15 (m, 1H), 2.27-2.28 (m, 1H), 0.97-0.99 (m, 2H), 0.71-0.73 (m, 2H).

Example 50

6-(8-Fluoro-4-methylquinazolin-6-yl)-5-(4-fluorophenyl)-1,2,4-triazin-3-amine 50

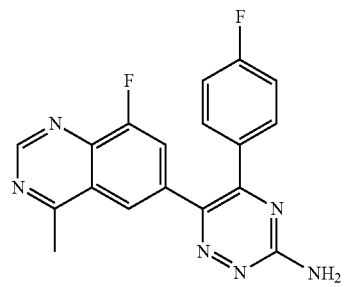

50

In accordance with the synthetic route of Example 22, the starting compound 22a in Step 2 was replaced with compound 45d, accordingly, the title product 50 (54 mg, yield: 41.48%) was prepared.

MS m/z (ESI): 351.0 [M+1].

$^1$H NMR (400 MHz, DMSO-d$_6$) δ 9.18 (s, 1H), 8.08 (s, 1H), 7.76-7.79 (m, 1H), 7.66 (br, 2H), 7.49-7.53 (m, 2H), 7.20-7.25 (m, 2H), 2.77 (s, 3H).

Example 51

6-(4-(Difluoromethyl)quinolin-6-yl)-5-(4-fluorophenyl)-1,2,4-triazin-3-amine 51

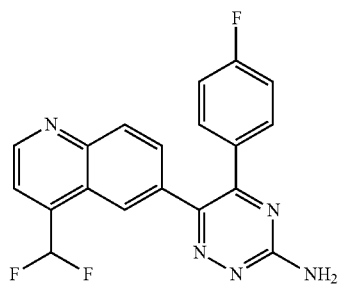

51

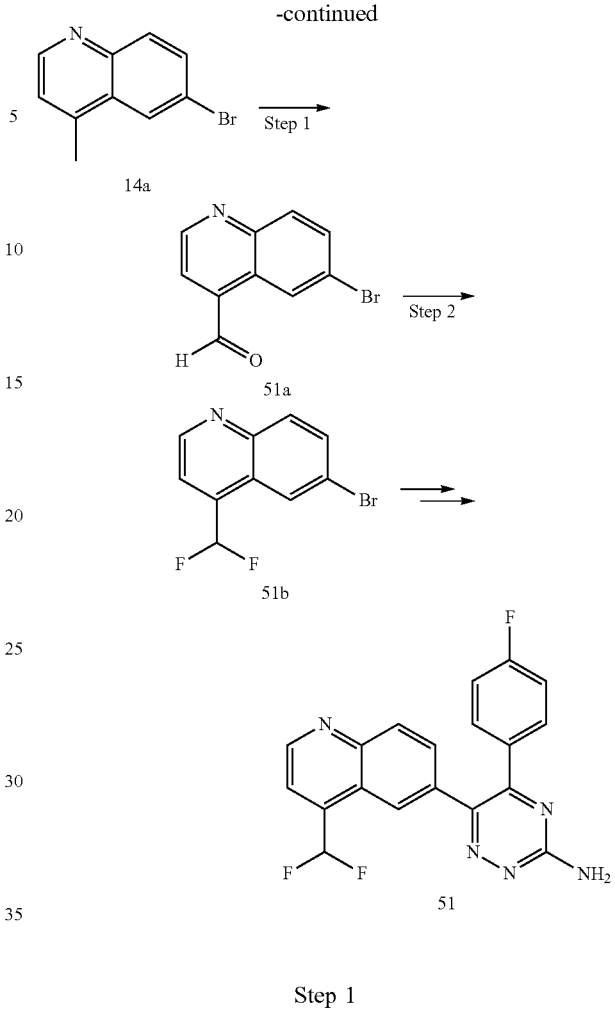

Step 1

6-Bromoquinoline-4-carbaldehyde 51a

Compound 14a (1.0 g, 4.50 mmol) was dissolved in 20 mL of 1,4-dioxane. The reaction solution was added with 2 mL of water, followed by addition of selenium dioxide (1.5 g, 13.51 mmol). The reaction solution was stirred at 80° C. for 16 hours, and then cooled to room temperature, added with saturated sodium bicarbonate solution, and extracted with ethyl acetate (30 mL×3). The organic phases were combined, washed with saturated sodium chloride solution, dried over sodium sulfate, and filtrated. The filtrate was concentrated under reduced pressure, and the residue was purified by silica gel column chromatography with elution system B to obtain the title compound 51a (670 mg), yield: 63.0%.

Step 2

6-Bromo-4-(difluoromethyl)quinoline 51b

Compound 51a (670 mg, 2.84 mmol) was dissolved in 20 mL of dichloromethane. The reaction solution was added dropwise with diethylaminosulfur trifluoride (915 mg, 5.68 mmol), and stirred for 16 hours. The reaction solution was added with saturated sodium bicarbonate solution, and stirred for 30 minutes. The reaction solution was extracted with dichloromethane (20 mL×3). The organic phases were combined, washed with saturated sodium chloride solution, dried over sodium sulfate, and filtrated. The filtrate was concentrated under reduced pressure, and the residue was purified by silica gel column chromatography with elution system B to obtain the title compound 51b (630 mg), yield: 86.0%.

In accordance with the similar synthetic route of Example 25, the starting compound 25a in Step 1 was replaced with compound 51b, and the starting compound 1c in Step 2 was replaced with compound 8a, accordingly, the title compound 51 (55 mg) was prepared.

MS m/z (ESI): 368.5 [M+1].

$^1$H NMR (400 MHz, DMSO-$d_6$) δ 9.05 (d, 1H), 8.21 (s, 1H), 8.08 (d, 1H), 7.80 (d, 1H), 7.75 (d, 1H), 7.53 (brs, 2H), 7.48 (t, 1H), 7.47 (q, 2H), 7.19 (t, 2H).

Example 52

5-(4-Fluorophenyl)-6-(4-(methyl-d3)quinazolin-6-yl)-1,2,4-triazin-3-amine 52

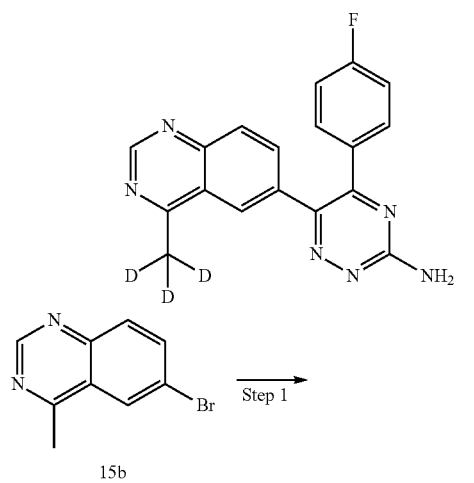

Step 1

6-Bromo-4-(methyl-d3)quinazoline 52a

Compound 15b (200 mg, 0.90 mmol) was suspended in 4 mL of deuteroxide. The reaction solution was added with benzoic acid (10.95 mg, 0.09 mmol), and stirred at 100° C. for 48 hours. The reaction solution was added with saturated sodium bicarbonate solution, and extracted with ethyl acetate (20 mL×3). The organic phases were combined, washed with saturated sodium chloride solution, dried over sodium sulfate, and filtrated. The filtrate was concentrated under reduced pressure, and the residue was purified by CombiFlash rapid preparation instrument with elution system B to obtain the title compound 52a (150 mg), yield: 74.0%.

In accordance with the similar synthetic route of Example 25, the starting compound 25a in Step 1 was replaced with compound 52a, and the starting compound 1c in Step 2 was replaced with compound 8a, accordingly, the title compound 52 (18 mg) was prepared.

MS m/z (ESI): 336.5 [M+1].

$^1$H NMR (400 MHz, DMSO-$d_6$) δ 9.11 (s, 1H), 8.28 (s, 1H), 7.85-8.28 (m, 2H), 7.59 (brs, 2H), 7.46-7.50 (m, 2H), 7.20 (t, 2H).

Example 53

6-(4-Ethylquinazolin-6-yl)-5-(4-fluorophenyl)-1,2,4-triazin-3-amine 53

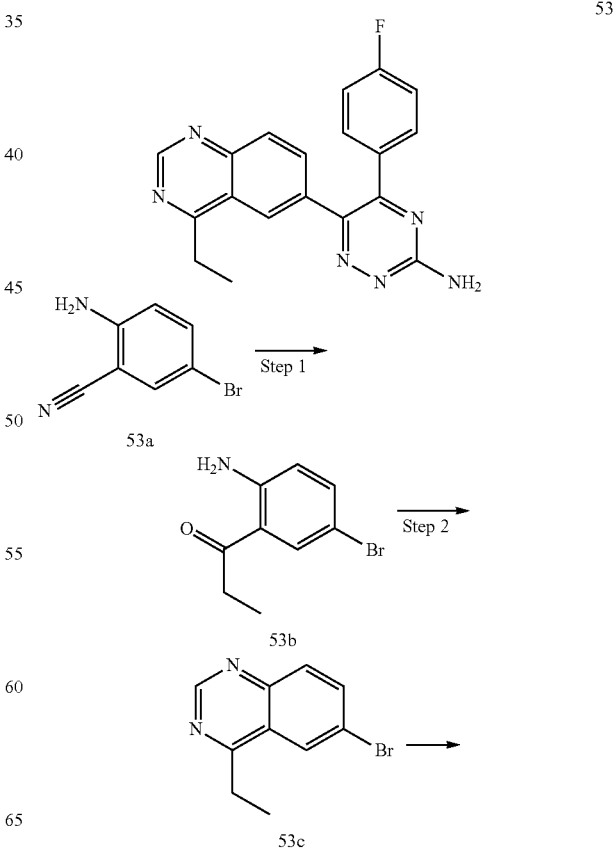

115

-continued

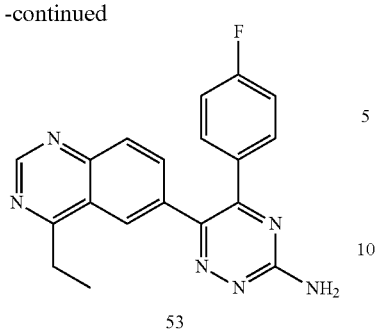

53

Step 1

1-(2-Amino-5-bromophenyl)propan-1-one 53b

2-Amino-5-bromobenzonitrile 53a (500 mg, 2.54 mmol, prepared according to the known method disclosed in "*European Journal of Medicinal Chemistry,* 2014, 76, 341-343") was dissolved in 10 mL of tetrahydrofuran. The reaction solution was cooled in an ice bath, added dropwise with 12.69 mL of 1.0 M ethyl magnesium bromide under an argon atmosphere, and stirred for 2 hours. The reaction solution was added with 6 M hydrochloric acid, and stirred for 2 hours. The reaction solution was added with saturated sodium carbonate solution, and extracted with ethyl acetate (50 mL×3). The organic phases were combined, washed with saturated sodium chloride solution, dried over sodium sulfate, and filtrated. The filtrate was concentrated under reduced pressure, and the residue was purified by Combi-Flash rapid preparation instrument with elution system B to obtain the title compound 53b (440 mg), yield: 76.02%.

Step 2

6-Bromo-4-ethylquinazoline 53c

Compound 53b (440 mg, 1.93 mmol), triethyl orthoformate (857.68 mg, 5.79 mmol) and ammonium acetate (451.14 mg, 5.79 mmol) were mixed, heated to 110° C. and stirred for 16 hours. The reaction solution was added with saturated sodium carbonate solution, and extracted with ethyl acetate (20 mL×3). The organic phases were combined, washed with saturated sodium chloride solution, dried over sodium sulfate, and filtrated. The filtrate was concentrated under reduced pressure, and the residue was purified by CombiFlash rapid preparation instrument with elution system B to obtain the title compound 53c (280 mg), yield: 61.22%.

In accordance with the similar synthetic route of Example 25, the starting compound 25a in Step 1 was replaced with compound 53c, and the starting compound 1c in Step 2 was replaced with compound 8a, accordingly, the title compound 53 (45 mg) was prepared.

MS m/z (ESI): 347.5 [M+1].

$^1$H NMR (400 MHz, DMSO-$d_6$) δ 9.15 (s, 1H), 8.21 (s, 1H), 7.94-8.01 (m, 2H), 7.57 (brs, 2H), 7.47-7.50 (m, 2H), 7.20 (t, 2H), 3.10 (q, 2H), 1.16 (t, 3H).

116

Example 54

5-(4-Fluorophenyl)-6-[4-(trifluoromethyl)quinolin-6-yl]-1,2,4-triazin-3-amine 54

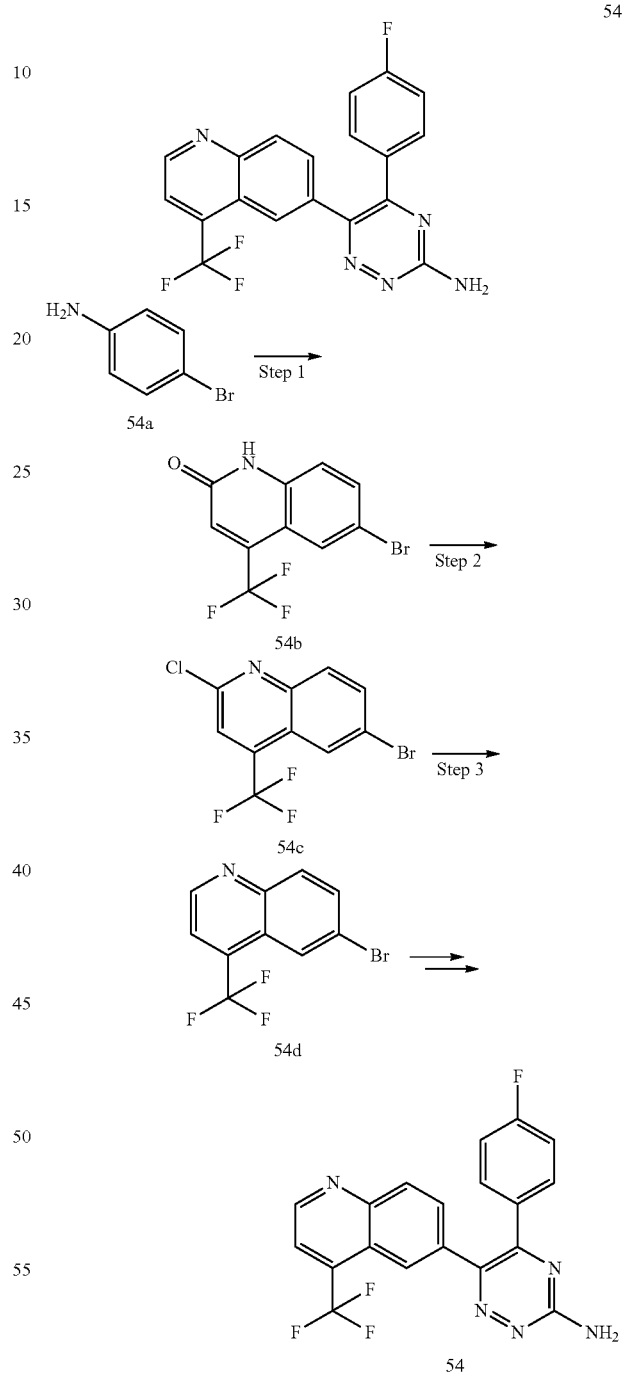

Step 1

6-Bromo-4-trifluoromethylquinolin-2(1H)-one 54b

Ethyl trifluoroacetoacetate (1.24 g, 6.75 mmol) and triethylamine (1.65 g, 16.28 mmol) were added to 20 mL of toluene. The reaction solution was then added dropwise with 3 mL of 2.7 M 4-bromoaniline 54a in toluene, and stirred under reflux for 16 hours. The reaction solution was concentrated under reduced pressure. The residue was added with 30 mL of dichloromethane, washed with water (20 mL×2) and saturated sodium chloride solution (20 mL), dried over anhydrous sodium sulfate, and filtered. The filtrate was concentrated under reduced pressure. The resulting intermediate was added with 6 mL of sulfuric acid, and stirred at 100° C. for 4 hours. The reaction solution was cooled to room temperature, added dropwise with saturated sodium bicarbonate solution to adjust the pH to greater than 10, and extracted with ethyl acetate (30 mL×3). The organic phases were combined, dried over anhydrous sodium sulfate, and filtrated. The filtrate was concentrated under reduced pressure, and the residue was purified by CombiFlash rapid preparation instrument with elution system B to obtain the title product 54b (1.5 g), yield: 63.70%.

MS m/z (ESI): 291.9[M+1].

Step 2

6-Bromo-2-chloro-4-(trifluoromethyl)quinoline 54c

Compound 54b (1.5 g, 5.14 mmol) was added with phosphorus oxychloride (4.73 g, 30.82 mmol), and stirred at 100° C. for 5 hours. The reaction solution was cooled, added to ice water, stirred for 30 minutes, and extracted with ethyl acetate (50×3). The organic phases were combined, dried over anhydrous sodium sulfate, and concentrated under reduced pressure. The residue was purified by CombiFlash rapid preparation instrument with elution system B to obtain the title product 54c (1.3 g), yield: 81.52%.

Step 3

6-Bromo-4-trifluoromethylquinoline 54d

Compound 54c (500 mg, 1.61 mmol) was dissolved in 8 mL of trifluoroacetic acid. The reaction solution was then added with zinc powder (842 mg, 12.88 mmol), and stirred for 16 hours. The reaction solution was filtrated and concentrated under reduced pressure. The residue was added dropwise with 1 M sodium hydroxide until the pH was greater than 10, and extracted with ethyl acetate (30 mL×3). The organic phases were combined, dried over anhydrous sodium sulfate, and concentrated under reduced pressure. The residue was purified by CombiFlash rapid preparation instrument with elution system B to obtain the title product 54d (200 mg), yield: 44.99%.

MS m/z (ESI): 275.8 [M+1].

In accordance with the synthetic route of Example 22, the starting compound 22a in Step 2 was replaced with compound 54d, accordingly, the title product 54 (30 mg) was prepared.

MS m/z (ESI): 386.4[M+1].

$^1$H NMR (400 MHz, DMSO-$d_6$) δ 9.11-9.12 (m, 1H), 8.19-8.21 (m, 1H), 7.99-8.03 (m, 2H), 7.93-7.94 (m, 1H), 7.62 (br, 2H), 7.47-7.50 (m, 2H), 7.18-7.23 (m, 2H).

Example 55

5-(4-Fluorophenyl)-6-(4-methoxyquinazolin-6-yl)-1,2,4-triazin-3-amine 55

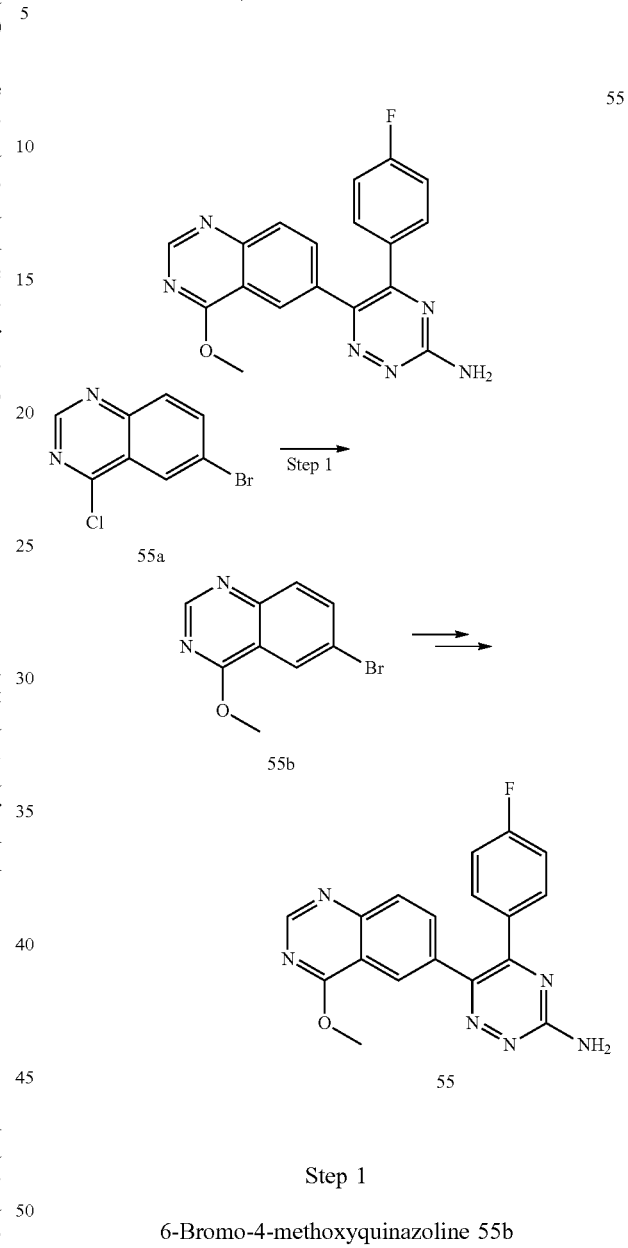

Step 1

6-Bromo-4-methoxyquinazoline 55b

6-Bromo-4-chloroquinazoline 55a (1.0 g, 4.10 mmol) was dissolved in 80 mL of methanol. The reaction solution was added with sodium methoxide (2.21 g, 41.05 mmol), and stirred for 3 hours. The reaction solution was concentrated to dryness, added with water, and filtrated. The filter cake was dried to obtain the product 55b (0.55 g), yield: 56.01%.

MS m/z (ESI): 239.1[M+1].

In accordance with the synthetic route of Example 22, the starting compound 22a in Step 2 was replaced with compound 55b, accordingly, the title product 55 (40 mg) was prepared. Yield: 31.29%.

MS m/z (ESI): 349.2 [M+1].

$^1$H NMR (400 MHz, DMSO-$d_6$) δ 8.82 (s, 1H), 8.28 (s, 1H), 7.81-7.83 (m, 1H), 7.72-7.74 (m, 1H), 7.56 (br, 2H), 7.47-7.50 (m, 2H), 7.18-7.22 (m, 2H), 4.12 (s, 3H).

TEST EXAMPLES

Biological Assay

Test Example 1

Determination of the inhibition activity of the compounds of the present invention on the adenosine $A_{2a}$ receptor ($A_{2a}R$) cAMP signaling pathway, the adenosine $A_{2b}$ receptor ($A_{2b}R$) cAMP signaling pathway, the adenosine $A_1$ receptor ($A_1R$) cAMP signaling pathway and the adenosine $A_3$ receptor ($A_3R$) cAMP signaling pathway.

The inhibition activity of the compounds of the present invention on the adenosine $A_{2a}$ receptor ($A_{2a}R$) cAMP signaling pathway, the adenosine $A_{2b}$ receptor cAMP signaling pathway, the adenosine $A_1$ receptor cAMP signaling pathway and the adenosine $A_3$ receptor cAMP signaling pathway was determined by the following method. The experimental method is briefly described as follows:

I. Experimental Materials and Instruments
1. CHO-K1/$A_{2a}R$ cells (NM_000675.5) or CHO-K1/$A_{2b}R$ cells (NM_000676.2) or CHO-K1/$A_1R$ cells (NM_000674.2) or CHO-K1/$A_3R$ cells (NM_000677.3)
2. Fetal bovine serum (Gibco, 10099-141)
3. Bleomycin (Thermo, R25001) or G418 (ENZO, ALX-380-013-G005) or puromycin (Thermo, 10687-010)
4. DMEM/F12 medium (GE, SH30023.01)
5. Cell separation buffer (Thermo Fisher, 13151014)
6. HEPES (Gibco, 42360-099)
7. Bovine serum albumin (MP Biomedicals, 219989725)
8. Rolipram (sigma, R6520-10MG)
9. Adenosine deaminase (sigma, 10102105001)
10. Forskolin (sigma, F6886)
11. 2Cl-IB-MECA (Tocrics, 1104/10)
12. N6-cyclopentyladenosine (Tocris, 1702/50)
13. Balanced salt buffer (Thermo, 14025-092)
14. cAMP dynamic 2 kit (Cisbio, 62AM4PEB)
15. 384-well plate (Corning, 4514) or (Nunc, 267462#)
16. Ethyl carbazole (Torcis, 1691/10)
17. PHERAstar multi-function microplate reader (Cisbio, 62AM4PEB)

II. Experimental Procedures 2.1 Adenosine $A_{2a}$ receptor

CHO-K1/$A_{2a}R$ cells were cultured in DMEM/F12 medium containing 10% fetal bovine serum and 800 μg/ml bleomycin. The cells were digested with the cell separation buffer during the experiment. The cells were resuspended in the balanced salt buffer containing 20 mM HEPES and 0.1% bovine serum albumin and counted, and the cell density was adjusted to $10^6$ cells/ml. In the 384-well plate, each well was added with 5 μl of cell suspension, and 2.5 μl of test compound (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. Each well was then added with 2.5 μl of ethyl carbazole (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. The final concentrations of the compounds were: 10000, 2000, 400, 80, 16, 3.2, 0.64, 0.128, 0.0256, 0.00512, and 0.001024 nM. The final concentration of ethyl carbazole was 20 nM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 5 μl of diluted cAMP-d2, followed by addition of 5 μl of diluted Anti-cAMP-Eu-Cryptate, and the plate was incubated at room temperature in the dark for 1 hour. The HTRF signal values were read by the PHERAstar multi-function microplate reader. $IC_{50}$ values of inhibition activity of the compounds were calculated by Graphpad Prism software, and are shown in Table 1.

2.2 Adenosine $A_{2b}$ Receptor

CHO-K1/$A_{2b}R$ cells were cultured in DMEM/F12 medium containing 10% fetal bovine serum and 1 mg/ml G418. The cells were digested with the cell separation buffer during the experiment. The cells were resuspended in the balanced salt buffer containing 20 mM HEPES and 0.1% bovine serum albumin and counted, and the cell density was adjusted to $10^6$ cells/ml. In the 384-well plate, each well was added with 5 μl of cell suspension, and 2.5 μl of test compound (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. Each well was then added with 2.5 μl of ethyl carbazole (4× concentration) (Torcis, 1691/10) formulated with the balanced salt buffer containing 20 mM HEPES, 0.1% bovine serum albumin, 54 μM rolipram and 2.7 U/ml adenosine deaminase, and the plate was incubated at room temperature for 30 minutes. The final concentrations of the compounds were: 100000, 10000, 1000, 100, 10, 1, 0.1 and 0 nM. The final concentration of ethyl carbazole was 1 μM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 5 μl of diluted cAMP-d2, followed by addition of 5 μl of diluted Anti-cAMP-Eu-Cryptate, and the plate was incubated at room temperature in the dark for 1 hour. The HTRF signal values were read by the PHERAstar multi-function microplate reader. $IC_{50}$ values of inhibition activity of the compounds were calculated by Graphpad Prism software, and are shown in Table 2.

2.3 Adenosine $A_1$ Receptor

CHO-K1/$A_1R$ cells were cultured in DMEM/F12 medium containing 10% fetal bovine serum and 1 mg/ml G418. The cells were digested with the cell separation buffer during the experiment. The cells were then resuspended in the balanced salt buffer containing 20 mM HEPES and 0.1% bovine serum albumin and counted, and the cell density was adjusted to $5\times10^5$ cells/ml. In the 384-well plate, each well was added with 12.5 μl of cell suspension, and 6.25 μl of test compound (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. Each well was then added with 6.25 μl of forskolin and N6-cyclopentyladenosine (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. The final concentrations of the compounds were: 100000, 10000, 1000, 100, 10, 1, 0.1 and 0 nM. The final concentrations of forskolin was 10 μM. The final concentrations of CPA was 10 nM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 12.5 μl of diluted cAMP-d2, followed by addition of 12.5 μl of diluted Anti-cAMP-Eu-Cryptate, and the plate was incubated at room temperature in the dark for 1 hour. The HTRF signal values were read by the PHERAstar multi-function microplate reader. $IC_{50}$ values of inhibition activity of the compounds were calculated by Graphpad Prism software, and are shown in Table 3.

2.4 Adenosine $A_3$ Receptor

CHO-K1/$A_3$R cells were cultured in DMEM/F12 medium containing 10% fetal bovine serum and 10 μg/ml puromycin. The cells were digested with the cell separation buffer during the experiment. The cells were resuspended in the balanced salt buffer containing 20 mM HEPES and 0.1% bovine serum albumin and counted, and the cell density was adjusted to $5 \times 10^5$ cells/ml. In the 384-well plate, each well was added with 12.5 μl of cell suspension, and 6.25 μl of test compound (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. Each well was then added with 6.25 μl of forskolin and 2Cl-IB-MECA (4× concentration) formulated with the balanced salt buffer containing 20 mM HEPES, 0.1% bovine serum albumin, 54 μM rolipram and 2.7 U/ml adenosine deaminase, and the plate was incubated at room temperature for 30 minutes. The final concentrations of the compounds were: 100000, 10000, 1000, 100, 10, 1, 0.1 and 0 nM. The final concentrations of forskolin was 10 μM. The final concentration of 2Cl-IB-MECA was 5 nM. Intracellular cAMP concentration was detected with the cAMP dynamic 2 kit. cAMP-d2 and Anti-cAMP-Eu-Cryptate were diluted respectively with the cAMP lysis buffer at a ratio of 1:4. Each well was added with 12.5 μl of diluted cAMP-d2, followed by addition of 12.5 μl of diluted Anti-cAMP-Eu-Cryptate, and the plate was incubated at room temperature in the dark for 1 hour. The HTRF signal values were read by the PHERAstar multi-function microplate reader. $IC_{50}$ values of inhibition activity of the compounds were calculated by Graphpad Prism software, and are shown in Table 3.

TABLE 1

$IC_{50}$ values of the inhibition activity of the compounds of the present invention on the adenosine $A_{2a}$ receptor ($A_{2a}$R) cAMP signaling pathway.

| Example No. | $IC_{50}$/nM ($A_{2a}$R) |
|---|---|
| 1 | 0.5 |
| 2 | 0.6 |
| 3 | 0.7 |
| 4 | 0.7 |
| 5 | 0.4 |
| 6 | 1.3 |
| 7 | 3.1 |
| 8 | 3.6 |
| 14 | 0.1 |
| 15 | 0.1 |
| 16 | 0.2 |
| 17 | 0.5 |
| 18 | 0.2 |
| 19 | 0.4 |
| 20 | 1.5 |
| 22 | 0.3 |
| 23 | 0.4 |
| 24 | 0.9 |
| 25 | 1.5 |
| 26 | 1.8 |
| 27 | 2.2 |
| 28 | 3.0 |
| 29 | 3.5 |
| 30 | 3.7 |
| 31 | 3.8 |
| 44 | 0.8 |
| 45 | 1.2 |
| 46 | 1.6 |

TABLE 1-continued $IC_{50}$ values of the inhibition activity of the compounds of the present invention on the adenosine $A_{2a}$ receptor ($A_{2a}$R) cAMP signaling pathway.

| Example No. | $IC_{50}$/nM ($A_{2a}$R) |
|---|---|
| 47 | 1.6 |
| 48 | 2.4 |
| 49 | 2.5 |
| 50 | 3.2 |
| 51 | 3.5 |
| 52 | 0.9 |
| 13 (Example 1 (lxxii) of WO2011095625) | 158.3 |

Conclusion: The compounds of the present invention have a significant inhibition activity on the adenosine $A_{2a}$ receptor. Compared with Comparative Example 1, the introduction of a nitrogen atom into the fused aryl moiety of the core structrue results in an unexpected inhibition activity of the compounds of the present invention on the adenosine $A_{2a}$ receptor. The structural difference between the compound of Comparative Example 1 and the compound of Example 3 is merely that the compound of Example 3 has the introduction of a nitrogen atom into the 5-position of the naphthyl of the compound of Comparative Example 1, but the inhibition activity on the adenosine $A_{2a}$ receptor differs by 225 times.

TABLE 2

$IC_{50}$ values of the inhibition activity of the compounds of the present invention on the adenosine $A_{2b}$ receptor ($A_{2b}$R) cAMP signaling pathway.

| Example No. | $IC_{50}$/nM ($A_{2b}$R) |
|---|---|
| 3 | 47 |
| 4 | 4 |
| 5 | 46 |
| 14 | 3 |
| 15 | 7 |
| 16 | 18 |
| 17 | 22 |
| 19 | 25 |
| 22 | 7 |
| 23 | 17 |
| 25 | 4 |
| 45 | 25 |
| 46 | 18 |
| 52 | 14 |

Conclusion: The compounds of the present invention have a good inhibition activity on the adenosine $A_{2b}$ receptor.

TABLE 3

$IC_{50}$ values of the inhibition activity of the compounds of the present invention on the adenosine $A_1$ receptor ($A_1$R) cAMP signaling pathway and the adenosine $A_3$ receptor cAMP signaling pathway.

| Example No. | $IC_{50}$/nM ($A_{2a}$R) | $IC_{50}$/nM ($A_1$R) | $IC_{50}$ ratio ($A_1$R/$A_{2a}$R) | $IC_{50}$/nM ($A_3$R) | $IC_{50}$ ratio ($A_3$R/$A_{2a}$R) |
|---|---|---|---|---|---|
| 1 | 0.5 | 121 | 242 | $>10^4$ | $>10^4$ |
| 2 | 0.6 | 133 | 221 | $>10^4$ | $>10^4$ |
| 3 | 0.7 | 97 | 139 | $>10^4$ | $>10^4$ |
| 15 | 0.1 | 248 | 2484 | $>10^4$ | $>10^4$ |
| 16 | 0.2 | 161 | 803 | $>10^4$ | $>10^4$ |
| 17 | 0.5 | 1349 | 2698 | $>10^4$ | $>10^4$ |
| 18 | 0.2 | 190 | 948 | $>10^4$ | $>10^4$ |
| 19 | 0.4 | 1423 | 3557 | $>10^4$ | $>10^4$ |
| 20 | 1.5 | 617 | 411 | $>10^4$ | $>10^3$ |
| 22 | 0.3 | 100 | 334 | $>10^4$ | $>10^4$ |
| 31 | 3.8 | 1639 | 431 | $>10^4$ | $>10^3$ |

TABLE 3-continued

IC$_{50}$ values of the inhibition activity of the compounds of the present invention on the adenosine A$_1$ receptor (A$_1$R) cAMP signaling pathway and the adenosine A$_3$ receptor cAMP signaling pathway.

| Example No. | IC$_{50}$/nM (A$_{2a}$R) | IC$_{50}$/nM (A$_1$R) | IC$_{50}$ ratio (A$_1$R/A$_{2a}$R) | IC$_{50}$/nM (A$_3$R) | IC$_{50}$ ratio (A$_3$R/A$_{2a}$R) |
|---|---|---|---|---|---|
| 44 | 0.8 | 646 | 807 | >10$^4$ | >10$^4$ |
| 45 | 1.2 | 930 | 775 | >10$^4$ | >10$^3$ |
| 48 | 2.4 | 3276 | 1365 | >10$^4$ | >10$^3$ |
| 50 | 3.2 | 3257 | 1018 | >10$^4$ | >10$^3$ |
| 52 | 0.9 | 876 | 973 | >10$^4$ | >10$^4$ |

Conclusion: The compounds of the present invention have a weak inhibition activity on the adenosine A$_1$ receptor and the adenosine A$_3$ receptor, indicating that the compounds of the present invention are selective for the adenosine A$_{2a}$ receptor and the adenosine A$_{2b}$ receptor, particularly for the adenosine A$_{2a}$ receptor.

Pharmacokinetics Evaluation

Test Example 2. Pharmacokinetics Assay of the Compounds of the Present Invention in Mice 1. Abstract Mice were used as test animals. The drug concentration in plasma at different time points was determined by LC/MS/MS method after intragastrical administration of the compounds of Examples 2, 3, 17, 18, 19, 20, 31 and 44 to mice. The pharmacokinetic behavior of the compounds of the present invention was studied and evaluated in mice.

2. Test Protocol 2.1 Test Compounds

Compounds of Examples 2, 3, 17, 18, 19, 20, 31 and 44.

2.2 Test Animals

Seventy-two C57 mice (female) were purchased from Shanghai Jiesijie Laboratory Animal Co., LTD, with Certificate No.: SCXK (Shanghai) 2013-0006, and equally divided into 8 groups (9 mice per group).

2.3 Preparation of the Test Compounds

A certain amount of the test compound was weighed, and added with 5% by volume of DMSO, 5% by volume of tween 80 and 90% by volume of normal saline to prepare a 0.1 mg/mL colorless, clear and transparent solution.

2.4 Administration

After an overnight fast, C57 mice were administered intragastrically the test compounds at an administration dosage of 2.0 mg/kg and an administration volume of 0.2 mL/10 g.

3. Process

The mice were intragastrically administered the compounds of Examples 2, 3, 17, 18, 19, 20, 31 and 44. 0.1 ml of blood was taken before administration and at 0.5, 1.0, 2.0, 4.0, 6.0, 8.0, 11.0 and 24.0 hours after administration. The samples were stored in heparinized tubes, and centrifuged for 10 minutes at 3,500 rpm to separate the blood plasma. The plasma samples were stored at −20° C.

The content of the test compounds in the plasma of mice after intragastrical administration of the test compounds at different concentrations was determined: 25 μL of mouse plasma at each time after administration were taken, added with 50 μL of the internal standard solution of camptothecin (100 ng/mL) and 200 μL of acetonitrile, vortex-mixed for 5 minutes, and centrifuged for 10 minutes (4000 rpm). 5 μL of the supernatant were taken from the plasma samples for LC/MS/MS analysis.

4. Results of Pharmacokinetic Parameters

Pharmacokinetic parameters of the compounds of the present invention are shown below:

| | Pharmacokinetics assay in mice (2 mg/kg) | | | | | |
|---|---|---|---|---|---|---|
| No. | Plasma concentration Cmax (ng/mL) | Area under curve AUC (ng/mL*h) | Half-life T½ (h) | Residence time MRT (h) | Clearance CLz/F (ml/min/kg) | Apparent distribution volume Vz/F (ml/kg) |
| Example 2 | 441 | 412 | 2.17 | 1.79 | 78.3 | 14736 |
| Example 3 | 395 | 419 | 2.3 | 1.61 | 78.6 | 15676 |
| Example 17 | 265 | 204 | 1.09 | 1.17 | 162 | 15329 |
| Example 18 | 402 | 495 | 1.59 | 1.43 | 65 | 9012 |
| Example 19 | 1960 | 5030 | 2.74 | 3.13 | 6.61 | 1567 |
| Example 20 | 866 | 1173 | 1.24 | 1.41 | 28 | 3047 |
| Example 31 | 302 | 339 | 2.02 | 2.02 | 95 | 16716 |
| Example 44 | 720 | 501 | 0.85 | 0.85 | 65 | 4794 |

Conclusion: The compounds of the present invention are well absorbed, and have a pharmacokinetic advantage.

What is claimed is:

1. A compound of formula (I):

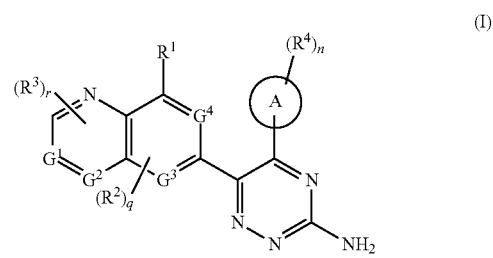

or a tautomer, mesomer, racemate, enantiomer, or diastereomer thereof, or a mixture thereof, or a pharmaceutically acceptable salt thereof, wherein:

ring A is aryl or heteroaryl;

$G^1$, $G^2$, $G^3$ and $G^4$ are identical or different and are each independently selected from the group consisting of C, CH and N;

$R^1$ is selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —OR$^5$, —C(O)R$^5$, —S(O)$_m$R$^5$, NH$_2$S(O)$_m$R$^5$, —NR$^6$R$^7$, S(O)$_m$NR$^6$R$^7$ and —C(O)NR$^6$R$^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

each $R^2$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

each $R^3$ is identical or different and each is independently selected from the group consisting of hydrogen, halogen, alkyl, alkoxy, haloalkyl, deuterated alkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, deuterium, alkyl, alkoxy, haloalkyl, hydroxy, hydroxyalkyl, cyano, amino, nitro, cycloalkyl, heterocyclyl, aryl and heteroaryl;

each $R^4$ is identical or different and each is independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —$OR^5$, —$C(O)R^5$, —$S(O)_mR^5$, $NH_2S(O)_mR^5$, —$NR^6R^7$, $S(O)_mNR^6R^7$ and —$C(O)NR^6R^7$, wherein the alkyl, alkoxy, haloalkyl, hydroxyalkyl, cycloalkyl, heterocyclyl, aryl and heteroaryl are each independently optionally substituted by one or more substituents selected from the group consisting of halogen, alkyl, alkoxy, haloalkyl, hydroxy, hydroxyalkyl, cyano, amino, nitro, cycloalkyl, heterocyclyl, aryl and heteroaryl;

$R^5$ is selected from the group consisting of hydrogen, alkyl, haloalkyl, amino, hydroxy, cycloalkyl, heterocyclyl, aryl and heteroaryl;

$R^6$ and $R^7$ are each independently selected from the group consisting of hydrogen, alkyl, haloalkyl, cycloalkyl, heterocyclyl, aryl and heteroaryl, wherein the alkyl, cycloalkyl, heterocyclyl, aryl and heteroaryl are each independently optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, $R^6$ and $R^7$ together with the nitrogen atom to which they are attached form a heterocyclyl, wherein the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

m is 0, 1 or 2;
r is 0, 1, 2 or 3;
q is 0, 1 or 2; and
n is 0, 1, 2, 3, 4 or 5.

2. The compound according to claim 1, being a compound of formula (Iaa):

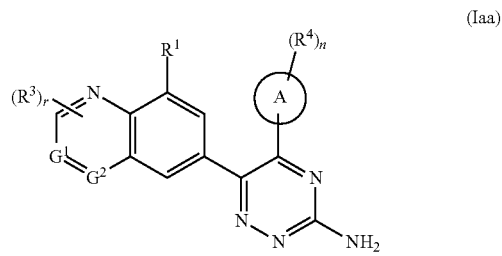

(Iaa)

or a tautomer, mesomer, racemate, enantiomer, or diastereomer thereof, or a mixture thereof, or a pharmaceutically acceptable salt thereof,
wherein
ring A, $G^1$, $G^2$, $R^1$, $R^3$, $R^4$, r and n are as defined in claim 1.

3. The compound according to claim 1, being a compound of formula (II):

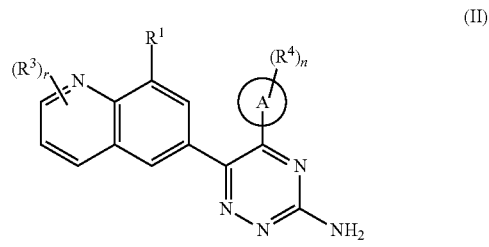

(II)

or a tautomer, mesomer, racemate, enantiomer, or diastereomer thereof, or a mixture thereof, or a pharmaceutically acceptable salt thereof,
wherein ring A, $R^1$, $R^3$, $R^4$, r and n are as defined in claim 1.

4. The compound according to claim 1, wherein ring A is selected from the group consisting of phenyl, pyridyl, thienyl and furanyl.

5. The compound according to claim 1, being a compound of formula (III):

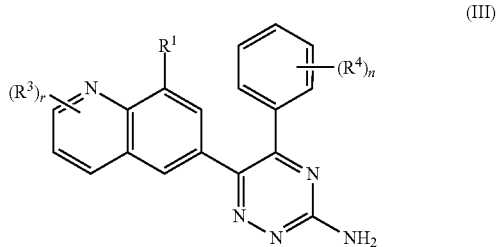

(III)

or a tautomer, mesomer, racemate, enantiomer, or diastereomer thereof, or a mixture thereof, or a pharmaceutically acceptable salt thereof,
wherein $R^1$, $R^3$, $R^4$, r and n are as defined in claim 1.

6. The compound according to claim 1, wherein $R^1$ is selected from the group consisting of hydrogen, halogen, alkyl, alkoxy, cyano, cycloalkyl, haloalkyl, heterocyclyl and —C(O)NR$^6$R$^7$; and R$^6$ and R$^7$ are as defined in claim 1.

7. The compound according to claim 1, wherein each $R^3$ is identical or different and each is independently selected from the group consisting of hydrogen, halogen, alkyl, haloalkyl, deuterated alkyl, alkoxy, cyano, cycloalkyl and heterocyclyl, wherein the alkyl and alkoxy are each independently optionally substituted by one or more substituents selected from the group consisting of halogen, deuterium, hydroxy, cyano, amino, nitro, cycloalkyl and heterocyclyl.

8. The compound according to claim 1, wherein each $R^4$ is identical or different and each is independently selected from the group consisting of hydrogen, alkyl and halogen.

9. A compound selected from the group consisting of:

1
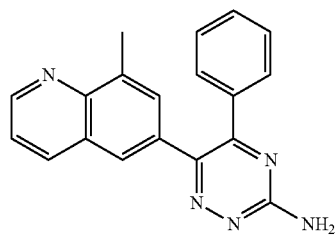

2
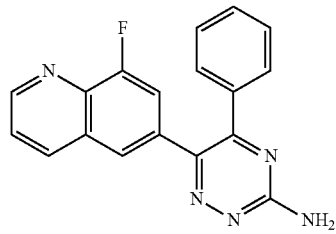

3
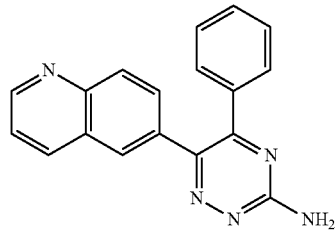

4
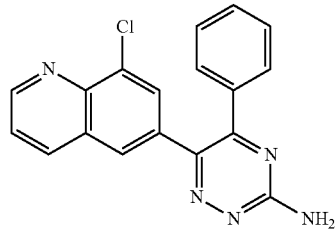

5
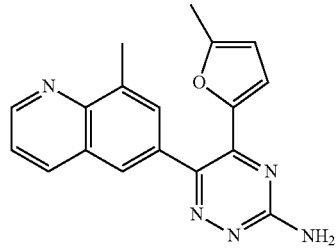

6
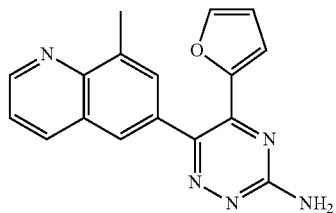

7
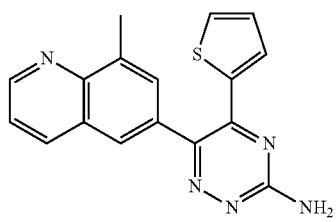

8
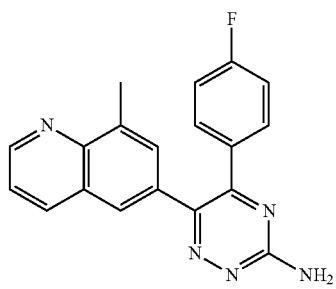

9
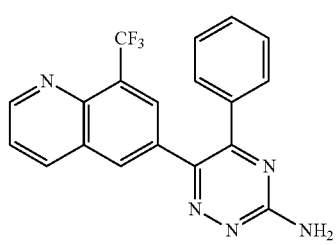

10
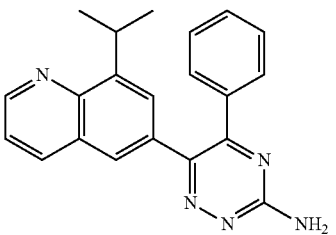

11
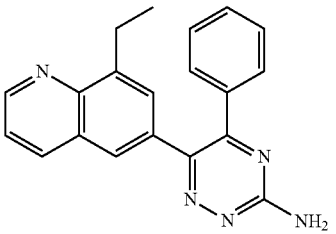

129
-continued
12
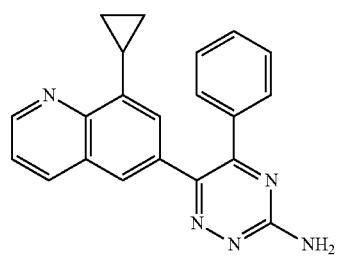
14
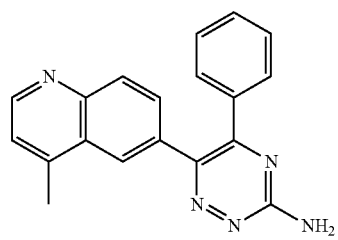
15
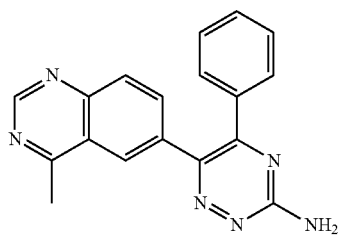
16
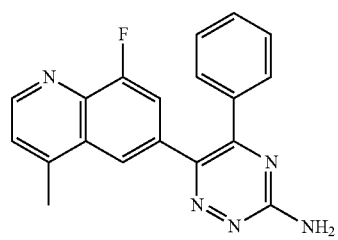
17
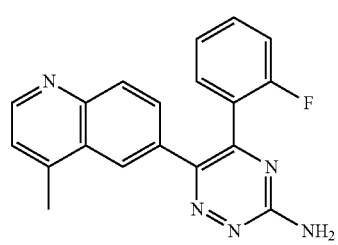
18
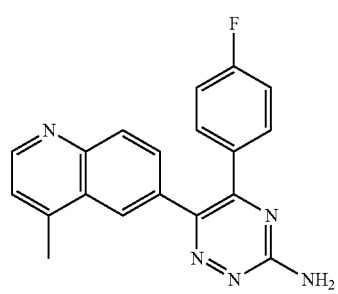
130
-continued
19
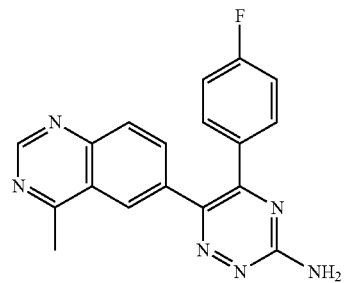
20
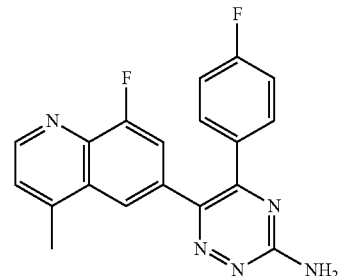
21
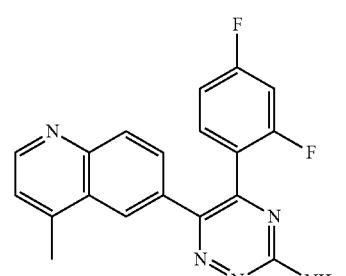
22
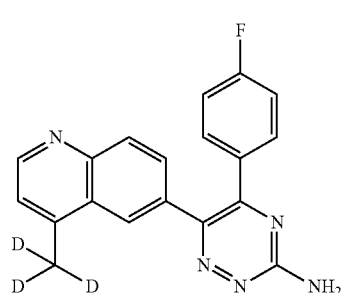
23
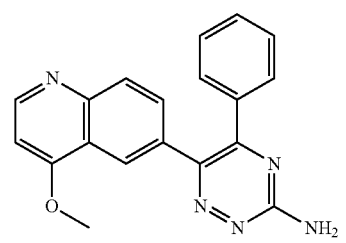
24
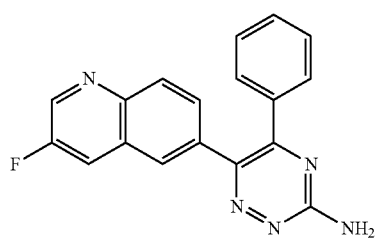

25
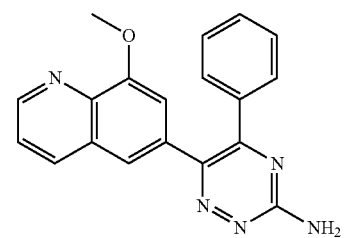
26
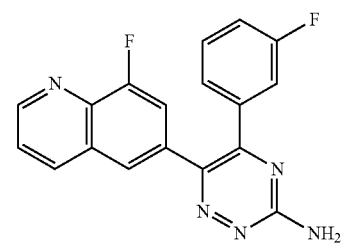
27
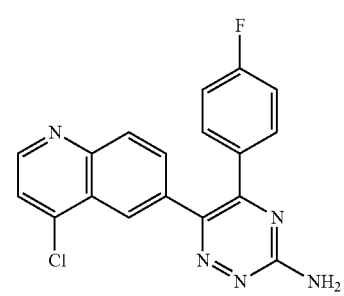
28
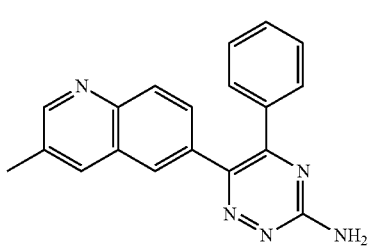
29
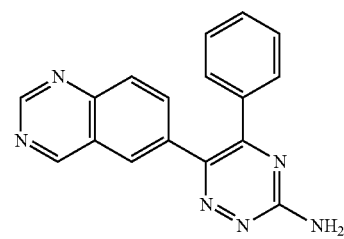
30
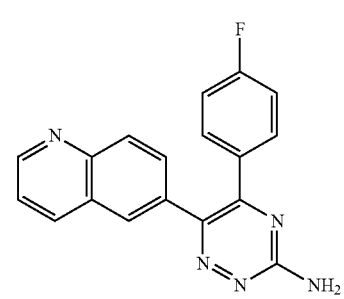
31
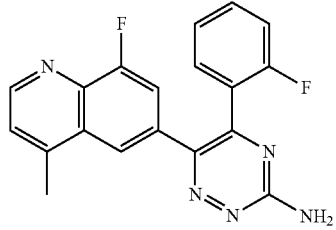
32
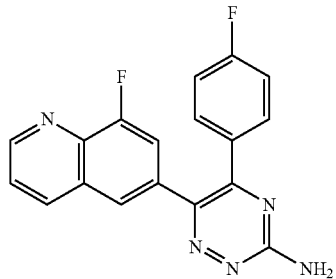
33
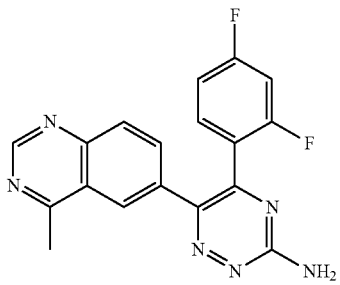
34
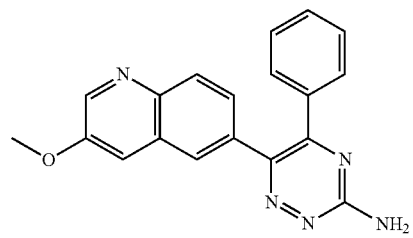
35
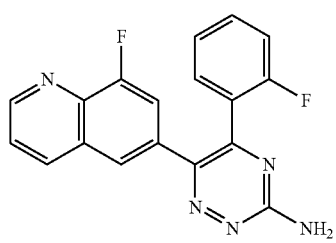
36
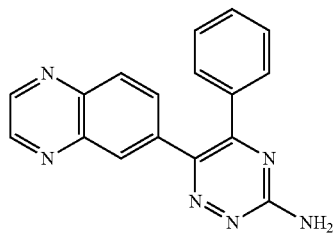

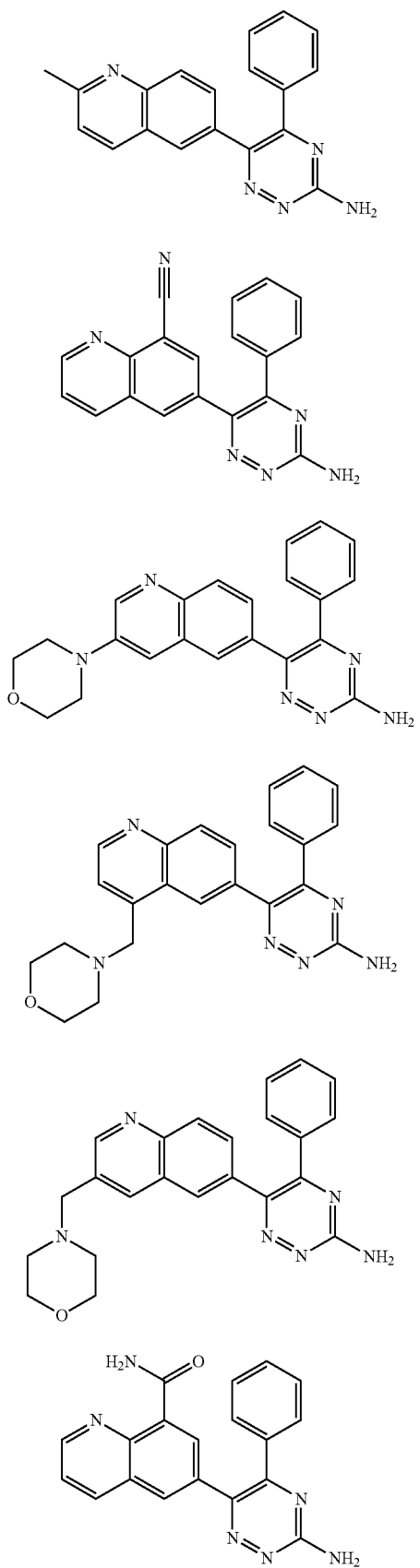
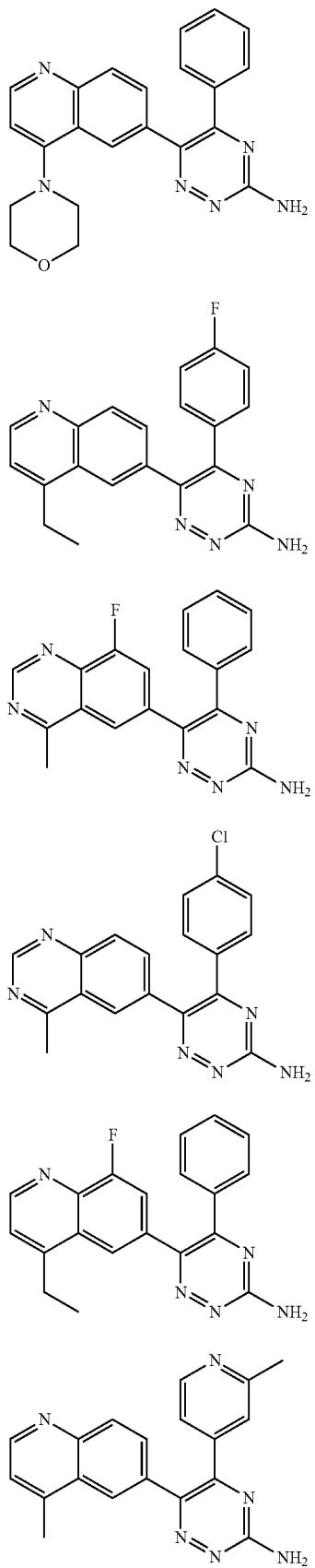

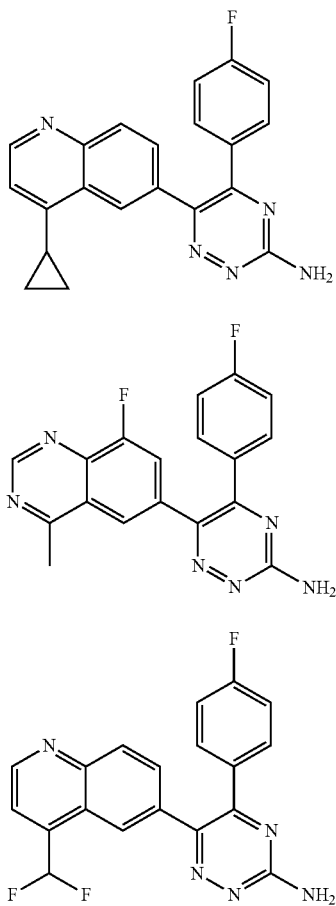
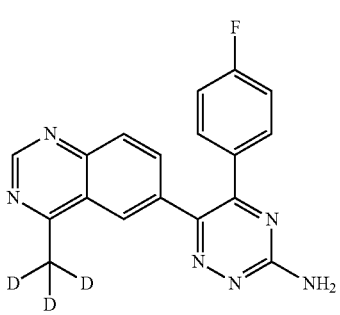
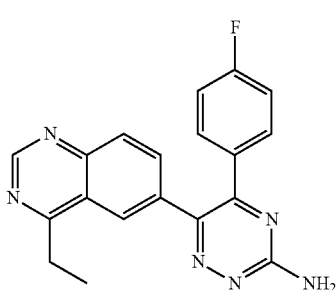
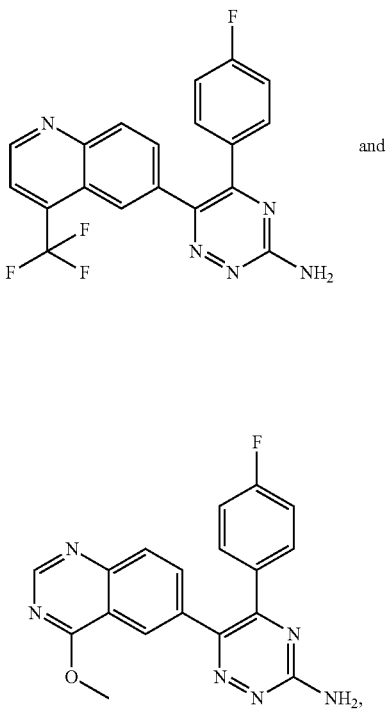
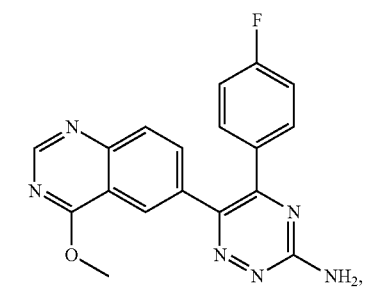
or a tautomer, mesomer, racemate, enantiomer, or diastereomer thereof, or a mixture thereof, or a pharmaceutically acceptable salt thereof.
10. A method for preparing the compound of formula (I) according to claim 1, comprising:
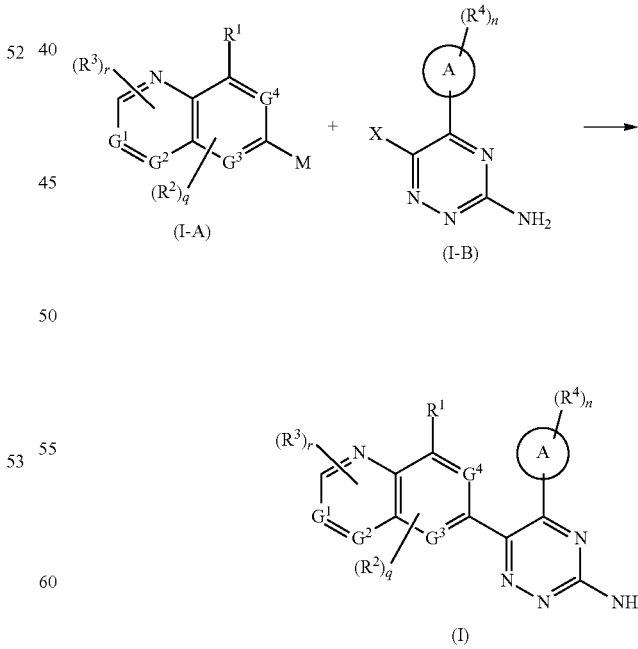
subjecting a compound of formula (I-A) and a compound of formula (I-B) to a coupling reaction to obtain the compound of formula (I), wherein:
X is halogen;
M is

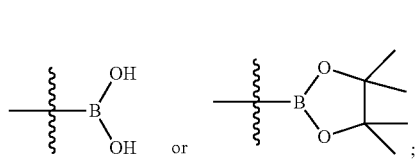

ring A, $G^1$-$G^4$, $R^1$-$R^4$, r, q and n are as defined in claim 1.

11. A method for preparing the compound of formula (Iaa) according to claim 2, comprising:

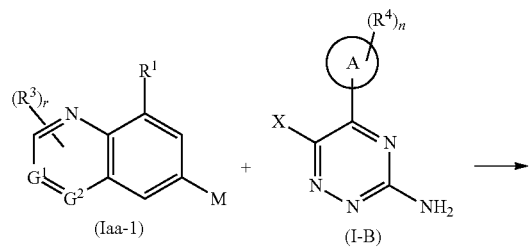

subjecting a compound of formula (Iaa-1) and a compound of formula (I-B) to a coupling reaction to obtain the compound of formula (Iaa), wherein:
X is halogen;
M is

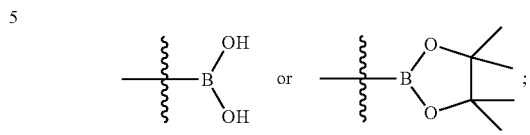

ring A, $G^1$, $G^2$, $R^1$, $R^3$, $R^4$, r and n are as defined in claim 2.

12. A pharmaceutical composition, comprising the compound according to claim 1, and one or more pharmaceutically acceptable carriers, diluents or excipients.

13. A method for treating a disease or condition ameliorated by inhibition of $A_{2a}$ receptor in a subject, the method comprising administering to the subject the pharmaceutical composition according to claim 12, wherein the disease or condition is selected from the group consisting of cancer, depression, Parkinson's disease, Huntington's disease, Alzheimer's disease, abnormal movement disorder, sleep disorder, and wherein the cancer is selected from the group consisting of melanoma, brain tumor, esophageal cancer, stomach cancer, liver cancer, pancreatic cancer, colorectal cancer, lung cancer, kidney cancer, breast cancer, ovarian cancer, prostate cancer, skin cancer, neuroblastoma, sarcoma, osteochondroma, osteoma, osteosarcoma, seminoma, testicular tumor, uterine cancer, head and neck cancer, multiple myeloma, malignant lymphoma, polycythemia vera, leukemia, thyroid tumor, ureteral tumor, bladder tumor, gallbladder cancer, cholangiocarcinoma, chorionic epithelioma and pediatric tumor.

14. A method for treating a disease or condition ameliorated by inhibition of $A_{2b}$ receptor in a subject, the method comprising administering to the subject the pharmaceutical composition according to claim 12, wherein the disease or condition is selected from the group consisting of cancer, depression, Parkinson's disease, Huntington's disease, Alzheimer's disease, abnormal movement disorder, sleep disorder, and wherein the cancer is selected from the group consisting of melanoma, brain tumor, esophageal cancer, stomach cancer, liver cancer, pancreatic cancer, colorectal cancer, lung cancer, kidney cancer, breast cancer, ovarian cancer, prostate cancer, skin cancer, neuroblastoma, sarcoma, osteochondroma, osteoma, osteosarcoma, seminoma, testicular tumor, uterine cancer, head and neck cancer, multiple myeloma, malignant lymphoma, polycythemia vera, leukemia, thyroid tumor, ureteral tumor, bladder tumor, gallbladder cancer, cholangiocarcinoma, chorionic epithelioma and pediatric tumor.

* * * * *